United States Patent
Khare et al.

(10) Patent No.: US 12,330,047 B2
(45) Date of Patent: Jun. 17, 2025

(54) SYSTEM FOR GENERATING SIMULATED ANIMAL DATA AND MODELS

(71) Applicant: SPORTS DATA LABS, INC., Royal Oak, MI (US)

(72) Inventors: Vivek Khare, Cupertino, CA (US); Mark Gorski, Royal Oak, MI (US); Stanley Mimoto, Bethel Island, CA (US); Anuroop Yadav, Livingston, NJ (US)

(73) Assignee: Sports Data Labs, Inc., Royal Oak, MI (US)

( * ) Notice: Subject to any disclaimer, the term of this patent is extended or adjusted under 35 U.S.C. 154(b) by 231 days.

(21) Appl. No.: 17/251,092

(22) PCT Filed: Sep. 8, 2020

(86) PCT No.: PCT/US2020/049678
§ 371 (c)(1),
(2) Date: Dec. 10, 2020

(87) PCT Pub. No.: WO2021/046519
PCT Pub. Date: Mar. 11, 2021

(65) Prior Publication Data
US 2022/0323855 A1 Oct. 13, 2022

Related U.S. Application Data

(60) Provisional application No. 63/027,491, filed on May 20, 2020, provisional application No. 62/897,064, filed on Sep. 6, 2019.

(51) Int. Cl.
*A63F 13/212* (2014.01)
*A63F 13/217* (2014.01)
(Continued)

(52) U.S. Cl.
CPC .......... *A63F 13/212* (2014.09); *A63F 13/217* (2014.09); *A63F 13/65* (2014.09); *A63F 13/90* (2014.09); *A63F 2300/8094* (2013.01)

(58) Field of Classification Search
CPC .. A63F 2300/8094; A63F 13/90; A63F 13/65; A63F 13/217; A63F 13/212
See application file for complete search history.

(56) References Cited

U.S. PATENT DOCUMENTS 7,415,359 B2   8/2008   Hill et al.
8,275,635 B2   9/2012   Stivoric et al.
(Continued)

FOREIGN PATENT DOCUMENTS

EP    0 959 444 A1    11/1999
JP    2018120785 A    8/2018
(Continued)

OTHER PUBLICATIONS

Intl Search Report mailed Dec. 4, 2020 for PCT/US20/49678 filed Sep. 8, 2020, 20 pgs.
(Continued)

*Primary Examiner* — Malina D. Blaise
(74) *Attorney, Agent, or Firm* — BROOKS KUSHMAN P.C.

(57) ABSTRACT

A method for generating and distributing simulated animal data includes a step of receiving a set of real animal data at least partially obtained from one or more sensors that receive, store, or send information related to one or more targeted individuals. Simulated animal data is generated from at least a portion of real animal data or one or more derivatives thereof. Finally, the simulated animal data is provided to a computing device. Characteristically, one or more parameters or variables of the one or more targeted individuals can be modified.

62 Claims, 12 Drawing Sheets

(51) Int. Cl.
*A63F 13/65* (2014.01)
*A63F 13/90* (2014.01)

(56) References Cited

U.S. PATENT DOCUMENTS

| | | | |
|---|---|---|---|
| 8,360,835 B2* | 1/2013 | Strause | G06Q 50/34 |
| | | | 463/7 |
| 9,005,016 B2 | 4/2015 | Amaitis et al. | |
| 9,396,486 B2 | 7/2016 | Stivoric et al. | |
| 9,886,788 B2 | 2/2018 | Hugel et al. | |
| 10,318,013 B1* | 6/2019 | Banks | G06F 9/541 |
| 10,755,466 B2* | 8/2020 | Chamdani | A63F 13/212 |
| 10,861,170 B1* | 12/2020 | Li | G06T 7/73 |
| 11,471,085 B2* | 10/2022 | Mrvaljevic | A61B 5/24 |
| 2007/0063850 A1 | 3/2007 | Devaul et al. | |
| 2007/0293289 A1 | 12/2007 | Loeb | |
| 2009/0029769 A1* | 1/2009 | Muller | A63F 13/58 |
| | | | 463/31 |
| 2011/0246509 A1 | 10/2011 | Takahito et al. | |
| 2013/0324239 A1 | 12/2013 | Ur et al. | |
| 2014/0278220 A1* | 9/2014 | Yuen | A61B 5/681 |
| | | | 702/150 |
| 2015/0165312 A1 | 7/2015 | Kiani | |
| 2015/0190072 A1* | 7/2015 | Armstrong | A61B 5/1118 |
| | | | 600/300 |
| 2015/0250396 A1 | 9/2015 | William et al. | |
| 2017/0012972 A1* | 1/2017 | Tanaka | G06F 1/1698 |
| 2017/0169656 A1* | 6/2017 | Froy, Jr. | G07F 9/009 |
| 2017/0209053 A1* | 7/2017 | Pantelopoulos | A61B 5/7278 |
| 2018/0036591 A1* | 2/2018 | King | H04N 5/76 |
| 2018/0165864 A1* | 6/2018 | Jin | G06F 3/0346 |
| 2018/0208062 A1 | 7/2018 | Kanada et al. | |
| 2019/0087519 A1 | 3/2019 | Mercury et al. | |
| 2019/0148010 A1 | 5/2019 | Aliamiri | |
| 2019/0220975 A1* | 7/2019 | Hsieh | G16H 30/40 |
| 2020/0082735 A1* | 3/2020 | Nel | G06F 3/011 |
| 2020/0179807 A1* | 6/2020 | Yu | A63F 13/67 |
| 2020/0188732 A1 | 6/2020 | Kruger | |
| 2020/0221958 A1 | 7/2020 | Bhatkar et al. | |
| 2020/0253476 A1* | 8/2020 | Khare | A61B 5/7475 |
| 2020/0254332 A1 | 8/2020 | Macri et al. | |
| 2020/0401222 A1* | 12/2020 | Wisbey | H04R 5/033 |
| 2021/0335004 A1* | 10/2021 | Zohar | G06T 7/74 |
| 2022/0323855 A1* | 10/2022 | Khare | A63F 13/65 |
| 2023/0010480 A1* | 1/2023 | Li | G06V 20/46 |
| 2023/0034337 A1* | 2/2023 | Gorski | G07F 17/323 |

FOREIGN PATENT DOCUMENTS

| | | |
|---|---|---|
| JP | 2019088774 A | 6/2019 |
| JP | 2019128904 A | 8/2019 |
| RU | 2568975 | 11/2015 |
| WO | 02/092101 A1 | 11/2002 |
| WO | 2013/041445 A1 | 3/2013 |

OTHER PUBLICATIONS

Supp. EP Search Report dtd Nov. 30, 2023 for EP Appn. No. 20861548.4, 12 pgs.
Japanese Office Action dtd Jul. 30, 2024 for JP Appn. No. 2022-514191, 8 pgs (including Machine Translation).
Canadian Office Action dtd Aug. 6, 2024 for CA Appn. No. 3,150,004, 10 pgs.
Written Opinion & Sch Rpt dtd Sep. 25, 2024 for Singapore Appn. No. 11202202177T, 10 pgs.
Anonymous, "Long short-term memory", Wikipedia, 2019, retrieved from https://en.wikipedia.org/wiki/Long short-term memory, pp. 1-11.
Anonymous, "Generative adversarial network," Wikipedia, 2019, retrieved from https://en.wikipedia.org/wiki/Generative adversarial network, 32 pgs.
Tsunoda, T. et al., Footbal Action Recognition Using Hierarchical LSTM, 2017 IEEE Conference on Computer Vision and Pattern Recognition Workshops, IEEE, 2017, pp. 155-163.
EP Search Report dtd Nov. 30, 2023 for EP Appn. No. 20861548.4, 12 pgs.
EP Search Report dtd Feb. 28, 2024 for EP Appn. No. 23210085.9, 7 pgs.

* cited by examiner

SYSTEM FOR GENERATING SIMULATED ANIMAL DATA AND MODELS

CROSS-REFERENCE TO RELATED APPLICATIONS

This application is the U.S. national phase of PCT Appln. No. PCT/US2020/049678 which claims the benefit of U.S. provisional application Ser. No. 62/897,064 filed Sep. 6, 2019 and U.S. provisional application Ser. No. 63/027,491 filed May 20, 2020, the disclosures of which are hereby incorporated in their entirety by reference herein.

TECHNICAL FIELD

In at least one aspect, the present invention is related to systems and methods for generating simulated animal data from real animal data.

BACKGROUND

The continuing advances in the availability of information over the internet have substantially changed the way that business is conducted. Simultaneous with this information explosion, sensor technology, and in particular, biosensor technology, has also progressed. In particular, miniature biosensors that measure electrocardiogram signals, blood flow, body temperature, perspiration levels, and breathing rate are now available. The ability for data from such sensors to be transmitted wirelessly and over the internet has opened up potential new applications for data set collections.

With advancements in sensor technology, new animal data sets are being created. However, users that desire animal data sets featuring specific characteristics related to targeted subjects, sensors, activities, conditions, and other variables or parameters can face obstacles related to data collection as data acquisition can be costly, time-consuming, and challenging to collect. Oftentimes, data sets do not exist. Concurrently, demand for such targeted animal data sets in fields such as healthcare, insurance, wellness monitoring, fitness, virtual sports, gaming, sports betting, and the like is increasing as data can be used in a variety of simulations and models to engage users and evaluate outcomes related to one or more future occurrences. Systems and methods to provide desired animal data sets to incorporate into such simulations do not exist.

Accordingly, there is a need for creating artificial data from real animal data that can be customized and tailored based on the preference of the user.

SUMMARY

In at least one aspect, the present invention provides a method for generating and distributing simulated animal data. The method includes a step of receiving one or more sets of real animal data at least partially obtained from one or more sensors that receive, store, or send information related to one or more targeted individuals. Simulated animal data is generated from at least a portion of real animal data or one or more derivatives thereof. Finally, the simulated animal data is provided to a computing device. Characteristically, one or more parameters or variables of the one or more targeted individuals can be modified.

In another aspect, a system for generating and providing simulated animal data by executing the methods herein is provided. The system including a computing device is operable to execute steps of receiving one or more sets of real animal data at least partially obtained from one or more sensors that receive, store, or send information related to one or more targeted individuals; generating simulated animal data from at least a portion of real animal data or one or more derivatives thereof; and providing at least a portion of the simulated animal data to a computing device. Characteristically, one or more parameters or variables of the one or more targeted individuals can be modified.

In another aspect, simulated animal data derived from real animal data at least partially obtained from one or more sensors is used to create, enhance, or modify one or more insights, computed assets, or predictive indicators.

In another aspect, at least a portion of the simulated animal data is used in one or more simulation systems to engage one or more users, whereby the simulation system is at least one of: a game-based system, augmented reality system, virtual reality system, mixed reality system, or an extended reality system.

In another aspect, simulated animal data derived from real animal data at least partially obtained from one or more sensors is used as one or more inputs in one or more further simulations to generate simulated data. At least a portion of the simulated data is used to create, modify, or enhance one or more insights, computed assets, or predictive indicators.

In another aspect, simulated animal data derived from real animal data at least partially obtained from one or more sensors is used as one or more inputs in one or more further simulations to generate simulated data. At least a portion of the simulated data is used in a simulation system to engage users, whereby the simulation system is at least one of: a game-based system, augmented reality system, virtual reality system, mixed reality system, or an extended reality system.

In another aspect, simulated data derived from real animal data at least partially obtained from one or more sensors is used either directly or indirectly: (1) as a market upon which one or more wagers are placed or accepted; (2) to create, modify, enhance, acquire, offer, or distribute one or more products (3) to evaluate, calculate, derive, modify, enhance, or communicate one or more predictions, probabilities, or possibilities; (4) to formulate one or more strategies; (5) to take one or more actions; (6) to mitigate or prevent one or more risks; (7) to recommend one or more actions; (8) as one or more signals or readings utilized in one or more simulations, computations, or analyses; (9) as part of one or more simulations, an output of which directly or indirectly engages with one or more users; (10) as one or more core components or supplements to one or more mediums of consumption; (11) in one or more promotions; or (12) a combination thereof.

In another aspect, simulated data derived from real animal data at least partially obtained from one or more sensors is used either directly or indirectly in one or more sports betting, insurance, health, fitness, biological performance, or entertainment applications.

In another aspect, artificial data is generated to replace one or more outlier values or missing values generated from one or more sensors.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements and wherein.

DETAILED DESCRIPTION

Figure 1:
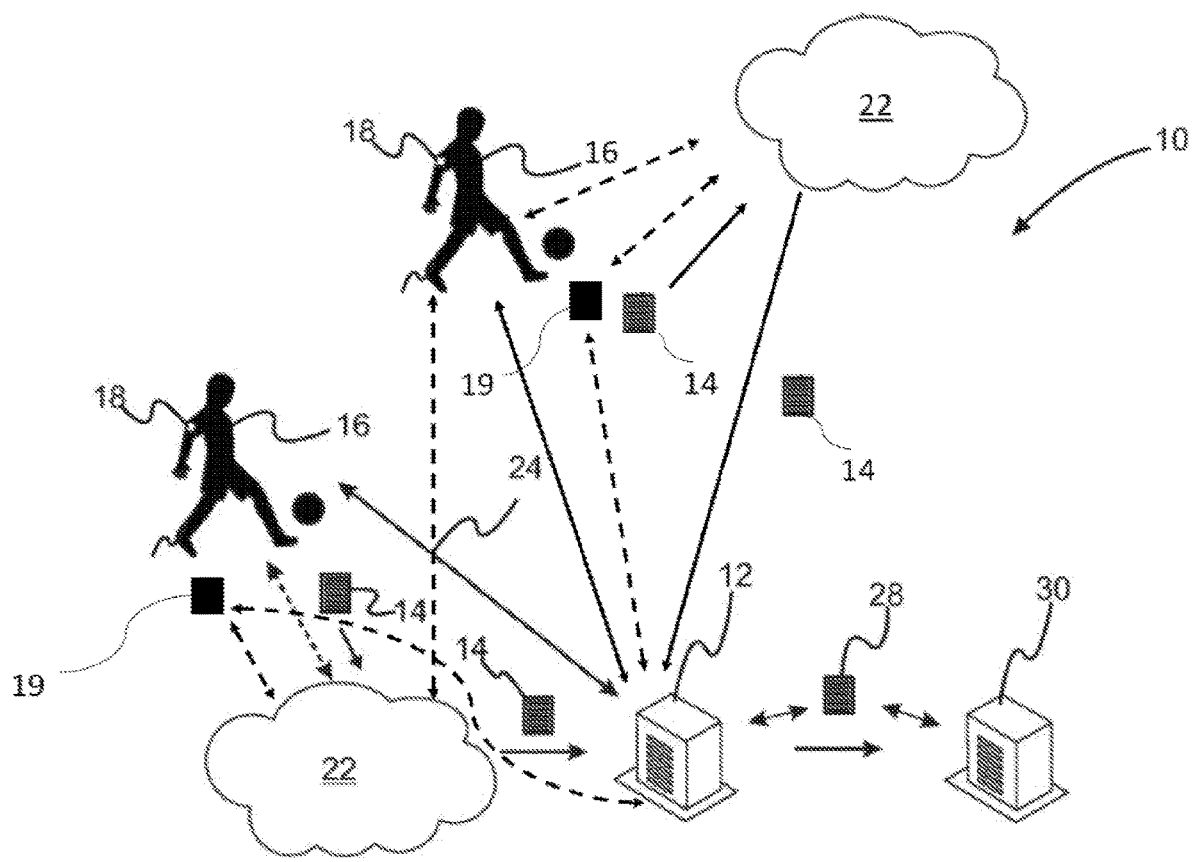
FIG. 1 is a schematic of a system for generating simulated animal data from real animal data.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The phrase "data is" is meant to include both "datum is" and "data are," as well as all other possible meanings, and is not intended to be limiting in any way.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

The term "one or more" means "at least one" and the term "at least one" means "one or more." The terms "one or more" and "at least one" include "plurality" and "multiple" as a subset. In a refinement, "one or more" includes "two or more."

Throughout this application, where publications are referenced, the disclosures of these publications in their entireties are hereby incorporated by reference into this application to more fully describe the state of the art to which this invention pertains.

While the terms "probability" and "odds" are mathematically different (e.g., probability can be defined as the number of occurrences of a certain event expressed as a proportion of all events that could occur, whereas odds can be defined as the number of occurrences of a certain event expressed as a proportion of the number of non-occurrences of that event), both describe the likeliness that an event will occur. They are used interchangeably to avoid redundancy, and reference to one term should be interpreted to mean reference to both.

With respect to the terms "bet" and "wager," both terms mean an act of taking a risk (e.g., money, non-financial consideration) on the outcome of a future event. Risk includes both financial (e.g., monetary) and non-financial risk (e.g., health, life). A risk can be taken against another one or more parties (e.g., an insurance company deciding whether to provide insurance) or against oneself (e.g., an individual deciding whether to obtain insurance), on the basis of an outcome, or the likelihood of an outcome, of a future event. Examples include gambling (e.g., sports betting), insurance, and the like. Where one of these two terms are used herein, the presently disclosed and claimed subject matter can use either of the other two terms interchangeably.

The term "server" refers to any computer or computing device (including, but not limited to, desktop computer, notebook computer, laptop computer, mainframe, mobile phone, smart watch-glasses, augmented reality headset, virtual reality headset, and the like), distributed system, blade, gateway, switch, processing device, or a combination thereof adapted to perform the methods and functions set forth herein.

When a computing device is described as performing an action or method step, it is understood that the one or more computing devices are operable to perform the action or method step typically by executing one or more lines of source code. The actions or method steps can be encoded onto non-transitory memory (e.g., hard drives, optical drive, flash drives, and the like).

The term "computing device" refers generally to any device that can perform at least one function, including communicating with another computing device. In a refinement, a computing device includes a central processing unit that can execute program steps and memory for storing data and a program code.

The term "electronic communication" means that an electrical signal is either directly or indirectly sent from an originating electronic device to a receiving electrical device. Indirect electronic communication can involve processing of the electrical signal, including but not limited to, filtering of the signal, amplification of the signal, rectification of the signal, modulation of the signal, attenuation of the signal, adding of the signal with another signal, subtracting the signal from another signal, subtracting another signal from the signal, and the like. Electronic communication can be accomplished with wired components, wirelessly-connected components, or a combination thereof.

The processes, methods, or algorithms disclosed herein can be deliverable to/implemented by a computer, controller, or other computing device, which can include any existing programmable electronic control unit or dedicated electronic control unit. Similarly, the processes, methods, or algorithms can be stored as data and instructions executable by a computer, controller, or other computing device in many forms including, but not limited to, information permanently stored on non-writable storage media such as ROM devices and information alterably stored on writeable storage media such as floppy disks, magnetic tapes, CDs, RAM devices, other magnetic and optical media, and shared or dedicated cloud computing resources. The processes, methods, or algorithms can also be implemented in an executable software object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software, and firmware components.

The terms "subject" and "individual" are synonymous and refer to a human or other animal, including birds, reptiles, amphibians, and fish, as well as all mammals including primates (particularly higher primates), horses, sheep, dogs, rodents, pigs, cats, rabbits, and cows. The one or more subjects may be, for example, humans participating in athletic training or competition, horses racing on a race track, humans playing a video game, humans monitoring their personal health, humans providing their data to a third party, humans participating in a research or clinical study, or humans participating in a fitness class. A subject or individual can also be a derivative of a human or other animal (e.g., lab-generated organism derived at least in part from a human or other animal), one or more individual components, elements, or processes of a human or another animal (e.g., cells, proteins, biological fluids, amino acid sequences, tissues, hairs, limbs) that make up the human or other animal, one or more digital representations that share at least one characteristic with a human or animal (e.g., data set representing a human that shares at least one characteristic with a human representation in digital form—such as sex, age, biological function as examples—but is not generated from any human that exists in the physical world; a simulated individual), or one or more artificial creations that share one or more characteristics with a human or other animal (e.g., lab-grown human brain cells that produce an electrical signal similar to that of human brain cells). In a refinement, the subject or individual can be one or more programmable computing devices such as a machine (e.g., robot, autonomous vehicle, mechanical arm) or network of machines that share at least one biological function with a human or other animal and from which one or more types of biological data can be derived, which may be, at least in part, artificial in nature (e.g., data from artificial intelligence-derived activity that mimics biological brain activity; biomechanical movement data derived a programmable machine).

The term "animal data" refers to any data obtainable from, or generated directly or indirectly by, a subject that can be transformed into a form that can be transmitted to a server or other computing device. Typically, the animal data is electronically transmitted with a wired or wireless connection. Animal data includes any subject-derived data, including any signals or readings, that can be obtained from one or more sensors or sensing equipment/systems, and in particular, biological sensors (biosensors). Animal data can also include descriptive data related to a subject, auditory data related to a subject, visually-captured data related to a subject, neurologically-generated data (e.g., brain signals from neurons), evaluative data related to a subject (e.g., skills of a subject), data that can be manually entered related to a subject (e.g., medical history, social habits, feelings of a subject), data that includes at least a portion of real animal data or one or more derivatives thereof, and the like. In a refinement, the term "animal data" is inclusive of any derivative of animal data. In another refinement, animal data includes any metadata gathered or associated with the animal data. In another refinement, animal data includes at least a portion of simulated data. In yet another refinement, animal data is inclusive of simulated data.

In some variations, the term "real animal data" is used interchangeably with the term "animal data." In other variations, the term "real animal data" refers to animal data at least partially obtained from one or more sensors that receive, store, and/or send information related to one or more targeted individuals or groups of targeted individuals.

The term "artificial data" refers to artificially-created data that is derived from, based on, or generated using, at least in part, real animal data or one or more derivatives thereof. It can be created by running one or more simulations utilizing one or more artificial intelligence techniques or statistical models, and can include one or more signals or readings from one or more non-animal data sources as one or more inputs. Artificial data can include any artificially-created data that shares at least one biological function with a human or another animal (e.g., artificially-created vision data, artificially-created movement data). It is inclusive of "synthetic data," which can be any production data applicable to a given situation that is not obtained by direct measurement. Synthetic data can be created by statistically modeling original data and then using those models to generate new data values that reproduce at least one of the original data's statistical properties. In a refinement, the term "artificial data" is inclusive of any derivative of artificial data. For the purposes of the presently disclosed and claimed subject matter, the terms "simulated data" and "synthetic data" are synonymous and used interchangeably with "artificial data," and a reference to any one of the terms should not be interpreted as limiting but rather as encompassing all possible meanings of all the terms. In a refinement, the term "artificial data" is inclusive of the term "artificial animal data."

The term "insight" refers to one or more descriptions that can be assigned to a targeted individual that describe a condition or status of the targeted individual utilizing at least a portion of their animal data. Examples include descriptions or other characterizations of stress levels (e.g., high stress, low stress), energy levels, fatigue levels, and the like. An insight may be quantified by one or more numbers or a plurality of numbers, and may be represented as a probability or similar odds-based indicator. An insight may also be quantified, communicated, or characterized by one or other metrics or indices of performance that are predetermined (e.g., codes, graphs, charts, plots, colors or other visual representations, plots, readings, numerical representations, descriptions, text, physical responses such as a vibration, auditory responses, visual responses, kinesthetic responses, or verbal descriptions). An insight may also include one or more visual representations related to a condition or status of the of one or more targeted subjects (e.g., an avatar or realistic depiction of a targeted subject visualizing future weight loss goals on the avatar or depiction of the targeted subject). In a refinement, an insight is a personal score or other indicator related to one or more targeted individuals or groups of targeted individuals that utilizes at least a portion of simulated data to (1) evaluate, assess, prevent, or mitigate animal data-based risk, (2) to evaluate, assess, and optimize animal data-based performance (e.g. biological performance), or a combination thereof. The personal indicator score can be utilized by the one or more targeted subjects from which the animal data or one or more derivatives thereof are derived from, as well as one or more third parties (e.g., insurance organizations, healthcare providers or professionals, sports performance coaches, medical billing organizations, fitness trainers, and the like). In another refinement, an insight is derived from two or more types of animal data. In another refinement, an insight includes one or more signals or readings from one or more non-animal data sources as one or more inputs in one or more computations, calculations, derivations, incorporations, simulations, extractions, extrapolations, modifications, enhancements, creations, estimations, deductions, inferences, determinations, processes, communications, and the like. In another refinement, an insight is comprised of a plurality of insights. In yet another refinement, an insight is assigned to multiple targeted individuals, as well as one or more groups of targeted individuals.

The term "computed asset" refers to one or more numbers, a plurality of numbers, values, metrics, readings, insights, graphs, charts, or plots that are derived from at least a portion of the animal data or one or more derivatives thereof (which can be inclusive of simulated data). The one or more sensors used herein initially provide an electronic signal. The computed asset is extracted or derived, at least in part, from the one or more electronic signals or one or more derivatives thereof. The computed asset describes or quantifies an interpretable property of the one or more targeted individuals or groups of targeted individuals. For example, electrocardiogram readings can be derived from analog front end signals (e.g., the electronic signal from the sensor), heart rate data (e.g., heart rate beats per minute) can be derived from electrocardiogram or PPG sensors, body temperature data can be derived from temperature sensors, perspiration data can be derived or extracted from perspiration sensors, glucose information can be derived from biological fluid sensors, DNA and RNA sequencing information can be derived from sensors that obtain genomic and genetic data, brain activity data can be derived from neurological sensors, hydration data can be derived from in-mouth saliva or sweat analysis sensors, location data can be derived from GPS or RFID-based sensors, biomechanical data can be derived from optical or translation sensors, and breathing rate data can be derived from respiration sensors. In a refinement, a computed asset includes one or more signals or readings from one or more non-animal data sources as one or more inputs in one or more computations, calculations, derivations, incorporations, simulations, extractions, extrapolations, modifications, enhancements, creations, estimations, deductions, inferences, determinations, processes, communications, and the like. In another refinement, a computed asset is derived from two or more types of animal data. In another refinement, a computed asset is comprised of a plurality of computed assets.

The term "predictive indicator" refers to a metric or other indicator (e.g., one or more colors, codes, numbers, values, graphs, charts, plots, readings, numerical representations, descriptions, text, physical responses, auditory responses, visual responses, kinesthetic responses) from which one or more forecasts, predictions, probabilities, assessments, possibilities, projections, or recommendations related to one or more outcomes for one or more future events that includes one or more targeted individuals, or one or more groups of targeted individuals, can be calculated, computed, derived, extracted, extrapolated, simulated, created, modified, assigned, enhanced, estimated, evaluated, inferred, established, determined, converted, deduced, observed, communicated, or actioned upon. In a refinement, a predictive indicator is a calculated computed asset derived from at least a portion of the animal data or one or more derivatives thereof. In another refinement, a predictive indicator includes one or more signals or readings from one or more non-animal data sources as one or more inputs in the one or more calculations, computations, derivations, extractions, extrapolations, simulations, creations, modifications, assignments, enhancements, estimations, evaluations, inferences, establishments, determinations, conversions, deductions, observations, or communications of its one or more forecasts, predictions, probabilities, possibilities, assessments, projections, or recommendations. In another refinement, a predictive indicator includes at least a portion of simulated data as one or more inputs in the one or more calculations, computations, derivations, extractions, extrapolations, simulations, creations, modifications, assignments, enhancements, estimations, evaluations, inferences, establishments, determinations, conversions, deductions, observations, or communications of its one or more forecasts, predictions, probabilities, possibilities, assessments, projections, or recommendations. In another refinement, a predictive indicator is derived from two or more types of animal data. In yet another refinement, a predictive indicator is comprised of a plurality of predictive indicators.

With reference to FIG. 1, a computer-implemented method and system for generating simulated data is provided. Simulation system 10 includes a computing device 12 that receives animal data 14. Typically, methods and systems for generating such animal data 14 deploy one or more sensors 18 that collect real animal data from one or more targeted individuals 16. In some variations, animal data refers to data related to a targeted individual (e.g., their body) derived, at least in part, from one or more sensors 18 and in particular, biological sensors (biosensors). In many useful applications, the targeted individual is a human (e.g., an athlete, a soldier, a healthcare patient, a research subject, a participant in a fitness class, a video gamer) and the animal data is human data. Animal data can be derived from a targeted individual or multiple targeted individuals (e.g., including a targeted group of multiple targeted individuals, multiple targeted groups of multiple targeted individuals). The animal data can be obtained from a single sensor on each targeted individual, or from multiple sensors on each targeted individual. In some cases, a single sensor can capture data from multiple targeted individuals, a targeted group of multiple targeted individuals, or multiple targeted groups of multiple targeted individuals (e.g., an optical-based camera sensor that can locate and measure distance run for a targeted group of targeted individuals). Each source sensor can provide a single type of animal data or multiple types of animal data. In a variation, sensor 18 can include multiple sensing elements to measure one or more parameters within a single sensor (e.g., heart rate and accelerometer data). In a refinement, one or more sensors 18 include at least one biological sensor (biosensor). One or more sensors 18 can collect data from a targeted individual engaged in a variety of activities including strenuous activities that can change one or more biological signals or readings in a targeted individual such as blood pressure, heart rate, or biological fluid levels. Activities may also include sedentary activities such as sleeping or sitting where changes in biological signals or readings may have less variance. In a variation, simulation system 10 can also receive (e.g., collect) animal data not obtained from sensors (e.g., animal data that is manually inputted; sensor-collected animal data sets that include artificial data values not generated from a sensor).

Still referring to FIG. 1, one or more sensors 18 can transmit animal data 14 wirelessly to computing device 12 either directly or via cloud 22, or via wired connection 24. Cloud 22 can be the internet, a public cloud, a private cloud, or hybrid cloud. In a refinement, computing device 12 communicates with the one or more sensors 18 through a local server (e.g., a localized or networked server/storage, localized storage device, distributed network of computing devices) or other computing device 19 that mediates the sending of animal data 14 to computing device 12 (e.g., it collects the data and transmits it to computing device 12, or it collects the data and transmits it to a cloud that can be accessed by computing device 12). For example, an intermediate computing device can be a smartphone or other computing device. The animal data that enters the system can be raw or transformed (e.g., manipulated, processed) data obtained from one or more sensors. In a refinement, transformed data includes data that has been cleaned, edited, modified, and/or manipulated in one or more ways (e.g., data that has metadata attached to it, data that has been transformed into one or more readings related to heart rate, blood pressure, perspiration rate, and the like). In another refinement, the act of transforming data includes one or more calculations, computations, derivations, incorporations, simulations, extractions, additions, subtractions, extrapolations, modifications, enhancements, creations, estimations, deductions, inferences, determinations, conversions, processes, communications, and the like. For example, in the context of measuring a heart rate, a biological sensor can be configured to measure electrical signals from the targeted subject's body, transforming (e.g., converting) analog-based measurements to digital readings, and transmitting the digital readings. In another example, a computing device can receive digital readings from a sensor and transform digital readings into one or more heart rate values. Additional details related to a system for measuring a heart rate and other biological data are disclosed in U.S. patent application Ser. No. 16/246,923 filed Jan. 14, 2019 and U.S. Pat. No. PCT/US20/13461 filed Jan. 14, 2020; the entire disclosures of which are hereby incorporated by reference. In yet another refinement, the act of transforming data includes one or more actions that normalize, timestamp, aggregate, tag, store, manipulate, denoise, enhance, organize, visualize, analyze, anonymize, synthesize, summarize, replicate, productize, or synchronize the animal data. In still another refinement, one or more transformations occur by utilizing (e.g., incorporating) one or more signals or readings from non-animal data.

Still referring to FIG. 1, Computing device 12 utilizes at least a portion of the real animal data or one or more derivatives thereof and either executes a simulation by executing steps of a simulation program with data that has been transformed into a form to be inputted into a simulation, or sends the data to another one or more computing devices 30 (e.g., computing device associated with or in a network with computing device 12, or third-party computing device) for a simulation to be executed. In this regard, computing device 12 and one or more computing devices 30 can be operable to execute a simulation. An executed simulation can be one in which one or more simulated targeted individuals participate, and wherein one or more parameters or variables of the simulated targeted individuals can be changed, randomized, and/or modified. In a variation, one or more parameters or variables of the one or more targeted individuals can include any input relevant to, or related to, the one or more targeted individuals (including characteristics both internal and external to the one or more targeted individuals), as well as any input that impacts (e.g., influences, changes, alters, adjusts), or has the potential to impact, the one or more outputs in the one or more simulations based upon its inclusion in the simulation. In a refinement, one or more parameters or variables modified to generate simulated data are comprised of non-animal data. In one form of simulation, a simulation provides a medium for user engagement with one or more inputs and outputs confined to a computing device. In these cases, a simulation can be integrated with other components (e.g., hardware, software) that interact with one or more users. For example, the simulation system that performs the simulation and incorporates at least a portion of real animal data or one or more derivatives thereof can be a game-based system (e.g., video gaming system, virtual gambling system, fitness gaming system, and the like), augmented reality system, virtual reality system, mixed reality system, extended reality system, or other forms of interactive simulations. In another form of simulation, a simulation is a method for implementing a model over a period of time to predict one or more future occurrences. The simulated data can be derived from one or more simulated events, concepts, objects, or systems. It can be generated using one or more statistical models or artificial intelligence techniques. Characteristically, a plurality of simulations may occur utilizing the same one or more inputs, and a simulation may be comprised of a plurality of simulations. In a refinement, a plurality of simulation systems can be operable to work together. For example, simulated data may be generated by a computing device and provided to another computing device operating a simulation program in which the simulated data is inputted. In another refinement, the one or more simulations may include one or more data sets from non-animal data as one or more inputs.

Upon execution of a simulation program by computing device 12 and/or one or more computing devices 30, simulated data 28 is generated and provided to one or more computing devices. Characteristically, generated simulated data can be artificial animal data (e.g., artificial heart rate data, artificial respiratory rate data, artificial glucose data, and the like). For example, the simulated animal data can indicate a simulated target individual's level of fatigue at any given point within a simulated sporting event, with one or more variables or parameters being adjusted within the simulation (e.g., distance run, environmental data), one or more of which may be signals or readings from non-animal data (e.g., time). As another example, simulated animal data such as simulated heart rate readings can represent a simulated targeted individual's future biological activity within a simulated sporting event. Advantageously, such information can be utilized as part of one or more predictions, probabilities, or possibilities related to the simulated animal data. As another example, the simulated animal data can also indicate or predict how one or more simulated targeted subjects will respond to a specific drug in a simulated pharmaceutical study, with the one or more drugs and the one or more characteristics of the one or more targeted individuals being one or more variables in the simulation. In many useful variations, the one or more simulated targeted subjects in the simulation are representative (e.g., similar) of one or more real-world targeted subjects or groups of targeted subjects, sharing one or more biological and/or non-biological characteristics associated with the one or more real-world targeted subjects or groups of targeted subjects, thereby enabling the one or more simulated targeted subjects or groups of targeted subjects to represent the one or more real-world targeted subjects or groups of targeted subjects in the simulation. Simulated data can also include real animal data that has been transformed into a format to be inputted into a simulation (e.g., a subject's real heart rate data incorporated into a simulation system such as a video game system). In a refinement, at least a portion of the simulated data can be used to create, enhance, or modify one or more insights, computed assets, or predictive indicators.

In a refinement, at least a portion of the simulated animal data 28 or one or more derivatives thereof are used as one or more inputs in one or more further simulations. The one or more further simulations can be tailored to utilize the previously generated simulated animal data to predict one or more future occurrences. For example, simulated animal data 28 may be used in a sporting event simulation to predict one or more outcomes (e.g., by having a targeted subject's generated artificial "fatigue level" for an event such as a professional sports match, one or more outcomes—win/loss, whether the targeted subject will experience a biological event such as exertional heatstroke, and the like—may be predicted). Simulated animal data 28 may also be used in one or more further simulations to simulate other animal data (e.g., a subject's simulated heart rate data may be used as an input to generate another simulated biological output such as simulated hydration or glucose information). A variety of simulated biological functions and activities can benefit from generating and incorporating simulated animal data including simulations of physical activity (e.g., sporting events, fitness activities), health monitoring (e.g., insurance, military, home monitoring/telehealth applications), biological analysis (e.g., DNA sequencing), biological response (e.g., cellular or biological fluid response to a specific type of drug), and the like. In a refinement, the simulation simulates based upon one or more targeted individuals engaged in at least one of: a fitness activity, a sporting event (e.g., professional sports competition), a health assessment (e.g., remote patient monitoring, in-hospital patient evaluations, general wellness platform that provide feedback from the one or more sensors), or an insurance evaluation (e.g., including receiving an insurance quote, obtaining insurance, adjusting insurance rates). In another refinement, at least a portion of the one or more simulated data sets can be used to create, modify, or enhance one or more insights, computed assets, or predictive indicators. Simulated animal data 28 can also be used within a simulation that engages one or more users. In a variation, simulated animal data 28 may be generated based on one or more animal data sets from a plurality of subjects that are representative of one or more defined groups. For example, the system may generate simulated average heart rate data for a defined group of individuals featuring specific biological characteristics in a defined situational/contextual environment (e.g., e.g., engaged in a specific activity for a specific period of time). Identity of the one or more targeted subjects or targeted groups of targeted subjects may or may not be known. In another variation, simulated data may be used as a baseline data set to represent a specific subject group (with one or more defined characteristics) in the one or more further simulations. Advantageously, the one or more simulations can be implemented in real-time or near real-time with one or more parameters or variables adjusted. In this context, near real-time means that the transmission is not purposely delayed except for necessary processing by the sensor and computing device. In a refinement, simulated data derived from at least a portion of real animal data or one or more derivatives thereof can be used either directly or indirectly: (1) as a market upon which one or more wagers are placed or accepted; (2) to create, modify, enhance, acquire, offer, or distribute one or more products; (3) to evaluate, calculate, derive, modify, enhance, or communicate one or more predictions, probabilities, or possibilities; (4) to formulate one or more strategies; (5) to take one or more actions; (6) to mitigate or prevent one or more risks; (7) to recommend one or more actions; (8) as one or more signals or readings utilized in one or more simulations, computations, or analyses; (9) as part of one or more simulations, an output of which directly or indirectly engages with one or more users; (10) as one or more components or supplements to one or more mediums of consumption; (11) in one or more promotions; or (12) a combination thereof.

In a variation with respect to application (1), a market can be a specific type or category of bet or wager on a particular event (e.g., a sporting event, a health or medical event, a simulated event). A market can be created and offered or leveraged for any event. Oftentimes, organizations that accept one or more bets offer a plurality of betting markets on each event, with odds listed for each market. Specific types or categories can include a proposition bet ("prop bet"), spread bet, a line bet, a future bet, a parlay bet, a round-robin bet, a handicap bet, an over/under bet, a full cover bet, or a teaser bet. In addition, acceptance of a wager can be, for example, acceptance of a bet by a wagering system utilizing the one or more outputs (e.g., a bet type utilizing a predictive indicator derived from simulated data), acceptance by an insurance system (e.g., insurance provider) of a payment from an individual that is correlated with a risk taken by the insurance provider based upon the one or more outputs (e.g., the insurance policy provided to an individual, which may or may not cost the company more money, based on the likelihood of the individual experiencing any given biological event forecasted by the predictive indicator derived from simulated data), acceptance by an insurance system of one or more treatments related a particular diagnosis for a given individual—and the payments and timelines associated with the one or more treatments—that is recommended by the healthcare provider based upon the simulated effectiveness of the treatment utilizing at least a portion of the individual's animal data and their generated simulated data, and the like.

In a variation with respect to application (2), one or more products can be one or more goods or services that are designed to be distributed or sold. A product can be any product in any industry or vertical that can be created, modified, enhanced, offered, or distributed, so long as the product uses at least a portion of simulated data either directly or indirectly. For example, a product can be a market upon which one or more wagers are placed or accepted. In a refinement, at least a portion of the simulated data or one or more derivatives thereof are used to create, modify, enhance, offer, acquire, accept, or distribute at least one of: a proposition bet, a spread bet, a line bet, a futures bet, a parlay bet, a round-robin bet, a handicap bet, an over/under bet, a full cover bet, or a teaser bet. It is inclusive of simulated data or one or more derivatives thereof leading to (or resulting in) the creation of a product. For example, a product can be the simulated data itself (e.g., purchasing the one or more outputs of a simulation), an insurance offering, a health application that displays the one or more simulated outputs, a suite of algorithms designed to provide a particular simulated insight related to a subject, a sports betting application, a consumer product that utilizes simulated data (e.g., beverages such as isotonic drinks that utilize simulated data to personalize ingredients based upon a subject's biological information, foods), and the like. For clarification purposes, "enhance" can include "to be part of" a product should the enhancement add value. In addition, and in many cases, "create" can be inclusive of "derive" and vice versa. Similarly, "create" can be inclusive of "generate" and vice versa. Furthermore, "modify" can be inclusive of "revise", "amend", "adjust", "change", and "refine." In addition, "offer" can be inclusive of "provide." Lastly, an "acquirer" of a product could be, for example, a consumer, an organization, another system, any other end point that could consume or receive the product, and the like.

In a variation with respect to application (3), the one or more predictions, probabilities, or possibilities can be related to a future outcome or occurrence, with one or more predictions, probabilities, or possibilities connected. For example, a probability may be calculated to determine the likelihood of any given athlete elevating his heart rate over 200 beats per minute in any given basketball game utilizing various types of data including the athlete's current heart rate, average heart rate, max heart rate, historical heart rate for similar conditions, biological fluid levels, sEMG data, the number of minutes on the court, total distance run, simulated biological data, environmental data, other situational/contextual information, and the like. Utilizing this probability, another probability may be calculated to determine the likelihood that the athlete will make baskets outside of n feet at a percentage exceeding n % when the athlete's heart rate is over 200 bpm. In addition, "communication" can include visualization of the one or more predictions, probabilities, or possibilities (e.g., displaying a probability via an application, displaying an output-based probability for a targeted individual within an augmented reality or virtual reality system), verbal communication of one or more predictions, probabilities, or possibilities (e.g., a voice-activated virtual assistant that informs a targeted individual of the likelihood an event can occur based on their simulated biological data, or that an event will happen. An example could be the likelihood of having low blood sugar if a certain action is not taken, the likelihood of having a stroke in the next n days based on the collected biological data, or that a biological-related event will occur based upon the simulated data), and the like. Lastly, modification of a prediction, probability, or possibility can include revising a previously determined prediction, probability, or possibility for an event.

In a variation with respect to application (4), a strategy can include any strategy that uses at least a portion of simulated data either directly or indirectly. For example, a strategy can be a plan of action to determine whether or not to insure an individual, whether or not to place a bet, whether or not to take a specific action related to the simulated data, and the like. A strategy can also include a complete trading/betting strategy that is completely based on simulations and simulated data to predict potential outcomes and thresholds upon which the predefined rules will action against. In addition, the one or more simulated data outputs or one or more derivatives thereof may be utilized in one or more further calculations, computations, derivations, extractions, extrapolations, simulations, creations, modifications, enhancements, estimations, evaluations, inferences, establishments, determinations, conversions, deductions, observations, or communications related to the formulation of one or more strategies. In this context, the term "formulation" can include of one or more modifications, enhancements, and the like.

In a variation with respect to application (5), an action can be any action that is directly or indirectly related to at least a portion of the simulated data. An action includes an action that is derived from (or results from) the simulated data. It can be, for example, an action to confirm or authenticate the health status of an individual, an action to insure an individual (e.g., the probability that a targeted subject has a heart attack in the next 24 months is x, so their premium will be y), an action to accept or reject a healthcare provider's personalized treatment plan for a subject's medical event or need (e.g., based upon one or more simulations, the probability that the treatment recommended by the healthcare provider will rehabilitate the targeted subject is n, so the insurer will agree to pay for w weeks of treatment at p price based upon the simulated data), an action related to a targeted individual's biology (e.g., a passenger in a self-driving car has a biological reading that triggers one more simulations to occur via a computing device, the output of which may alert the self-driving car to drive to the nearest hospital), an action to place a wager (e.g., the athlete's energy level derived from one or more simulations is at x percent, therefore a user places a bet), an action to take a specific action (e.g., a system communicating an action to take a specific action such as "place a bet," "run for 20 minutes today," "eat n number of calories today"), an action to take no action at all, and the like.

In a variation with respect to application (6), mitigation or prevention of risk can include any action, non-action, strategy, recommendation, reclassification of risk, changing of a risk profile, and the like related to reducing or preventing risk. It can also include taking additional risk.

In a variation with respect to application (7), to recommend one or more actions includes both a recommendation that is inferred by the simulated data either directly or indirectly (e.g., a predictive indicator derived from simulated data that provides a probability of an occurrence happening may infer an action to be taken) as well as a recommendation directly stated based on the one or more outputs (e.g., a recommendation that an action be taken based on a predictive indicator derived from one or more simulations that provide the probability of an occurrence happening or a prediction). In a refinement, a recommendation may be comprised of a plurality of recommendations.

In a variation with respect to application (8), a signal or reading can include any form and any format of information (e.g., including as one or more data sets).

In a variation with respect to application (9), a simulation includes both the production of one or more computer models, as well as imitation of one or more situations or processes. Simulations have a wide range of engagement uses, including simulations that are utilized to generate the one or more outputs, which any use of the outputs can be considered either direct or indirect engagement, as well as inclusion of the one or more outputs within one or more simulations, which may engage one or more users (e.g., a video game or other game-based system, an augmented reality or virtual reality system).

In a variation with respect to application (10), the one or more mediums of user consumption can be any medium where a user can directly or indirectly consume the one or more outputs from the one or more simulations. A medium can include, for example, a health monitoring application (e.g., remote monitoring platform) that communicates a heart status check via the one or more outputs, a remote rehabilitation or telehealth platform that communicates the one or more outputs to the platform during an activity (e.g., remote exercise, virtual doctor visit) while enabling the remote medical professional or rehabilitation specialist to see the patient via an integrated video display, an insurance application that communicates an insurance adjustment based at least in part from the simulated data output, a sports wagering platform utilizing the simulated data output, and the like. It can also include a media broadcast that incorporates the simulated data (e.g., providing a prediction related to the outcome of a sporting event), a sports streaming content platform (e.g., video platform) that integrates simulated data as a supplement to the live sports event being watched (e.g., enabling a user to place a wager while watching the live content), and the like. It can also include non-display mediums (e.g., a key fob or scannable object) that provides information related to the health status of one or more individuals to one or more other systems.

In a variation with respect to application (11), the one or more promotions can be any promotion that provides support in furtherance of the acceptance and/or acquisition (e.g., sale, distribution) of one or more products. This includes one or more advertisements, an offer that uses the simulated data (e.g., an offer to the targeted subject to obtain insurance with the potential of lowering a premium by enabling one or more simulations to be conducted utilizing the targeted subject's animal data), a discounting mechanism that uses simulated data (e.g., the n number of simulations predict that player X will lose the match vs player Y; therefore, the wagering system will provide the user/bettor with more favorable odds for player X to win the match, with updates to the odds occurring in real-time or near real-time based on new information collected by the simulation system and new simulations being run), and the like.

In a variation with respect to application (12), "a combination thereof" can include any combination of the aforementioned applications, including all of the aforementioned applications or a subset of the aforementioned applications.

In another refinement, computing device 12 or computing device 30 is operable to directly or indirectly: (1) offer or accept one or more wagers; (2) create, enhance, modify, acquire, offer, or distribute one or more products; (3) evaluate, calculate, derive, modify, enhance, or communicate one or more predictions, probabilities, or possibilities; (4) formulate one or more strategies; (5) take one or more actions; (6) mitigate or prevent one or more risks; (7) recommend one or more actions; (8) engage one or more users; or (9) a combination thereof.

As set forth above, one or more sensors 18 can include one or more biological sensors (biosensors). Biosensors collect biosignals, which in the context of the present embodiment are any signals or properties in, or derived from, animals that can be continually or intermittently measured, monitored, observed, calculated, computed, or interpreted, including both electrical and non-electrical signals, measurements, and artificially-generated information. A biosensor can gather biological data (including readings and signals) such as physiological data, biometric data, chemical data, biomechanical data, genetic data, genomic data, location data or other biological data from one or more targeted individuals. For example, some biosensors may measure, or provide information that can be converted into or derived from, biological data such as eye tracking data (e.g., pupillary response, movement, pupil diameter, EOG-related data), blood flow data and/or blood volume data (e.g., PPG data, pulse transit time, pulse arrival time), biological fluid data (e.g., analysis derived from blood, urine, saliva, sweat, cerebrospinal fluid), body composition data (e.g., bioelectrical impedance analysis, weight-based data including weight, body mass index, body fat data, bone mass data, protein data, basal metabolic rate, fat-free body weight, subcutaneous fat data, visceral fat data, body water data, metabolic age, skeletal muscle data, muscle mass data), pulse data, oxygenation data (e.g., SpO2), core body temperature data, galvanic skin response data, skin temperature data, perspiration data (e.g., rate, composition), blood pressure data (e.g., systolic, diastolic, MAP), glucose data (e.g., fluid balance I/O), hydration data (e.g., fluid balance I/O), heart-based data (e.g., heart rate, average HR, HR range, heart rate variability, HRV time domain, HRV frequency domain, autonomic tone, ECG-related data including PR, QRS, QT, RR intervals, echocardiogram data, thoracic electrical bioimpedance data, transthoracic electrical bioimpedance data), neurological data and other neurological-related data (e.g., EEG-related data), genetic-related data, genomic-related data, skeletal data, muscle data (e.g., EMG-related data including surface EMG, amplitude), respiratory data (e.g., respiratory rate, respiratory pattern, inspiration/expiration ratio, tidal volume, spirometry data), and the like. Some biosensors may detect biological data such as biomechanical data which may include, for example, angular velocity, joint paths, kinetic or kinematic loads, gait description, step count, or position or accelerations in various directions from which a subject's movements may be characterized. Some biosensors may gather biological data such as location and positional data (e.g., GPS, ultra-wideband RFID-based data; posture data), facial recognition data, audio data, kinesthetic data (e.g., physical pressure captured from a sensor located at the bottom of a shoe), or auditory data related to the one or more targeted individuals. Some biological sensors may be image or video-based and collect, provide and/or analyze video or other visual data (e.g., still or moving images, including video, MRIs, computed tomography scans, ultrasounds, echocardiograms, X-rays) upon which biological data can be detected, measured, monitored, observed, extrapolated, calculated, or computed (e.g., biomechanical movements or location-based information derived from video data, a fracture detected based on an X-Ray, or stress or a disease of a subject observed based on video or image-based visual analysis of a subject). Some biosensors may derive information from biological fluids such as blood (e.g., venous, capillary), saliva, urine, sweat, and the like including triglyceride levels, red blood cell count, white blood cell count, adrenocorticotropic hormone levels, hematocrit levels, platelet count, ABO/Rh blood typing, blood urea nitrogen levels, calcium levels, carbon dioxide levels, chloride levels, creatinine levels, glucose levels, hemoglobin A1c levels, lactate levels, sodium levels, potassium levels, bilirubin levels, alkaline phosphatase (ALP) levels, alanine transaminase (ALT) levels, and aspartate aminotransferase (AST) levels, albumin levels, total protein levels, prostate-specific antigen (PSA) levels, microalbuminuria levels, immunoglobulin A levels, folate levels, cortisol levels, amylase levels, lipase levels, gastrin levels, bicarbonate levels, iron levels, magnesium levels, uric acid levels, folic acid levels, vitamin B-12 levels, and the like. In a variation, some biosensors may collect biochemical data including acetylcholine data, dopamine data, norepinephrine data, serotonin data, GABA data, glutamate data, hormonal data, and the like. In addition to biological data related to one or more targeted individuals, some biosensors may measure non-biological data such as ambient temperature data, humidity data, elevation data, and barometric pressure data. In a refinement, one or more sensors provide biological data that include one or more calculations, computations, predictions, probabilities, possibilities, estimations, evaluations, inferences, determinations, deductions, observations, or forecasts that are derived, at least in part, from biosensor data. In another refinement, the one or more biosensors are capable of providing two or more types of data, at least one of which is biological data (e.g., heart rate data and VO2 data, muscle activity data and accelerometer data, VO2 data and elevation data).

In another refinement, the at least one sensor 18 and/or its one or more appendices thereof can be affixed to, in contact with, or send one or more electronic communications in relation to or derived from, one or more targeted subjects including the one or more targeted subjects' skin, eyeball, vital organ, muscle, hair, veins, biological fluid, blood vessels, tissue, or skeletal system, embedded in one or more targeted subjects, lodged or implanted in one or more targeted subjects, ingested by one or more targeted subjects, or integrated to comprise at least a portion of one or more targeted subjects. For example, a saliva sensor affixed to a tooth, a set of teeth, or an apparatus that is in contact with one or more teeth, a sensor that extracts DNA information derived from a targeted subject's biological fluid or hair, sensor that is wearable (e.g., on a human body), a sensor in a phone that is tracking a targeted individual's location information, a sensor affixed to or implanted in the targeted subject's brain that may detect brain signals from neurons, a sensor that is ingested by a targeted subject to track one or more biological functions, a sensor attached to, or integrated with, a machine (e.g., robot) that shares at least one characteristic with an animal (e.g., a robotic arm with an ability to perform one or more tasks similar to that of a human; a robot with an ability to process information similar to that of a human), and the like. Advantageously, the machine itself may be comprised of one or more sensors, and may be classified as both a sensor and a subject. In another refinement, the one or more sensors 18 are integrated into or as part of, affixed to, or embedded within, a textile, fabric, cloth, material, fixture, object, or apparatus that contacts or is in communication with a targeted individual either directly or via one or more intermediaries or interstitial items. Examples include a sensor attached to the skin via an adhesive, a sensor integrated into a watch or headset, a sensor integrated or embedded into a shirt or jersey, a sensor integrated into a steering wheel, a sensor integrated into a video game controller, a sensor integrated into a basketball that is in contact with the targeted subject's hands, a sensor integrated into a hockey stick or a hockey puck that is in intermittent contact with an intermediary being held by the targeted subject (e.g., hockey stick), a sensor integrated or embedded into the one or more handles or grips of a fitness machine (e.g., treadmill, bicycle, bench press), a sensor that is integrated within a robot (e.g., robotic arm) that is being controlled by the targeted individual, a sensor integrated or embedded into a shoe that may contact the targeted individual through the intermediary sock and adhesive tape wrapped around the targeted individual's ankle, and the like. In another refinement, one or more sensors may be interwoven into, embedded into, integrated with, or affixed to, a flooring or ground (e.g., artificial turf, grass, basketball floor, soccer field, a manufacturing/assembly-line floor), a seat/chair, helmet, a bed, an object that is in contact with the targeted subject either directly or via one or more intermediaries (e.g., a subject that is in contact with a sensor in a seat via a clothing intermediary), and the like. In another refinement, the sensor and/or its one or more appendices may be in contact with one or more particles or objects derived of the subject's body (e.g., tissue from an organ, hair from the subject) from which the one or more sensors derive, or provide information that can be converted into, biological data. In yet another refinement, one or more sensors may be optically-based (e.g., camera-based) and provide an output from which biological data can be detected, measured, monitored, observed, extracted, extrapolated, inferred, deducted, estimated, determined, calculated, or computed. In yet another refinement, one or more sensors may be light-based and use infrared technology (e.g., temperature sensor or heat sensor) to calculate the temperature of an individual or the relative heat of different parts of an individual.

In one variation, simulated animal data is generated by randomly sampling at least a portion of the set of real animal data. In another variation, real data is transformed into simulated data by adding a small random number to each value of a real data set. In this context, small means that the random number has a value within a predetermined percent of the number to which it is added. In a refinement, the predetermined value in preferential order is 1, 10, 20, 30, 40, or 50 percent of the value to which it is added. In a further refinement, the small random number has a mean of zero. In another variation, an offset value is added to each value of real animal data. In a still a further refinement, the offset value in preferential order 0.1, 0.5, 1, 2, 3, 5, or 10 percent of the value to which it is added. For this purpose, the random numbers used for random sampling can be uniformly distributed or normally (e.g., Gaussian random numbers) distributed.

In another variation, one or more simulations can be created on the fly based on past data and learning. In this regard, the simulated animal data can be transformed into a form that can be inputted into a simulation (e.g., a video game, simulated sporting event, simulated event for predicting or forecasting one or more biological events for purposes such as adjusting a health insurance premium) by a number of methods. In one refinement, real animal data is numerically modeled by fitting the real animal data to a function with one or more independent variables or one or more adjustable parameters that are optimized to provide a fit. In this context, such a fitted function is referred to as a model. In such data models, the one or more independent variables or parameters are inputted by the simulation to provide simulated data output. In this regard, time (t) is a useful independent variable that can be used to output a simulated biological output (e.g., physiological output) as a function of time in which a simulated individual is participating in a simulated event. In particular, biological parameters can be associated with a virtual participant in a simulation as a function of time.

Figure 2:
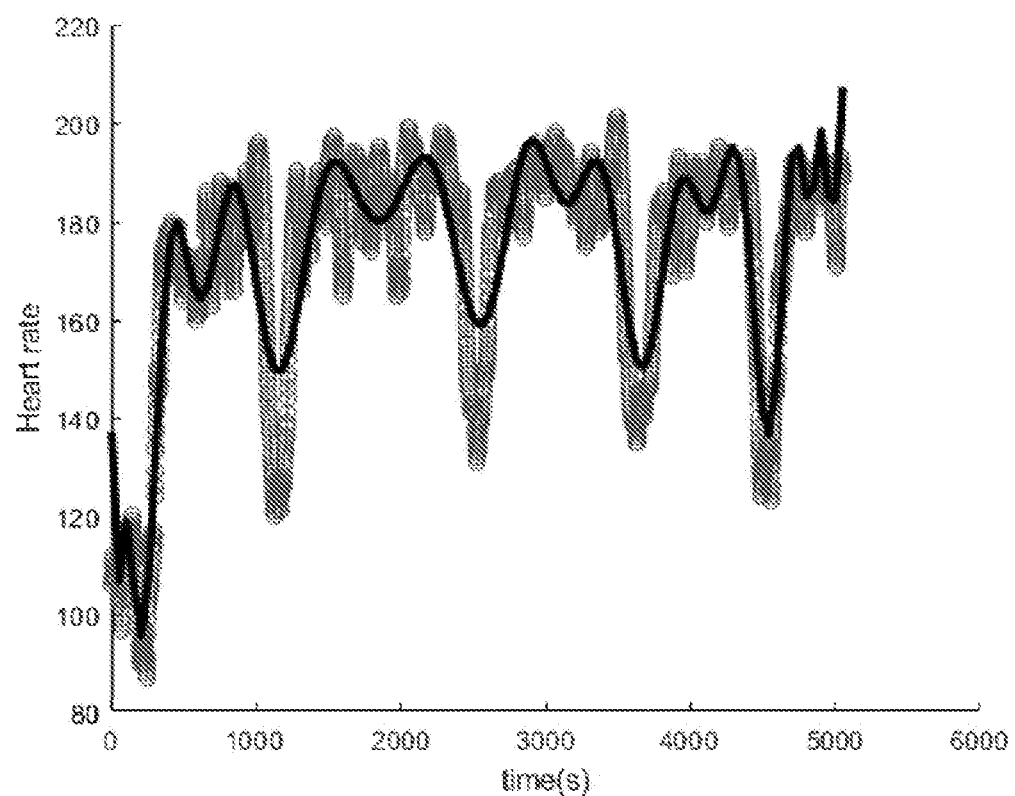
FIG. 2 is a plot of collected heart rate data along with a polynomial fit to the data.

In another variation, biological parameters for previously acquired real animal data from one or more targeted subjects can be approximated by a probability distribution. Examples of probability distributions include, but are not limited to Bernoulli distributions, uniform distributions, binomial distributions, normal distributions (i.e., Gaussian), Poisson distributions, exponential distributions, Lorentzian distributions, and the like. Typically, these probability distributions can be randomly sampled to assign one or more biological parameters (e.g., physiological parameters) to one or more simulated participants in a simulation. For example, biological parameters for previously acquired real animal data from one or more targeted subjects can be approximated by a gaussian distribution with the mean and standard deviation as adjustable parameters. The Gaussian distribution can then be randomly sampled to provide values for a simulation. Alternatively, the real animal data can be fit to any function (e.g., a line, polynomials, exponential, Lorentzian, piecewise linear or a spline between real data points, and the like) which is then applied by a simulation. In a refinement, the previously acquired real animal data can have one or more extrinsically associated parameters such as temperature, humidity, elevation, time, and other non-biological data, which can be applied as an independent variable or parameter in the one or more simulations. In another refinement, one or more biological parameters (e.g., heart rate, diastolic blood pressure, systolic blood pressure, perspiration rate, distance run, etc.) for a specified targeted individual can be, as a function of time while engaged in an activity, functionally modeled (e.g., fit to polynomials). In this latter example, a simulation can use the modelled function to provide values for the targeted individual as the simulation progresses in time. In this regard, the simulated data can be used to assess a biological occurrence (e.g., fatigue level) of participants in a simulation. For example, the running total for the amount of time a player has an elevated heart rate, diastolic blood pressure, systolic blood pressure, perspiration rate can be used as a measure of fatigue. FIG. 2 provides a plot of collected heart rate data along with a polynomial fit (polynomial order 60) to the data.

In a variation, artificial data sets can be generated, either randomly or otherwise, subject to one or more initiation parameters set by the user. This may be useful in the event real animal data a user desires cannot be acquired, captured, or created in a requested timeframe or manner. In the case where a user has requirements that may not make it feasible to acquire real animal data, simulation system 10 may create artificial animal data derived from at least a portion of real animal data or one or more derivatives thereof that conforms to the parameters established by the user, which may be made available for consumption. In this regard, the one or more parameters the data acquirer selects determines the scope of relevant real animal data that may be utilized as one or more inputs upon which the artificial data is generated, and/or to ensure that the artificial output generated meets the requirements desired by the acquirer. For example, a pharmaceutical company or research organization may want to acquire 10,000, two-hour ECG data sets from at least 10,000 unique males age 25-34 while sleeping from Sensor C and sampling rate settings of x, weighing 175-185 pounds with habits that include social smoking (15-20 cigarettes per week), at least one alcoholic drink 2-3 days per week, having a specific blood type with exhibited biological fluid-derived levels, and having a family medical history of diabetes and stroke. The simulation system may have, for example, 500 data sets from 500 unique males that match the minimum requirements of the requester, so the simulation system can create the other 9,500 data sets for 9,500 unique simulated males to fulfill the pharmaceutical company or research organization's request. To create the requested data sets, the simulation system may use the required parameters and randomly generate the artificial data sets (e.g., artificial ECG data sets) based on the 500 sets of real animal data. The new one or more artificial data sets may be created by application of one or more artificial intelligence techniques that will analyze previously captured data sets that match some or all of the characteristics required by the acquirer. The one or more artificial intelligence techniques (e.g., one or more trained neural networks, machine learning models) can recognize patterns in real data sets, be trained by the collected data to understand animal (e.g., human) biology and related profiles, be further trained by collected data to understand the impact of one or more parameters or variables on animal biology and related profiles, and create artificial data that factors in the one or more parameters or variables chosen by the acquirer in order to match or meet the minimum requirements of the acquirer. In a refinement, dissimilar data sets from similar individuals, or similar data sets from dissimilar individuals may also be utilized by the one or more artificial intelligence models for both model training and data generation purposes. In another refinement, a user chooses one or more parameters or variables for one or more simulations that utilize at least a portion of animal data, one or more simulations occur, and one or more users acquire at least a portion of the simulated data or one or more derivatives thereof for consideration (e.g., payment, other non-monetary value). For example, in the context of sports betting, the simulation system can be operable to offer bettors, bookmakers, or other relevant parties with an opportunity to acquire (e.g., purchase) one or more simulations utilizing at least a portion of collected animal data (e.g., the collected athlete sensor data) in order to predict one or more outcomes. Advantageously, such simulations can occur in real-time or near real-time. In another refinement, at least a portion of non-animal data is utilized as one or more parameters or variables in the one or more simulations. Additional details related to a Monetization System for Animal Data with particular applications to generating and monetizing simulated data derived from one or more animals are disclosed in U.S. Pat. No. 62/834,131 filed Apr. 15, 2019; U.S. Pat. No. 62/912,210 filed Oct. 8, 2019; and U.S. Pat. No. PCT/US20/28355 filed Apr. 15, 2020; the entire disclosures of which are hereby incorporated by reference. In one refinement, the data models set forth above can be used to create simulated data. In another refinement, simulated data can be created by the application of one or more artificial intelligence techniques (e.g., machine learning, deep learning) which can, for example, utilize one or more neural networks to analyze one or more previously captured or created data sets that match at least one of the characteristics required by the acquirer, the details of which are described herein. In this regard, the artificial intelligence-based engine recognizes one or more patterns or upper and lower limits in what is possible for a variety of scenarios in one or more real animal data sets and creates artificial data that matches or meets the minimum requirements of the user (e.g., the wagering entity, bettor, a pharmaceutical or healthcare provider seeking to acquire large amounts of data with specific characteristics, an insurance provider, etc.). The one or more data sets can be created based on a single individual, a group of one or more individuals with one or more similar characteristics, a random selection of one or more individuals within a defined group of one or more characteristics, a random selection of one or more characteristics within a defined group of one or more individuals, a defined selection of one or more individuals within a defined group of one or more characteristics, or a defined selection of one or more characteristics within a defined group of one or more individuals. In a refinement, a group can include a plurality of groups. Based on the user's requirements, the simulation system can isolate a single variable/parameter or multiple variables/parameters for repeatability in creating one or more artificial data sets in order to keep the data both relevant and random.

In a variation, one or more neural networks are utilized to generate simulated animal data. In general, a neural network generates simulated animal data after being trained with real animal data. Animal data (e.g., ECG signals, heart rate, biological fluid readings) is collected from one or more sensors from one or more target individuals typically as a time series of observations. Sequence prediction machine learning algorithms can be applied to predict possible animal data values based on collected data. The collected animal data values will be passed on to one or more models during the training phase of the neural network. The neural network utilized to model this non-linear data set will train itself based on established principles of the one or more neural networks. At least two distinct methodologies are described herein to generate artificial animal data from real animal data based on utilizing one or more trained neural networks. However, the present invention is not limited to the methodologies or types of neural networks utilized to generate artificial animal data from real animal data. In the first method, Long Short-Term Memory (LSTM) is used to generate simulated animal data. Long Short-Term Memory (LSTM) is a type of neural network that does not suffer from the shortcomings of Recurrent Neural Networks (RNN)(i.e., exploding/vanishing gradient). In the second method, a Generative Adversarial Network (GAN) is used to generate simulated animal data. Generative Adversarial Network (GAN) is a deep neural network architecture comprised of two neural networks, pitting one against the other (adversarial). Utilizing a GAN, the generator generates one or more new data values, which may comprise one or more new data sets, while the discriminator evaluates the one or more new values based on one or more user-defined criteria to certify, validate, or authenticate the newly created values.

Figure 3A:
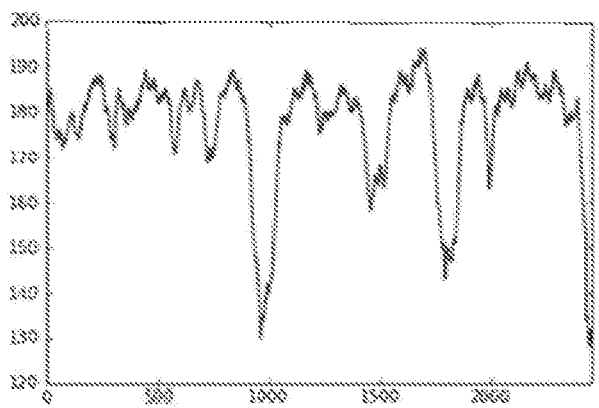
FIG. 3A provides a graph of heart rate beats per minute (BPM) values captured from a targeted subject in an athletic competition.
Figure 3B:
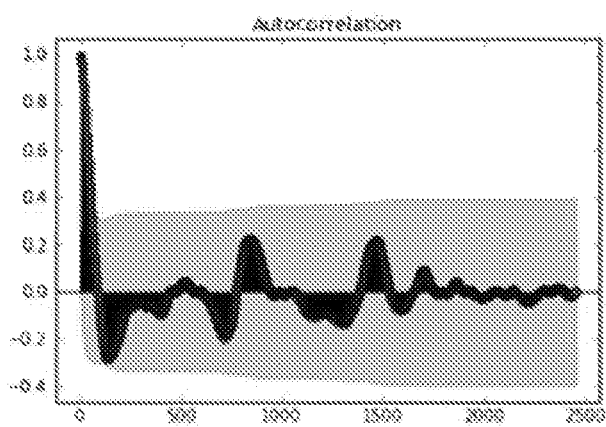
FIG. 3B provides the autocorrelation function for the data in FIG. 3A.

Prior to defining or designing the model and associating one or more neural networks, the first step is to evaluate the data and determine what relevant characteristics are exhibited within the data. There are numerous relevant animal data characteristics that can be inputted to train one or more neural networks. For example, in the case of ECG-based data, there are multiple characteristics that may be relevant, including Time Series, Non-Linear Function, Auto-Regressive Behavior, and Thresholds. Thresholds involve generally accepted values or principles (e.g., it may be established that a male over 90 years old should contact their doctor if their heart rate reaches over 200 beats per minute, or that the age-based max heart rate for a 33-year old male is n beats per minute). FIG. 3A provides a graph of the heart rate beats per minute (BPM) captured from a professional athlete, while FIG. 3B provides the autocorrelation function for the data in FIG. 3A.

Figure 4:
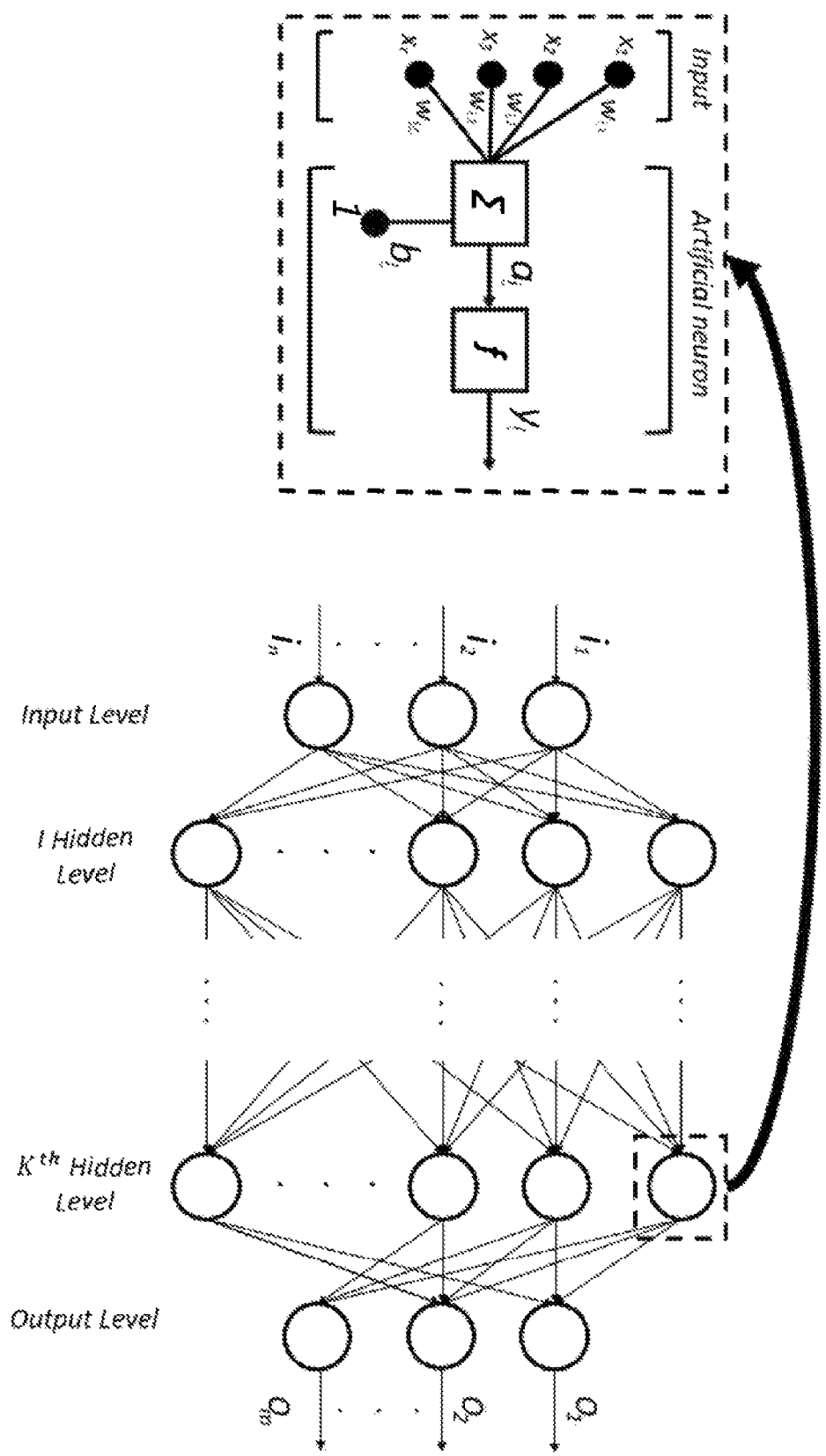
FIG. 4 provides an overview of a neural network that can be used in neural network architectures for generating simulated data.

FIG. 4 provides an overview of a neural network that can be used in neural network architectures for generating simulated data. Neural networks are proven to be a universal function approximator (i.e., can model any non-linear function). Neural networks pass an input, like an image, through multiple layers of digital neurons. Each layer reveals additional features of the input. A network's architecture—how many neurons and layers it has and how they are connected—determines the kind of tasks that the network will be good at. When data is fed into a network, each artificial neuron that fires transmits signals to certain neurons in the next layer, which are likely to fire if a plurality of signals is received. This process reveals abstract information about the input. A shallow network has few layers, but many neurons per layer. These types of networks are intensive from a computational standpoint. A deep network has many layers and relatively few neurons per layer. It can achieve high levels of abstraction using relatively few neurons. Each neuron activates based on the following rule:

$$Y=f(Wx+b)$$

wherein:
 $f$ is the activation function;
 W is the weight matrix;
 x is the input vector;
 b is the bias; and
 Y is the output vector.

As is known in the neural network art, the weight matrix is updated by a process called backpropagation where the gradient of the error between the predicted output and expected output with respect to the weights is used to update the weights at each neuron based on a learning rate in the direction of the decreasing gradient.

Figure 5:
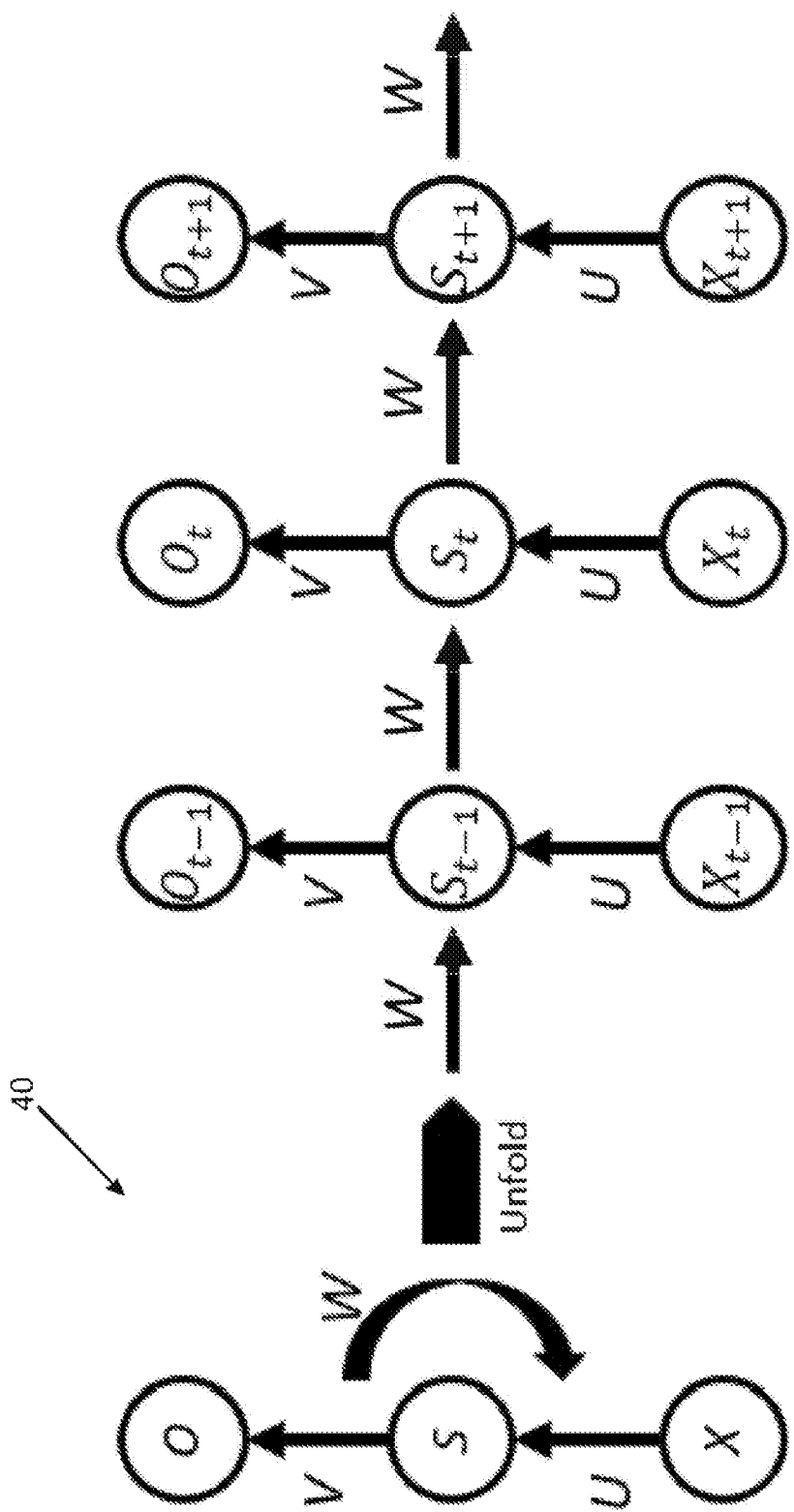
FIG. 5 provides details of a recurrent neural network that can be used for simulated animal data generation.

FIG. 5 provides details of a recurrent neural network that can be used for animal data generation. A recurrent neural network (RNN) is a class of neural networks where connections between nodes form a directed graph along a temporal sequence. This allows the neural network to exhibit temporal dynamic behavior. Unlike feedforward neural networks, RNNs can use their internal state (memory) to process sequences of inputs. They are designed to handle sequence prediction problems. RNN can keep track of arbitrary long-term dependencies in the input sequences. As depicted in FIG. 5, recurrent neural network 40 includes a base network 42 that is repeated a plurality of times i. Typically, i is chosen during the training phase of the RNN model such that it optimally preserves the required amount of history without adding computational complexity. This is usually achieved by training and testing the model with several possible values that are selected based on, amongst other things, patterns observed in the data, autocorrelation statistics, heuristics and domain specific knowledge of the modeler. In this figure, the inputs are labeled X which are weighted by the weight matrix U and provided to hidden layers S. W is the output from the hidden neuron layer S using a suitable activation function $f$. For a single hidden layer for at least the first hidden layer if there are multiple hidden layers, $W=f(UX+b)$ where b is the bias. In a refinement, the hidden layer component can include a plurality of hidden neuron layers. The output $W_j$ from a hidden layer j is provided to the corresponding hidden layer j in the next time step. Examples of suitable activation functions include but are not limited to sigmoid functions, tan h functions, ReLU, Leaky ReLU, and other activation functions known to those skilled in the art. In this network, outputs O are generated from the hidden neuron layer(s) S, e.g., $O=f(VW+b_2)$. After the RNN is trained, simulated data is generated by providing an input to the first cell (e.g., randomly generated). The output from this cell is then provided to the next cell as input, with this process repeated for each subsequent cell to generate a complete set of data.

Figure 6:
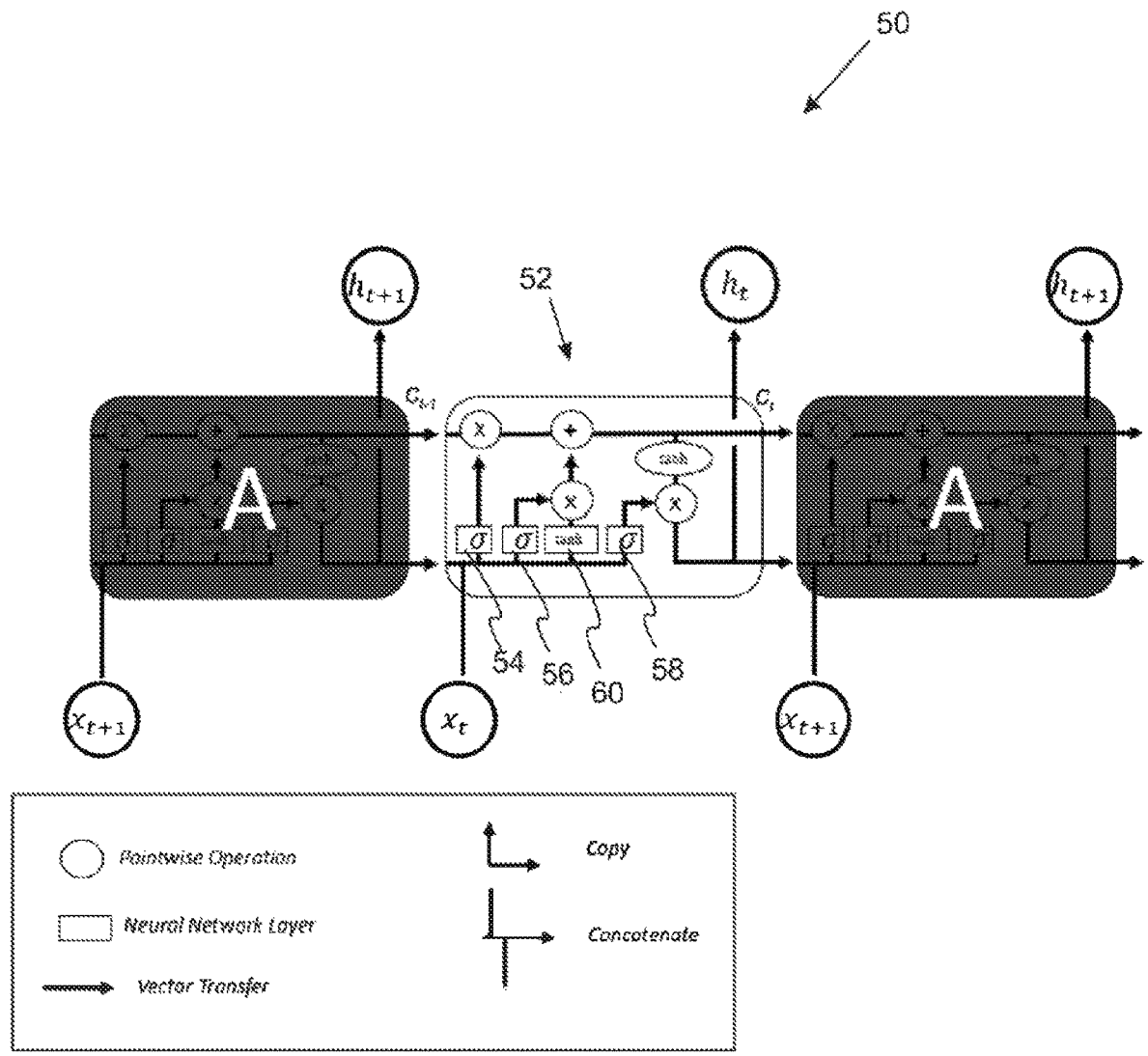
FIG. 6 provides a schematic of a Long Short-Term Memory (LSTM) network that can be used to generate simulated animal data.

The problem with standard RNNs is computational (or practical) in nature; when training a standard RNN using back-propagation, the gradients which are back-propagated can vanish (that is, they can tend to zero) or explode (that is, they can tend to infinity) because of the computations involved in the process which use finite-precision numbers. RNNs using LSTM units solve the vanishing gradient problem because LSTM units allow gradients also to flow unchanged. A common architecture is composed of a cell (the memory part of the LSTM unit) and three regulators (typically called gates) of the flow of information inside the LSTM unit: an input gate, an output gate, and a forget gate. FIG. 6 provides a schematic of an LSTM that can be used to generate simulated animal data. LSTM 50 includes recurrent cell 52. The recurrent cell includes forget gate layer 54, input gate layer 56, and the output gate layer 58, and a tan h gate layer 60. The outputs of these layers are provided by the following equations:

$$\begin{pmatrix} i \\ f \\ o \\ g \end{pmatrix} = \begin{pmatrix} \sigma \\ \sigma \\ \sigma \\ \tanh \end{pmatrix} W \begin{pmatrix} h_{t-3} \\ x_t \end{pmatrix}$$

wherein:
  i is the output of the input gate layer;
  $f$ is the output of the forget gate layer;
  is the output of the output gate layer;
  t is the current timestep;
  t−1 is the previous timestep;
  t+1 is the next timestep;
  g is the output of the tan h gate layer;
  W is the weight matrix;
  $x_t$ is the input vector (or value) at the t time step; and
  $h_t$ is a hidden state vector at the t−1 timestep;
  σ are sigmoid activation functions; and
  tan h is a tan h activation function.

The equations regarding the memory cell values $c_t$ are as follows:

$$c_t = f * c_{t-1} + i * g$$

$$h_t = o * \tan h(c_t)$$

For generating simulated data after the LSTM has been trained, simulated data is generated by providing an input (e.g., randomly generated) to the first LSTM cell, the hidden state generated from this cell is then provided to a trained neuron layer (e.g., trained along with the LSTM cells) for generating the input value for the next cell. This process is repeated to generate a full set of simulated data. Table 1 provides example pseudocode for generating simulated animal data utilizing the LSTM method, one or more parameters of which may be adjustable.

TABLE 1

Pseudocode for the LSTM method

Step 1. Configure the network
  • Step 1a. Set Timesteps = nt {=10}
  • Step 1b. Set Optimizer = ADAM(learning rate = lr, beta = b) {lr = 0.002; b=0.5}
  • Step 1c. Set epochs = ne {=100}
  • Step 1d. Set batch size tor training = bs {=30}
  • Step 1e. Set input rows for test = rc {=1000}
Step 2. Load available animal data (e.g., ECG data)
  • Step 2a. Read available animal data from file to dataframe(table)
Step 3. Create LSTM Model
  • Step 3a. Create sequential LSTM model with input sequence = timesteps, nu units {nu=50}
  • Step 3b. Add output layer with Linear Activation for real-valued animal data output
  • Step 3c. Compile model and set Mean Squared Error (MSE) as loss function and ADAM optimizer
Step 4. Train Model
  • Step 4a. Read the data frame created above
  • Step 4b. Reshape the data
  • Step 4c. Create tuples of input sequences of length equal to timesteps, and 1 real-valued output (the animal data reading)
  • Step 4d. Apply standardization to the data ((X− mean)/std dev) to normalize values to [−1,1]
  • Step 4e. Fit data into the model
Step 5. Test Model
  • Step 5a. Pass normalized input of real animal data readings as sequence of length timesteps to predict next animal data reading
  • Step 5b. Drop the first animal data from previous sequence and append prediction to create next input
  • Step 5c. Pass next input to model to predict next reading
  • Step 5d. Observe output and Repeat In applying the RNN methods (including LSTM variants), animal data from multiple events (e.g., multiple sporting events; multiple biological monitoring sessions in an individual's daily activity which can include sleep, exercise, work, and the like) are used as the sample to train the neural network. The animal data readings are timestamped and occur at a predetermined time period (e.g., approximately every second). Initially, the model is trained using N such observations (length of LSTM sequence), which can be a few (e.g., 20), a couple hundred, thousands, millions, and more. The network is trained for N epochs (e.g., 100), using MSE (Mean Squared Error) as the error metric and the ADAM optimizer for implementation of the backward propagation (weight up-dates). For reference purposes, ADAM is an optimization algorithm that can be used instead of the classical stochastic gradient descent procedure to update network weights iterative based on training data. After training the data-specific model (and making the model intelligent), the model is then applied to create a prediction for the animal data. In this example using ECG-based data, the model predicts heart rate data, which the model then generates. The predicted animal data generated by the model (e.g., heart rate) is tested first in-sample and then out-of-sample. Sample refers to the data sample being used to fit the model. Once a user has a sample and fits a model on the sample, a user can use the model for forecasting. In-sample forecasting utilizes a subset of the available data to forecast values outside of the estimation period and compares them to the corresponding known or actual outcomes. By using in-sample forecasting, all artificial animal data generated by the neural network has been previously seen by the model. Therefore, if a user is forecasting for an observation that was part of the data sample, it is an in-sample forecast. With out-of-sample forecasting, the data generated by the neural network has never been seen by the model before. Therefore, if a user is forecasting for an observation that was not part of the data sample, it is an out-of-sample forecast.

Figure 7A:
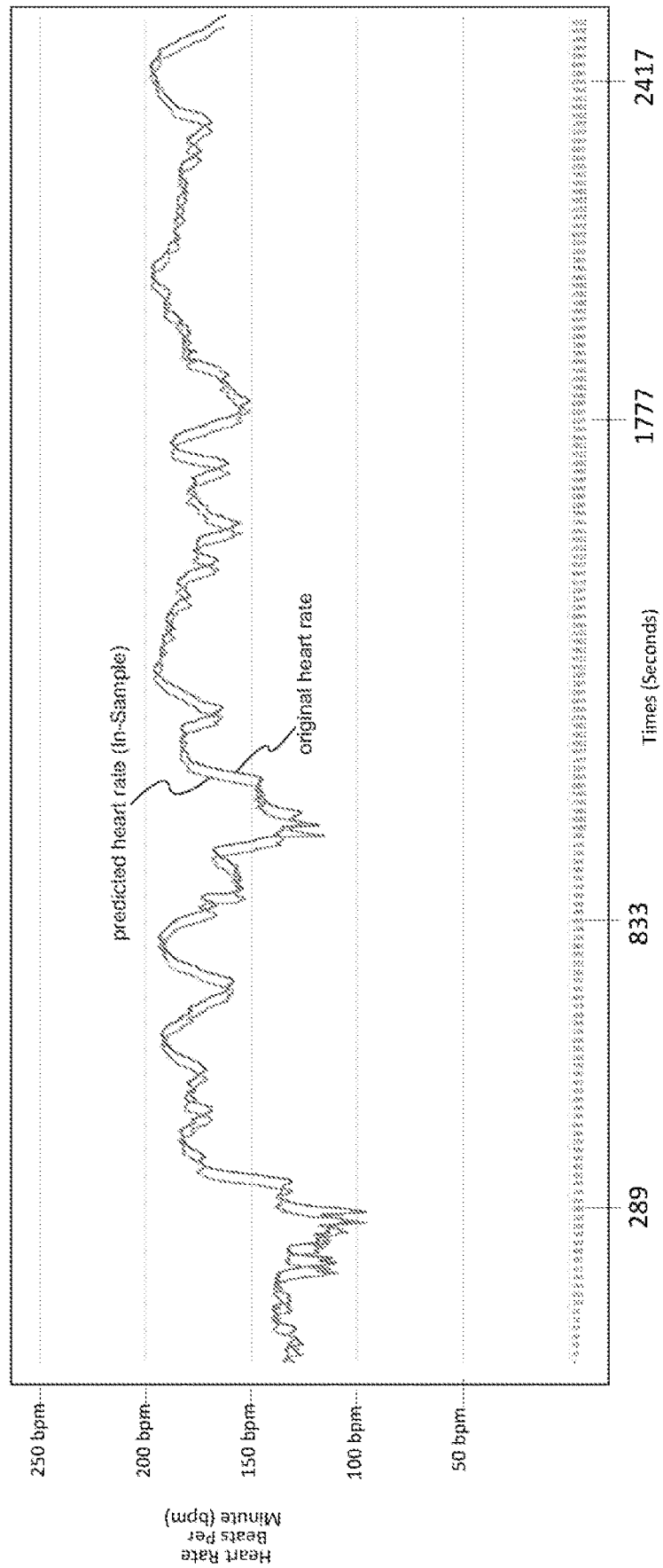
FIG. 7A provides a plot of artificial heart rate data generated from real animal data in-sample, which occurs when forecasting for an observation that includes at least a portion of the animal data sample.
Figure 7B:
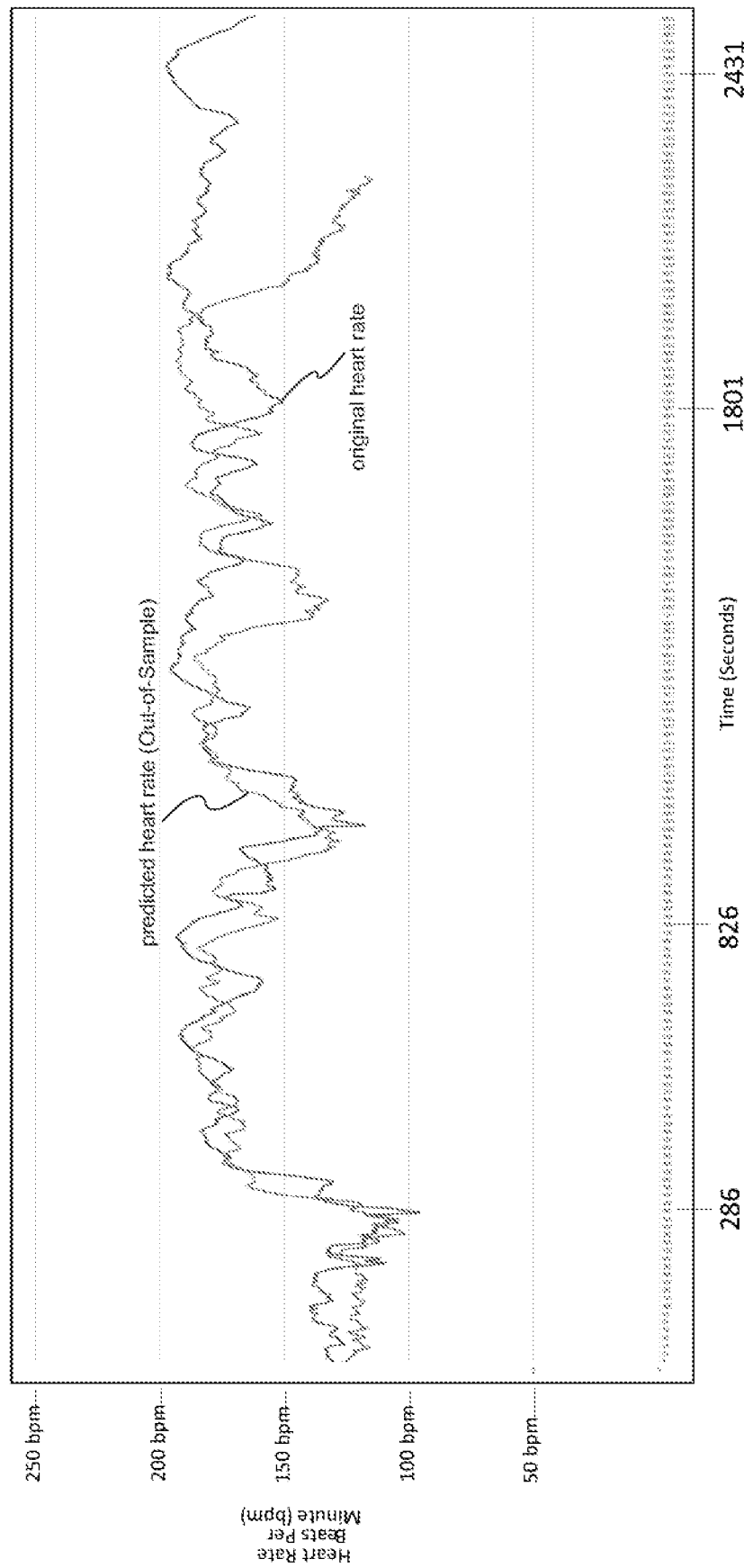
FIG. 7B provides an example of artificial heart rate data generated from real animal data out-of-sample corresponding to FIG. 7A.

FIGS. 7A and 7B provide plots that show simulated animal data generated using the LSTM method. The simulated animal data in FIGS. 7A and 7B is simulated heart rate data. Both Figures include artificially-created animal data (i.e., labeled "Predicted Heart Rate") generated based on real animal data (i.e., labeled "Original Heart Rate"). FIG. 7A provides in-sample, which occurs when forecasting for an observation includes at least a portion of the animal data sample. As mentioned above, by using in-sample forecasting, all artificial animal data generated by the neural network has been seen by the model previously. For example, if a user wants to generate artificial heart rate data for Athlete X based on his true heart rate characteristics (or at least a portion of his real heart rate data) to incorporate as part of a video game, the system would first train the model using Athlete X's previously captured real heart rate data and then generate Athlete X's artificial heart rate data (in-sample) using the model that was just trained. The artificial heart rate data generated would consist of previously seen values. FIG. 7B provides out-of-sample. In out-of-sample forecasting, the model is also trained with at least a portion of real animal data. However, unlike in-sample, the artificial animal data generated by the neural network has never been seen by the model before. This generated artificial animal data is completely new data and based on at least a portion of the real animal data. Out-of-sample forecasting includes generating new animal data for (1) a targeted subject from which the model has never seen the data from that particular subject based on one or more characteristics of the subject, and (2) a targeted subject from which the model has seen their/its animal data but with the introduction of one or more variations (e.g., changes, adjustments) to one or more parameters or variables that create new artificial data sets. Characteristically, out-of-sample data sets can be used for predictive use cases. For example, if Athlete X is playing in a real sports competition (e.g., match, game), and a user wants to predict what Athlete X's heart rate will be in the next 5 minutes, a user can use Athlete X's previously collected heart rate data sets from previous matches/games, as well as ancillary data sets associated with each heart rate data set that provide context to the one or more heart rate data sets, and the system would train the model utilizing the collected heart rate data and ancillary data to artificially create "the next 5 minutes" of heart rate data for Athlete X. In another example, if a model has only seen Athlete X's heart rate data when the on-field temperature is 90 degrees Fahrenheit, but the system is asking the model to generate heart rate data for Athlete X when the on-field temperature is 110 degrees Fahrenheit, out-of-sample forecasting would be used to generate Athlete X's artificial heart rate data based upon the adjustable temperature input (e.g., 110 degrees).

Figure 8:
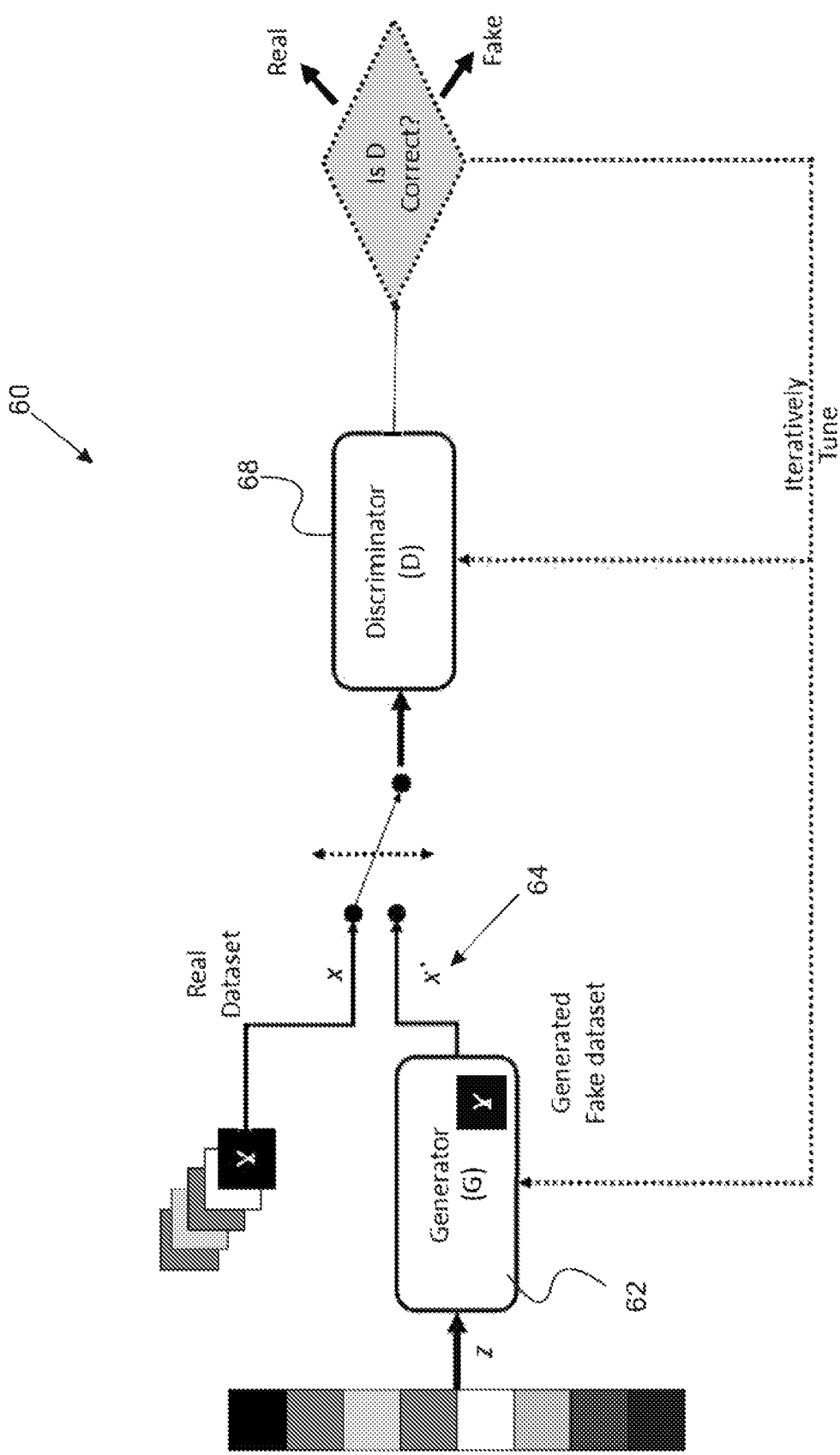
FIG. 8 illustrates a method for forming simulated animal data from a generative adversarial network (GAN).
Figure 9:
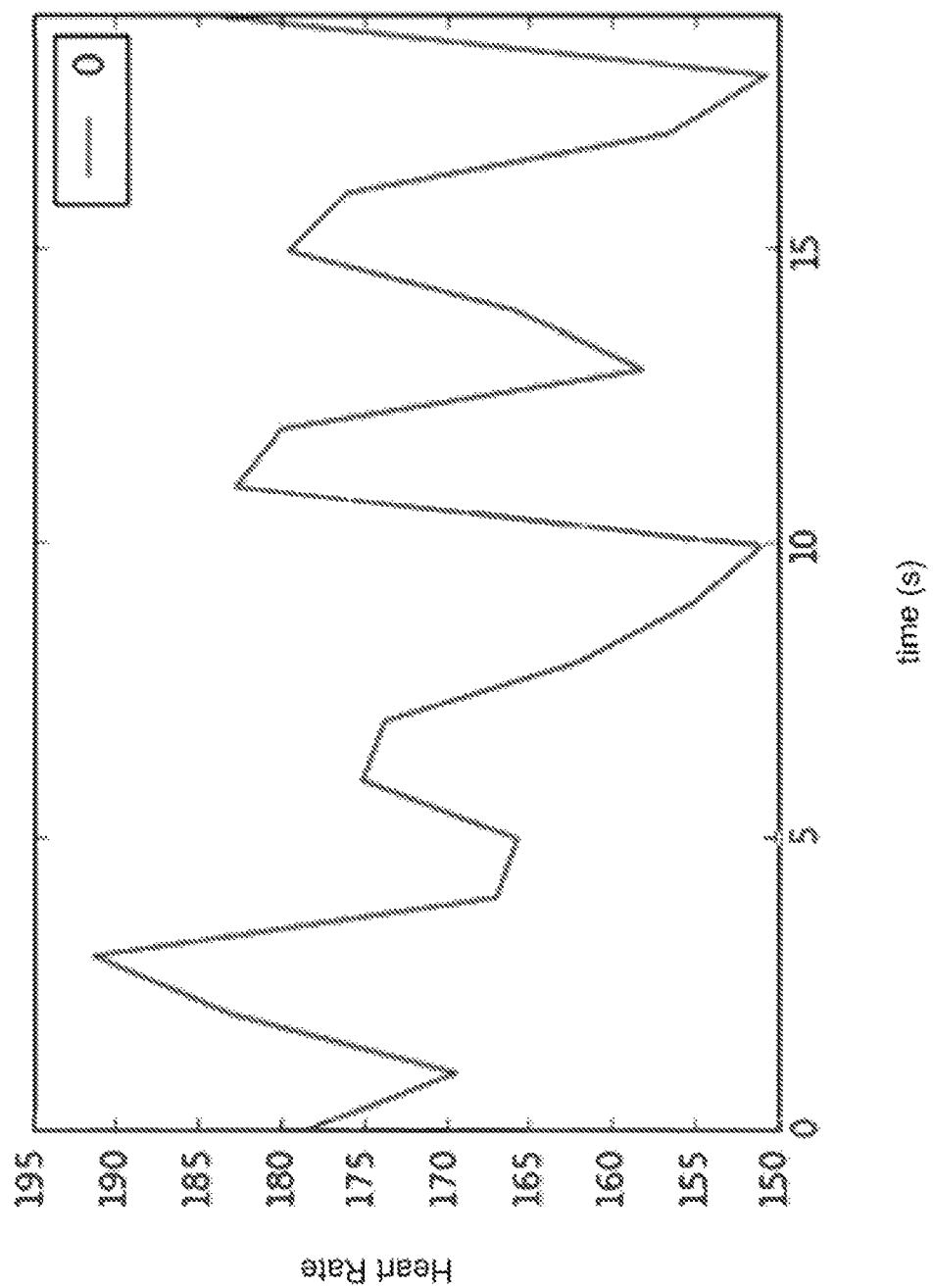
FIG. 9 is a plot of artificial heart rate data generated from real animal data using a generative adversarial network.

FIG. 8 illustrates a method for generating simulated animal data from a generative adversarial network (GAN). GANs are deep neural net architectures comprised of two neural nets, pitting one against the other (adversarial). GAN 60 includes the generator component 62 which generates one or more new data values 64 which may comprise one or more new data sets, while the discriminator component 68 evaluates the one or more new values based on one or more user-defined criteria to certify, validate, or authenticate the one or more new values. For example, the discriminator component 68 decides whether each instance of data that it reviews belongs to the actual training dataset or not. Discriminative algorithms try to classify input data (i.e., given the features of an observation of data, they predict a label to which that data belongs). Mathematically, the label is called y, and the features are called x. The discriminator is trying to predict y given, i.e., p(y|x) or the probability that the data belongs to a label given the features. The generative algorithm is trying to get the features or x. They capture p(x|y) or the probability of certain features given the label.

In this method, one or more animal data sets am utilized as the sample to train the Discriminator. The Discriminator is provided with an alternative data set (e.g., fake data or bad data) such that it can register the difference between one data set vs. another (e.g., real data vs. fake data, good data vs. bad data). For example, an application may use a GAN to train the neural network to differentiate whether an object is a specific type of food or not. In another example, a GAN may be utilized to determine whether the perspiration pattern of Athlete Y in a match played in 80 percent humidity and 95 degree environmental temperature is a valid generated data set or not by being trained with data related to the perspiration patterns of Athlete Y in 80 percent humidity and 95 degree environmental temperature. The user may determine the one or more characteristics (e.g., quantity, quality) of the one or more alternative data sets (e.g., fake data, bad data) it wants to provide to train the neural network. Characteristically, as the neural network obtains more data, the neural network may have the ability to determine the appropriate characteristic(s) required to train itself. In general, the more quality data the system has, the better the network will be. The Discriminator undertakes an evaluation process of the good data vs. the bad data. The Discriminator creates a feedback loop to learn the characteristics of the good and bad data to be able to evaluate why the good data is good, and why the bad data is bad. This enables the Discriminator to evaluate whether the animal data generated meets the threshold(s) established by the trained model as being true vs. not (in this example, ECG-based readings). The generator takes in one or more inputs (e.g., random numbers, constrained set of numbers) and generates a single value (e.g., a candidate ECG reading) which are evaluated by the Discriminator. Discriminator then feeds back the results into the Generator creating a learning feedback loop. For example, if the Generator generates three (3) consecutive heart rate values at 1× per second: 43 beats per minute (bpm), 45 beats per minute, and 300 beats per minute, the Discriminator will examine this pattern and determine that this heart rate pattern is invalid if the neural network has been trained to recognize that heart rate cannot increase from 45 to 300 bpm in a single second. When this occurs, the Generator will e-generate new values until the Discriminator "approves" the values generated by the Generator. In a refinement, the algorithm is adapted to a Time Series regression style problem for streaming animal data, but the basic idea of a GAN is applicable to create artificial animal data or predict animal data values.

FIG. 8 provides a plot that shows heart rate data generated using the GAN method. Table 2 provides example pseudocode to implement the GAN method for generating simulated animal data, one or more parameters of which may be adjustable.

TABLE 2

Pseudocode for the GAN method

Step 1. Configure the network
- Step 1a. Set Timesteps = nt {=10}
- Step 1b. Set Optimizer = ADAM(learning rate = lr, beta = b) {lr = 0.002; b=0.5}
- Step 1c. Set epochs = ne {=100}
- Step 1d. Set batch size for training = bs {=30}
- Step 1e. Set input rows for test = rc {=1000}

Step 2. Load available animal data (e.g., ECG data)
- Step 2a. Read available animal data from file to dataframe(table)

Step 3. Create Combined Model (GAN)
Step 3a. Build Discriminator:
- Step 3a.1. Build bi-directional LSTM (Long Short-Term Memory) Recurrent Neural Net
- Step 3a.2. Set sequence length = timesteps
- Step 3a.3. Create Hidden layer, Leaky ReLU activation
- Step 3a.4. Set Output layer activation to 'sigmoid'

Step 3b. Build Generator:
- Step 3b.1. Build bi-directional LSTM (Long Short-Term Memory) Recurrent Neural Net
- Step 3b.2. Set sequence length = timesteps
- Step 3b.3. Create Hidden layer, ReLU activation
- Step 3b.4. Set Output layer activation to 'linear'

Step 3c. Compile and set loss function to binary cross-entropy, measure loss for a two class classification error
Step 3d. Generator sample sequences from the generator for validity benchmark on the combined model
Step 3e. Set up the Discriminator by passing a valid input
Step 3f. Compile the combined_model, set loss function to binary cross-entropy Step 4. Train Model
- Step 4a. Read the data frame created above
- Step 4b. Repeat for a number of epochs
- Step 4c. Get batch sized input sequence of standard normals i.e. mean=0, variance=1
- Step 4d. Generate samples
- Step 4e. Randomly select batch_size samples from the input, real observation
- Step 4f. Train the discriminator
- Step 4g. Freeze weight of discriminator (set trainable to false)
- Step 4h. Get batch sized input sequence of standard normals i.e. mean=0, variance=1
- Step 4i. Add noise to the data
- Step 4j. Train combined model on batch
- Step 4k. Save discriminator loss and generator loss metrics
- Step 4l. Create tuples of input sequences of length equal to timesteps, and 1 real-valued output (the animal reading)
- Step 4m. Apply standardization to the data ((X- mean)/std dev) to normalize values to [-1,1]
- Step 4n. Fit data into the model Step 5. Test Model
- Step 5a. Generate sequence of standard normal random variables including noise
- Step 5b. Predict value using the combined model
- Step 5c. Inverse transform standardized predictions into scaled animal output In a refinement, the one or more trained neural networks utilized to generate simulated animal data consists of one or more of the following types of neural networks: Feedforward, Perceptron, Deep Feedforward, Radial Basis Network, Gated Recurrent Unit, Autoencoder (AE), Variational AE, Denoising AE, Sparse AE, Markov Chain, Hopfield Network, Boltzmann Machine, Restricted BM, Deep Belief Network, Deep Convolutional Network, Deconvolutional Network, Deep Convolutional Inverse Graphics Network, Liquid State Machine, Extreme Learning Machine, Echo State Network, Deep Residual Network, Kohenen Network, Support Vector Machine, Neural Turing Machine, Group Method of Data Handling, Probabilistic, Time delay, Convolutional, Deep Stacking Network, General Regression Neural Network, Self-Organizing Map, Learning Vector Quantization, Simple Recurrent, Reservoir Computing, Echo State, Bi-Directional, Hierarchal, Stochastic, Genetic Scale, Modular, Committee of Machines, Associative, Physical, Instantaneously Trained, Spiking, Regulatory Feedback, Neocognitron, Compound Hierarchical-Deep Models, Deep Predictive Coding Network, Multilayer Kernel Machine, Dynamic, Cascading, Neuro-Fuzzy, Compositional Pattern-Producing, Memory Networks, One-shot Associative Memory, Hierarchical Temporal Memory, Holographic Associative Memory, Semantic Hashing, Pointer Networks, or Encoder-Decoder Network. In a variation, a plurality of neural networks is utilized on at least a portion of the same animal data or one or more of its derivatives to create simulated data.

In each of the neural network methods, the data utilized by the model can include one or more adjustable parameters or variables that can create a more targeted artificial data set based upon the preference of the user. For example, in the context of professional sports, parameters or variables that a user may want to incorporate when creating a data set of a targeted subject's artificial heart rate data (e.g., in a basketball game) may include inputs such as body temperature, environmental temperature, distance run, biological fluid readings, hydration level, muscle fatigue, respiration rate, and the like. It may also include data that provides context to the biological data including traditional statistics (e.g., points, rebounds, assists, minutes played), in-game data (e.g., whether the player is on-court vs off-court, whether the player is playing offense vs defense, whether the player has the basketball vs not having the basketball, the player's location on the court at any given time, specific on-court movements at any given time, who the player is guarding on defense, who is guarding the player on offense), historical data (e.g., historical heart rate data, historical body temperature/distance run/biological fluid readings/hydration level/muscle fatigue/respiration rate data, a player's biological data sets against any given team, who the player guarded in any given game, who guarded the player in any given game, the player's biological readings guarding any given player, the player's biological readings being guarded by any given player, minutes played, the player's biological readings playing against any given offense or defense, minutes played, on-court locations and movements for any given game, traditional statistics, other in-game data), comparative data to similar and dissimilar players in similar and dissimilar situations (e.g., other player stats when guarding or being guarded by a specific player, playing against a specific team) injury data, recovery data (e.g., sleep data, rehabilitation data), training data (e.g., how the player performed in training in the days or weeks leading up to a game), nutrition data, a player's self-assessment data (e.g., how they're feeling physically, mentally, or emotionally), and the like. Other variables may also include age, weight, height, birthdate, race, nationality, habits, activities, genomic information, genetic information, medical history, family history, medication history, and the like. It should be appreciated that such parameters/variables are merely exemplary and not exhaustive.

Characteristically, animal data can provide context as to why one or more outcomes occur, as well as information related to what future one or more outcomes may occur. For example, in many cases, predictions are made with limited context and based on past performance (e.g., biological performance, performance of a task) without knowing what animal data drove past results. In the context of sports betting, analysis can be focused around historical statistical performance (e.g., individual statistics, team statistics), situational context on performance (e.g., venue, conditions, minutes played, past results vs opponent), and derived trends (e.g., Player C bats 0.274 with the bases loaded vs right handers on Team X). In many cases, the missing context related to captured data is what occurred (oftentimes biologically) with the one or more targeted individuals or groups of targeted individuals to drive (e.g., influence) past results. In this regard, animal data can provide the missing context, and simulated data can provide information related to what can or will occur next based upon the animal data and other variables or parameters. More specifically, the simulated data can provide context for future outcomes. For example, the simulation system may utilize information captured related to historical statistical performance, situational context on performance, and derived trends information and correlate this information with animal data to determine what drove these results and establish a baseline for any given individual or group of individuals. In a variation, the simulation system may utilize one or more targeted individual's historical animal data (e.g., heart rate, hydration data, biomechanical data, location data), the situational context information related to the animal data (e.g., was the player stressed when the result occurred? was the player dehydrated or nervous when the result occurred?), and one or more trends within the historical animal data state (e.g., player A misses shots outside of n feet y % of the time when his fatigue level is below z %), and correlate this information with non-biological information related to performance. Once a baseline as to what drove past results is established, the simulation system can interpret collected animal data readings by utilizing the baseline data to better understand why any given result has occurred. Advantageously, data collection and analysis can occur in real-time or near real-time. In a variation, the simulation system can run one or more simulations based upon the baseline data and the collected animal data (e.g., historical data, the real-time or near real-time animal data) to generate simulated data to predict future animal data related the one or more targeted individuals (e.g., the future heart rate data for an athlete for the $4^{th}$ quarter of a given sports competition). In some variations, the simulated animal data (e.g., future simulated heart rate data) generated by the simulation can be used as one or more inputs in one or more further simulations to predict an outcome (e.g., based on the athlete's future heart rate readings, the athlete will make the next shot/miss the next shot, win/lose the match, etc.). In a refinement, one or more artificial intelligence techniques can be utilized to correlate data sets to identify known biological-related issues from one or more targeted individuals or groups of targeted individuals, as well as identify hidden patterns within the one or more data sets to identify biological-related issues based upon the collected data. This may include finding entirely new patterns within data that has never previously been correlated with known issues, or finding new patterns amongst one or more data sets that may identify new issues. For example, collecting animal data, situational context information related to the animal data, and trends based on the real-time or near real-time animal data enables comparison of real-time or near real-time data to historical data in the situational equivalent while enabling evaluation of both microtrends (e.g., within seconds or minutes) and macrotrends (e.g., full game). Advantageously, one or more simulations may occur utilizing real-time or near real-time and/or historical animal data information to predict one or more occurrences related to one or more future animal data readings of one or more targeted individuals or groups of targeted individuals, and/or predict one or more outcomes.

In utilizing one or more of the methods previously described, the collection period of a previously collected or current real data set can be extended with simulated data. For example, simulation system 10 with access to a given quantity of in-play data for athlete A (e.g., 10 hours, 100 hours, 1000 hours, or more) and one or more other data types associated with Athlete A and matches Athlete A has played (e.g., in the context of a sport like tennis, elevation, on-court temperature, humidity, heart rate, miles run, swing speed, energy level, respiration rate, muscle activity, hydration levels, biological fluid-derived data, shot power, length of points, court positioning, opponent, opponent's performance in specific environmental conditions, winning percentage against opponent, winning % against opponent in similar environmental conditions, current match statistics, historical match statistics based on performance trends in the match) can extend a given data set using one or more artificial intelligence-based models to recreate data from a match in which the given athlete might not have even played or has yet to play (e.g., Player A has played a 2-hour, 3-set match with heart rate captured, but a user wants to know Player A's heart rate data for the $4^{th}$ set prior to the event occurring. Therefore, the simulation system will run one or more simulations to create the simulated animal data). More specifically, one or more neural networks may be trained with one or more biological and non-biological data sets associated with Athlete A to understand biological functions of Athlete A and how one or more variables can affect any given biological function. The neural network can be further trained to understand what outcome (or outcomes) occurred based on the one or more biological functions and the impact of the one or more variables. For example, upon being trained to understand information such as the one or more biological functions of Athlete A within any given scenario including the present scenario, the one or more variables that may impact the one or more biological functions of Athlete A within any given scenario including the present scenario, the one or more outcomes that have previously occurred in any given scenario including the present scenario based on the one or more biological functions exhibited by Athlete A and/or the one or more variables present, the one or more biological functions of athletes similar and dissimilar to Athlete A in any given scenario including scenarios similar to the present scenario, the one or more other variables that may impact the one or more biological functions of Athlete A in any given scenario including scenarios similar to the present scenario, the one or more variables that may impact the one or more biological functions of other athletes similar and dissimilar to Athlete A in any given scenario including scenarios similar to the present scenario, and the one or more outcomes that have previously occurred in any given scenario including scenarios similar to the present scenario based on the one or more biological functions exhibited by athletes similar and dissimilar to Athlete A and/or the associated one or more variables, an acquirer of data may request one or more simulations to be run to extend the current collected data set with artificially-generated data (e.g., Athlete A just played 2 hours with various biological data including location-based data captured. An acquirer wants location-based data for Athlete A for the 3rd hour of the match under the same match conditions prior to the 3rd hour of the match occurring, so the system may run one or more simulations to create the data based on previously collected data) or predict an outcome occurring for any given activity (e.g., the likelihood of Athlete A winning the match, or winning set #4, or any other outcome vs Athlete B, based on looking only at Athlete A's data). In a variation, the one or more neural networks may be trained with multiple animals (e.g., athletes), which may be on a team, in a group, or in competition with one another, and the one or more neural networks may be trained with one or more data sets from each animal to more accurately generate simulated data from which a predictive indicator to predict one or more outcomes can be derived (e.g., whether Athlete A will win the match vs Athlete B). In this example, the one or more simulations may be run to first generate artificial animal data based on real animal data for each athlete, and then utilize at least a portion of the generated artificial animal data in one or more further simulations to determine the likelihood of any given outcome and/or make a prediction.

In a variation, simulated animal data generated by any of the methods described herein can be transformed into a lookup table to be used by the simulation. In another variation, one or more inputs can be provided by a user or artificially created by the artificial intelligence-based model depending on the one or more user requirements, or what the artificial intelligence-based model selects.

In another variation, simulation system 10 provides one or more simulated data sets as an alternative to data sets generated from animals. In a refinement, one or more computing devices 12 and/or 30 create one or more insights, computed assets, or predictive indicators from at least a portion of the simulated data or one or more derivatives thereof. Advantageously, the simulated data can be used in an animal data prediction system, with a particular focus on wagering applications as well as probability assessment systems related to healthcare, telehealth, insurance, fitness, health/wellness monitoring, and the like. More specifically, the generated simulated animal data can be used either directly or indirectly: (1) as a market upon which one or more wagers are placed or accepted; (2) to create, modify, enhance, acquire, offer, or distribute one or more products; (3) to evaluate, calculate, derive, modify, enhance, or communicate one or more predictions, probabilities, or possibilities; (4) to formulate one or more strategies; (5) to take one or more actions; (6) to mitigate or prevent one or more risks; (7) as one or more signals or readings utilized in one or more simulations, computations, or analyses; (8) as part of one or more simulations, an output of which directly or indirectly engages with one or more users; (9) to recommend one or more actions; (10) as one or more core components or supplements to one or more mediums of consumption; (11) in one or more promotions; or (12) a combination thereof. In a refinement, the simulation system runs one or more simulations utilizing at least a portion of animal data, the one or more simulations occur, and simulated data is generated from which one or more products or services are created, modified, enhanced, acquired, offered, or distributed by the simulation system or another computing device. For example, the simulation system may also function as a sports betting platform (e.g., bookmaker) that offers one or more bet stimulation products based upon the generated simulated data (e.g., a prediction for the outcome of a sporting event based as least in part on the animal data) that a bettor can acquire (purchase) and utilize to place one or more bets (e.g., the simulation system may act as a bookmaker and offer an animal data-based prediction product generated from one or more simulations that reveal favorable odds and enable a user to acquire the product and place a bet within the same platform). In another example, the simulation system may accept one or more bets that utilize at least a portion of the generated simulated data (e.g., the simulation system acting as a bookmaker may offer or accept one or more bets based on a virtual horse race being operated by the simulation system; the simulation system acting as a bookmaker may offer or accept one or more bets on a real-world event based upon odds that it has adjusted utilizing the outcome of the one or more simulations). In another example, the simulation system acting may adjust the real time or near real-time odds it offers for any given bet based upon the one or more outcomes of the one or more simulations. Additional details related to an animal data prediction system utilizing simulated data are disclosed in U.S. Pat. No. 62/833,970 filed Apr. 15, 2019; U.S. Pat. No. 62/912,822 filed on Oct. 9, 2019; and U.S. Pat. No. PCT/US20/28313 filed Apr. 15, 2020, the entire disclosures of which are hereby incorporated by reference. Such simulated data sets can be derived from animal data and other data that may be utilized as one or more inputs. In a refinement, the one or more inputs includes user behaviors (e.g., in the context of sports betting, this can include one or more previous wagers or interactions with data; in the context of other scenarios such as insurance, it can include any behavior that can be recorded in a format that can be inputted in a simulation). Advantageously, an ability to change or modify one or more parameters or variables within one or more simulations, with at least one parameter or variable randomized, to provide one or more outcomes to a potential user can occur in real-time or near real-time. Example of such parameters include the adjustable parameters used to fit the real animal data to a function as set forth above. In the context of sports betting, an ability to run one more simulations utilizing data sets based on real animal data in real-time or near real-time can generate entirely new data sets from which the simulation system or third party system can either directly or indirectly: (1) offer or accept one or more wagers; (2) create, enhance, modify, acquire, offer, or distribute one or more products; (3) evaluate, calculate, derive, modify, enhance, or communicate one or more predictions, probabilities, or possibilities; (4) formulate one or more strategies; (5) take one or more actions; (6) mitigate or prevent one or more risks; (7) recommend one or more actions; (8) engage one or more users; or (9) a combination thereof.

In a refinement, simulated data that incorporates at least a portion of animal data may be utilized to enhance one or more insights, computed assets, or predictive indicators. For example, the simulation system 10 may derive a probability, or create a prediction, related to a certain outcome occurring based on historical data collected by the system (with historical data being inclusive of data collected in any current data set, e.g., real-time or near real-time data). By running one or more simulations using simulated data that incorporates at least a portion of animal data, the system can create, modify or enhance the predictive indicator to determine a more likely probability of an outcome occurring based upon different versions of the simulated data. Advantageously, the one or more simulations may occur in real-time or near real-time to provide a real-time or near real-time output. Different versions of the simulated data may have different adjustable parameters as set forth above, which have been determined by fitting real animal data. For example, in the context of a tennis match, one or more simulations may be run based on traditional statistics to determine whether a player will win or lose a match vs. other opponents. This may include head-to-head win/loss ratio, previous win/loss record, ranking, a player's performance in the tournament in previous years, a player's performance on court surface (e.g., grass, hard court, clay), and length of a player's previous matches. Analytics may become more granular within a match, including current match status of a tennis player (e.g., Player A is in Game 4 of Set 2 and is losing 6-4, 3-2), historical data (e.g., all of Player A match results when Player A is in Game 4 of Set 2 and is losing 6-4, 3-2, first serve percentage in second sets after playing n number of minutes, unforced errors percentage on the backhand side after hitting three consecutive topspin backhands). By incorporating animal-derived sensor data (e.g., calculating location data like distance run, physiological characteristics, biological fluid data, biomechanical movements) as well as factoring in other sensor data (e.g., humidity, elevation, and temperature for current conditions; humidity, elevation, and temperature for previous match conditions), entirely new artificial data sets can be created. For example, data related to a specific scenario may be generated that predicts how a player performs when the player's heart rate is above 190 bpm in Game 4 of Set 2, or how a player performs in Game 4 of Set 2 when: (1) the player's heart rate is above 190, (2) has ran more than 2.1 miles in the match, and (3) the on-court temperature is above 95 degrees. Outcome analytics may also become more granular, enabling determinations regarding whether a player will win % lose a given set, game, or even point vs another opponent based on the simulated data. Animal data provides context as to why outcomes occur for any given scenario, and the one or more simulations generate artificial data that enables one or more predictions to be based upon the added context. In this example, one or more simulations may occur to predict what a biological output may be for Player A during the match (e.g., their future heart rate and respiratory rate data), which can be utilized in a further one or more simulations to fine tune the insight, computed asset, or predictive indicator.

In a refinement, the simulation system is operable to run one or more simulations utilizing at least a portion of the one or more subjects' biological data to generate simulated data in order to predict the one more parameters, conditions, or requirements necessary to achieve optimal performance by one or more subjects. Optimal performance (e.g., for a given task; for biological functions) can include both physical performance and neurological performance. For example, a subject's mental state of being "in the zone" (e.g., flow state) may be predicted by utilizing one or more types of animal data derived from one or more sensors capturing information from the one or more targeted individuals (e.g., one or more combinations of biological data which may include, but is not limited to, heart rate data, ECG data, RR interval data, heart rate variability data (LF/HF ratio), pupil diameter data, respiration rate data, EEG data, EMG data, functional MRI data, motion data, glucose data, FFA metabolic data, motion pattern data, hormonal data such as glucocorticoid or HGH data, other biochemical data such as norepinephrine, cortisol levels and/or dopamine levels, and the like). Such biological information can be combined with one or more variables or parameters (e.g., situational context, environmental data, time, feelings of the subject, skills of the subject, output information such as the task the subject is performing, sleep, difficultly of the task relative to the skill of the subject, clarity of goals, risk, level of control perceived by the individual, and the like), one or more of which may be determined by a questionnaire or other medium that enables communication of information by the one or more individuals, to determine parameters for optimal performance state. For example, by looking at one or more biological parameters, associated variables, and the one or more outcomes associated with such parameters and variables, correlations can be created between the biological occurrences, the variables, and the outcome. Once an individual's baseline related to both biological data and conditions in which optimal performance state is achieved, the system can generate simulated data derived from biological data to predict future optimal performance states within any given set of variables/parameters in order to make one or more adjustments to keep an individual in their optimal performance state. Such optimization can occur for any subject-based performance including sports, healthcare, fitness/wellness, military, general business (e.g., employee wellness), and the like. In a variation, they system may utilize one or more artificial intelligence techniques to determine the optimal one or more variables/parameters in which the desired biological state (and its corresponding animal data readings) is attained. For example, once a targeted individual's baseline related to their optimal performance state—which includes their targeted animal data readings—is determined, the system can generate simulated data from collected animal data to predict the optimal set of variables/parameters required for the one or more targeted subjects to achieve their optimal performance state.

In another example, an elderly care facility may utilize at least a portion of the animal data collected from a targeted individual to run one or more simulations to determine a likely health outcome for the targeted individual, and therefore determine the amount of future care required for the targeted individual. Based on the amount of future care likely required, the facility may be able to create, modify, or enhance its pricing for each individual based on the individual's profile (e.g., personalized pricing). In such a scenario, one or more types of artificial animal data sets may first be generated for the targeted individual (e.g., a data set comprised of the targeted subject's future ECG readings for the next n years), from which one or more biological events can be predicted. Furthermore, based upon the simulated data, the facility may adjust its staffing level and skill to reflect the anticipated workload and requirement to care for the one or more targeted individuals. In some variations, the generated artificial animal data may be utilized in one or more further simulations to create and/or fine tune the predictive indicator (e.g., with a targeted subject's future ECG readings generated by the simulation system, the simulation system may run one or more simulations to determine the likelihood of a heart attack or stroke in the next m months). In another example, an automotive or aircraft manufacturer may want to run simulations to fine-tune the predictive indicator in order to provide one or more responses related to a targeted subject within the vehicle or aircraft to mitigate or prevent a risk. More specifically, an automotive manufacturer may want to determine whether someone that is exhibiting specific biological characteristics (e.g., physiological or biomechanical characteristics) while driving a vehicle may be at risk for causing an accident. By utilizing the animal data, which can include one or more derivatives thereof, the vehicle may take one or more actions (e.g., stop, pull over, self-drive to the hospital) based upon the predictive indicator derived from one or more simulations in order to mitigate or prevent a risk (e.g., the vehicle may drive itself to a hospital if it is determined that the person is having a heart attack based on collected sensor data; the vehicle may stop itself if it is determined that the likelihood of a person having a heart attack with a given profile and characteristics—a specific age, weight range, height range, heart condition, increased heart rate, elevated blood pressure, elevated stress level, irregular biomechanical movements—while holding onto the steering wheel and driving is greater than a predetermined threshold; or a more absolute prediction via the predictive indicator that the subject will have a heart attack with these given sets of characteristics and parameters). In another example, an airline may monitor the real-time biological characteristics of its one or more pilots via one or more source sensors while flying and take one or more actions (e.g., notify the airline, take control away from the pilot, put the plane on autopilot, enable control of the plane to the airline or airline manufacturer remotely) based upon the probability of an occurrence happening related to at least a portion of the animal data.

In another example, an insurance company may have a hypothesis related to an outcome for one or more persons that share one or more characteristics (e.g., height, weight, medical condition). An outcome may be, for example, the likelihood a person will succumb to a disease or a viral infection in the next n months, the likelihood a given injury will achieve a given recovery rate, the likelihood an individual may experience a medical episode (e.g., seizure, heart attack), and the like. To test its hypothesis, the insurance company may utilize at least a portion of the animal data to run one or more simulations via simulation system 10 to calculate a probability related to one or more occurrences happening and determine a likely outcome for those individuals. Based on one or more simulations, odds for any given outcome may be created, adjusted, or enhanced. In the insurance example, a premium may be adjusted, or a rate may be set based upon the likelihood of an outcome occurring. In a variation, animal data and one or more derivatives thereof including simulated data enables insurance companies to better understand the biological state of any given targeted subject or group of targeted subjects, as well as potential future occurrences. Animal data inclusive of simulated data can be used for a wide range of opportunities in the insurance industry including related to the creation, modification, enhancement, acquisition, offering, or distribution of one or more products or product categories, as well as personalization of such products (including personalized pricing). By utilizing at least a portion simulated data, insurance companies can identify personalized and group risk in a much more accurate and granular way, enabling creation or modification of products that are more micro (e.g., specific to an activity or group of activities) and more accessible (e.g., real-time or near real-time acquisition of such insurance products). In addition, animal data inclusive of simulated data enables one or more risk profiles to be created for any given targeted individual, group of targeted individuals, or targeted group(s) of individuals, enabling further product segmentation and pricing flexibility based upon any given risk associated with any given individual or group. Simulated data also enables insurance models to be more continuous (rather than fixed) with products being offered based upon a subject's biological readings and corresponding derivatives (e.g., predicted future biological readings), products being customized based upon the specific needs of the one or more subjects or group of subjects, and the like.

For a system related to insurance, a subject may have one or more sensors that collect animal data. The one or more devices may produce one or more signals or readings that enable the insurance company to monitor the subject's biological readings. Advantageously, simulated data may be generated from at least a portion of the collected animal data to provide one or more insights or predictive indicators related to a future occurrence (or likelihood of an occurrence) that enable the insurance company to take one or more actions (e.g., adjust a premium). The simulated data generated may be utilized to create, modify, or enhance a predictive indicator that can provide an insurance company with a subject's risk profile (e.g., their/its personal risk profile). Such simulated data may include one or more signals or readings from one or more non-animal data sources as one or more inputs in the one or more simulations (e.g., the activity the person is engaged in). Alternatively, one or more simulations may be run that incorporate the targeted subject's simulated animal data (e.g., future animal data readings) to generate a predictive indicator output related to a subject's personal risk (e.g., likelihood the targeted subject will experience any given medical event). The personal risk may be represented in a variety of ways such as a number or plurality of numbers (e.g., score or other indices) that an insurance company may use to assess any given subject.

Running one or more simulations can provide an insurance company with one or more forecasts, predictions, probabilities, possibilities, projections, or recommendations related to one or more outcomes for one or more future events that includes one or more targeted individuals, or one or more groups of targeted individuals. For example, one or more sensors may collect animal data information including heart rate data, ECG readings, oxygenation data, blood pressure data, weight data, body composition data, pulse data, biological fluid data (e.g., data readings derived from blood or urine), genetic data, and the like. One or more readings derived from the one or more sensors may be abnormal compared to similar and previous readings from the targeted individual or other individuals that share one or more comparable characteristics to the targeted individual (e.g., a baseline group that is similar in age, weight, height, social habits, medical history, and other physiological characteristics that the targeted individual is compared with). Ancillary information may be derived from the sensor data (e.g. specific habits or lifestyle choices) or included as part of the metadata (e.g., activities) based upon the one or more readings. This may indicate one or more health issues (e.g., illness, disease, infections, obesity issues, genetic mutations or derivations), lifestyle issues (e.g., drug use, tobacco use, alcohol abuse), activity issues (e.g., not enough exercise), and the like. Upon collecting the data, one or more simulations may be run to produce simulated data. The simulated data may be in the form of a predictive indicator (e.g., likelihood of any given medical event, disease, disability, death, recovery rates from any given illness, viral infection, bacterial infection, injury, and the like), or representative of future animal data under a predetermined set of conditions, which may be used on its own or in further simulations or models to create a predictive indicator. Based upon the collected animal data and the outputs of the one or more simulations, an insurer may take one or more actions, which may include adjusting one or more premiums for any given policy (e.g., which may occur in real-time and on a frequent basis as real-time or near-real time information is collected and/or generated), educate the subject on how it can improve any given health outcome in order to lower future costs for all parties (e.g., including one or more specific recommendations related to exercise, nutrition, habit changes), and the like. An insurer may also provide additional incentives based upon the animal data (e.g., bonus or penalty for achieving or not achieving any given animal data-related health target or sensor-related data target, alternative pricing options based upon frequency of animal data being shared, and the like). Advantageously, the simulation system's ability to collect animal data and/or provide simulated data, either or both of which may occur in real-time or near-real time, enables real-time or near-real time insurance applications.

In a variation, animal data and its derivatives (e.g., simulated animal data) can enable a more efficient and automated insurance underwriting process. Claims can be based, at least in part, upon captured animal data from one or more sensors as well as the derived simulated data (e.g., one or more sensors may capture irregular biological activity, from which information can be obtained related to the biological event that has occurred or is likely to occur in the future). One or more simulations may be run to determine the likely effect of one or more other biological processes or elements within the targeted subject. In such health monitoring scenarios, which may also be applicable to health & wellness applications as well as other biological tracking use cases, one or more communication intermediaries may be utilized (e.g., one or more unmanned aerial vehicles such as drones, high altitude pseudo satellites; an on-body transmission hub that acts as a collection and communication hub for sensors) to communicate with the one or more sensors directly on a continuous or intermittent basis in order to monitor the sensor data, as well as to assess the collected data via one or more simulations, the one or more subjects or group of subjects. Such communication intermediaries may also include one or more sensors to provide additional information related to the one or more targeted subjects (e.g., a drone that is deployed to the scene of an accident with an integrated camera that records video of the targeted subject and the accident scene while collecting data from a sensor located on the targeted subject). Continuous or intermittent data collection from sensors enables one or more simulations to occur, which can provide and interpret critical information related to any claim (e.g., what occurred to the subject, what is likely to occur based upon this occurrence, what is the likely cost of the claim, what is required to cover the claim, what is required to cover any future potential claim based upon current biological data).

In a refinement, at least a portion of the simulated data or one or more derivatives thereof are used to create or modify one or more insurance services, identifications, classifications, rates, reimbursements, or a combination thereof. In another refinement, one or more health classifications, treatments, procedures, identifications, rates, reimbursements, or services are created, modified, or assigned either directly or indirectly based upon at least a portion of the simulated data or one or more derivatives thereof. In a variation, at least a portion of the simulated data or one or more derivatives thereof are used to create, modify, or assign one or more health procedures, services, treatments, codes, identifications, classifications, rates, reimbursements, or a combination thereof.

In another variation, one or more simulations can be used to create or modify procedures, services, identifications, classifications, or rates (e.g., costs) associated with one or more codes related to the International Statistical Classification of Diseases and Related Health Problems (ICD), International Classification of Functioning, Disability and Health (ICF), International Classification of Health Interventions (ICHI), Current Procedural Terminology (CPT) for insurance and health applications (e.g., including remote patient monitoring, chronic care management, transitional care management, and the like), the Healthcare Common Procedure Coding System (HCPCS), and other similar systems. For example, in some variations, a patient is required to have a medical need to receive any given healthcare treatment. The medical need can be any diagnosis associated with the one or more individuals. In these situations, a diagnosis may receive an ICD code. An ICD code is a diagnosis code used to group and identify diseases, disorders, symptoms, adverse effects of drugs and chemicals, injuries, and the like. The CPT code defines the one or more treatments that are aligned with the diagnosis. Prior to receiving a treatment based on the diagnosis, one or more simulations may be run to evaluate one or more outcomes (e.g., to determine the probability related to the effectiveness of the treatment). Insurance providers and healthcare providers may enter into one or more agreements to determine how many simulations to run, relevant data to be used, rates related to how much to reimburse for simulations related to CPT codes, creation of new CPT codes based upon simulated data and the value it provides, and the like. Rates can be influenced by one or more parameters including the number of simulations run (e.g., 1 simulation vs 10,000), the number of targeted subjects, the quality of sensor data, and the like. In a refinement, the output of the one or more simulations that utilize at least a portion of animal data may dictate the type of treatment recommended or prescribed, the length of treatment, animal data targets (e.g., including goals, thresholds) during treatment (e.g., targets or goals related to one or more readings of the targeted individual), and the like.

In a refinement, the simulation system is a remote health monitoring system. Characteristically, such a system may enable virtual medical check-ins (e.g., systems that can include audio, video, and sensor data from a patient) between the patient and their medical professional. Given that one or more reimbursements can be provided for health services and in particular remote health services (e.g., initial set up, patient education, time spent on collection and interpretation of health data that is generated by a patient remotely), the simulation system can provide entirely new value for the healthcare ecosystem. By a patient enabling the system to access their animal data in order to run one or more simulations, the simulation system can provide the medical professional with context related to any given symptom derived from the animal data, as well as potential future outcomes based on the one or more symptoms. Such information can save time and cost (both from a current and future health care standpoint). In a refinement, at least a portion of the simulated data can be used to create or modify one or more costs or reimbursements associated with one or more health services or procedures. For example, a reimbursement code such as HCPCS code G2012 in the United States, which provides organizations with reimbursements for virtual check-ins, may have its cost structure modified or adjusted based upon running one or more simulations, as well as the output of the one or more simulations (e.g., a reimbursement for providing a predictive indicator for one type of animal data such as heart rate may be different than providing multiple separate predictive indicators for multiple types of animal data or a predictive indicator that takes into account multiple types of animal data). In this example, entirely new cost structures, codes, procedures, services, identifications, classifications, and/or rates may also be created based upon the simulated data.

In another refinement, the simulated data can be utilized as part of one or more human connection applications or platforms (e.g., dating applications, social interaction applications such as Facebook, Instagram, or virtual-based social platforms, and the like) to create, adjust, or modify one or more predictions, probabilities, or possibilities related to one or more human connections. A human connection can be a romantic connection, a physical connection, a love connection, a friendship connection, a business connection, and the like. For example, a dating application may run one or more simulations utilizing captured animal data from two or more targeted individuals who have interacted with each other's profiles (e.g., photos, video, profile information, or other forms of engagement) to predict if the two or more targeted individuals are a potential romantic match. The simulation system can assess the one or more biological readings from the two or more targeted individuals at the time of visual engagement (e.g., physiological indicators captured from sensors such as elevated heart rate, neurochemical data, pupillary response or pupil diameter, and the like), and detect one or more variations in the one or more animal data readings that indicate an attraction to connect. The strength of the connection may be determined by establishing a baseline for each targeted individual coupled with the degree of variation in each of the one or more types of animal data compared with one or more other visual engagements. Based on variations in the one or more animal data readings, the simulation system can generate simulated data from which an insight (e.g., a score) can be created based upon the strength of the connection between the two or more parties. In a refinement, a user may purchase one or more simulations to determine the strength of the connection. In another refinement, a user who allows access to their data for the one or more simulations (e.g., a female subject) may receive a portion of the consideration for enabling the simulation system to access to their data (e.g., if one or more male subjects are interesting to know if there is a biological-based connection).

In another refinement, simulated data that incorporates at least a portion of animal data may be utilized to create one or more products (e.g., prop bets or markets for sports betting) for one or more simulated events. For example, in the context of a sports competition, if a system has collected Team A's heart rate data when playing against Team B in real sports competitions, as well as other "Team A vs. Team B"-based data (e.g., non-animal data-based results of previously played Team A vs. Team B competitions), the system can be operable to create one or more new bets that utilize at least a portion of previously collected data, inclusive of at least a portion of animal data, incorporated as part of one or more simulations (e.g., the bet could be "Is Team A's Average Max Heart Rate going to exceed 170 beats per minute for the duration of a match vs. Team B in 10,000 simulated matches", or "Is A going to win the match more than 80% of the time vs Team B in 10,000 simulated matches" when utilizing at least a portion of animal data for Team A and/or Team B as part of the one or more simulated matches). For purposes of the presently disclosed and claimed subject matter, "previously collected data" can also include "current data," which includes data currently being collected in a present scenario or data set (e.g., including real time or near-real time data collected in any present scenario). In another refinement, simulated data that incorporates at least a portion of animal data may be utilized to create one or more new products for one or more virtual/simulated events. For the purposes of the presently disclosed and claimed subject matter, virtual events (and subjects) can be used interchangeably with simulated events (and subjects), and vice versa, to describe applications for simulated data. References to virtual events or simulated events is meant to be exemplary and inclusive of all possible systems that can utilize artificial animal data. Products can include prop bets or productized information utilized as part of a wagering or risk mitigation strategy for virtual bets. For example, if the system has collected respiration rate for one or more real subjects (e.g., real horses) in one or more real races, the system could generate simulated data (e.g., simulated respiratory rate) for one or more simulated races based on the collected real-world respiration rate data that would represent (at least for modeling purposes) the respiration rate for real-world horses, enabling the system to create one or more prop bets or betting products for one or more virtual subjects (e.g., virtual horses) that utilizes at least a portion of the generated simulated animal data in one or more virtual races (e.g., the bet could be: "is the virtual horse's max respiration rate in the virtual race going to reach above Indicator X"; "is virtual horse Y going to have a higher max respiration rate than virtual horse Z"; "is virtual horse Z going to win the race" when at least a portion of the animal data or one or more derivatives thereof is utilized as part of the virtual race, or a simulated data indicator is utilized and derived from animal data). In a variation, the simulated data generated by the simulation system may not share the same one or more characteristics from which it was derived from. For example, in the case of generating artificial data (e.g., artificial respiration rate) for a virtual subject (e.g., virtual horse), the simulation may characterize and display the generated artificial respiration rate as another indicator (e.g., a color, another name such as "fatigue", and the like). In a further refinement, the one or more virtual subjects share at least one common characteristic to the one or more real subjects, and the virtual event shares at least one common characteristic to the event from which the real animal data was collected (e.g., horse Z ran in a real race, and a virtual horse Z is running in a virtual race, with at least one characteristic of the real horse and the event in the system. This characteristic may be, for example, respiration rate, and the event may be a horse race. Bet: "is the virtual horse Z's max respiration rate in the virtual race going to reach above Indicator X"). Subject characteristics could include one or more biological characteristics, physical characteristics, profile characteristics (e.g., same name, jersey number, team name, team colors), and the like. In another example, a simulation in which one or more subjects can participate (e.g., video game, virtual world video game) may create one or more wagers or products (e.g., in-game virtual products for purchase) related to the real animal data of the one or more users playing the game (e.g., utilizing real animal data of the user that is incorporated as part of the virtual video game, creating a reward in the game for the user who reaches a goal while utilizing simulated data that incorporates at least a portion of their animal data or other animal data within the game; enabling a user to purchase an artificial data-based virtual product that is generated, at least in part, from the animal data; creating a bet type or product based on the artificial animal data utilized in the video game). In yet another refinement, simulated data is created for a simulation (e.g., virtual event, video game) based upon at least a portion of the animal data, which may create one or more new values. For example, in the scenario above, a user may want to know the probability that Horse Z wins the race in a simulated event when its simulated respiration rate goes above Indicator X, and how often this occurs in any given simulated race. The system may utilize various data including at least a portion of animal data to generate the simulated data (e.g., respiration rate of real-world Horse Z collected from one or more source sensors for every available race; respiration rate of other similar horses racing in similar conditions from one or more source sensors if available; respiration rate of other similar horses racing in dissimilar conditions from one or more source sensors if available; respiration rate of other dissimilar horses racing in similar conditions from one or more source sensors if available; respiration rate of other dissimilar horses racing in dissimilar conditions from one or more source sensors if available; other comparative animal data (e.g., heart rate) collected from one or more source sensors of similar and dissimilar horses in similar and dissimilar conditions; simulated respiratory rate data generated from one or more simulated races; other factors collected in the real world that may be utilized as inputs for the simulated races—environmental conditions like weather or temperature, injuries, biological fluid data, location-based data such as speed and acceleration data, training data, and the like). The simulated animal data may be utilized in a further one or more simulations to create one or more probabilities or predictions related to virtual representation of Horse Z winning the virtual race. Based upon the information, a user may place a bet on the virtual horse race.

In another refinement, a simulated subject's data within a simulation system may be comprised of data from multiple real-world animals. For example, in the context of a horse race, if a simulation system is featuring heart rate for a virtual horse, the heart rate may be derived from multiple real-world horses which in the aggregate comprise the virtual horse.

In still another refinement, simulated data that incorporates at least one type of animal data may be utilized to create or adjust odds (e.g., betting lines) with more precision. For example, if a line is set for Player A vs Player B for a particular real-world match, the computing device may run one or more simulations using a variety of similar match conditions (e.g., on-court environmental data, current score, current statistics, previous win-loss records, previous head-to-head statistics) and as well as one or more animal data inputs (e.g., all Player A animal data vs Player B animal data, including current match data, historical Player A vs. Player B head-to-head animal data, all Player A and Player B animal data in similar environmental conditions, Player A and Player B pre-match training data, injury data, and the like) and simulated data inputs (e.g., Player A's simulated heart rate and associated physiological metrics for the rest of the match, Player B's simulated heart and associated physiological metrics for the rest of the match), enabling the system to determine the probability of an outcome with greater precision. In a variation, by utilizing one or more artificial intelligence techniques such as machine learning techniques, the system can analyze previously-collected and current data sets to create, modify, or enhance one or more probabilities, possibilities, or predictions. The one or more data sets may include at least a portion of simulated data. Given that machine learning-based systems are set up to learn from collected data rather than require explicit programmed instructions, its ability to search for and recognize patterns that may be hidden within one or more data sets enable machine learning-based systems to uncover insights from collected data that allow for predictions to be made. Advantageously, because machine learning-based systems use data to learn, it oftentimes takes an iterative approach to improve model prediction and accuracy as new data enters the system, as well as improvements to model prediction and accuracy derived from feedback provided from previous computations made by the system (which also enables production of reliable and repeatable results). In such a scenario, new animal data such as new biological sensor data entering the system from any given subject at any given time enables for new simulations to be run, and new correlations to be made, based upon a broader set of data. For example, with data that enters the system on a point-by-point basis (or shorter time period) for the match between Player A. and Player B, the simulation system may be able to more accurately predict future animal data readings, and correlate those readings with other data in the system to more accurately predict an outcome. In a variation, a probability or prediction may then be derived and utilized to create or adjust one or more odds, which can occur in real-time or near real-time.

In yet another refinement, simulated data is created for a simulation (e.g., a virtual event) based upon at least a portion of the animal data, which may create new value for a wagering system. For example, a user may want to know the probability that a virtual subject (e.g., virtual Horse #3) wins the virtual race in a simulation (which may feature real data from races ran by one or more equivalents of Horse #3 in the real world, which the aggregate real-world horse data from multiple horses may comprise the virtual Horse #3) when its virtual respiration rate is above Indicator X. The probability-based or predictive data sets may be packaged to create one or more new betting products that a user can acquire to formulate a strategy and/or place a bet on the virtual horse race. Similarly, an insurance company may want to know the probability of an occurrence happening to a specific group of targeted individuals (e.g., targeted individuals with a specific heart condition, or targeted individuals with one or more positive/negative social habits that impact their animal data readings) and may create products specifically tailored to such targeted individuals to lower their premiums. In another example, one or more artificial data sets created based on real animal data from a targeted subject (and in some variations real animal data from other subjects) can be modified using simulation system 10 to introduce deviations in the data corresponding to any given characteristic of the targeted subject (e.g., fatigue, rapid heart rate changes). With an ability to change, alter, or adjust one or more parameters or variables to generate modified data sets, one or more simulations can be run to see how the targeted subject will perform based on a change in the one or more parameters or variables (e.g., high-stress situations, high altitude environment, extremely high temperature, extreme motion or movement), with the simulation system 10 establishing the patterns between body metrics (e.g., heart rate, respiration, etc.), the one or more parameters/variables, and the likelihood of an occurrence happening (e.g., winning a particular match), enabling the simulation system to calculate one or more probabilities related to certain conditional scenarios (e.g., what-if scenarios) based on a change to any given parameter/variable. In a variation, the creation, adjustment, or enhancement of one or more products (e.g., wagers, insurance products, analytics packages for heath monitoring platforms) and/or odds can occur in real-time or near real-time based upon adjustments in simulated data as an event occurs. For example, in the context of sports, the simulation system can run one or more simulations of a current match between Player A and B with new data being entered into the system in real-time or near real-time for real-time or near-real-time simulations, which can provide a value or series of values upon which one or more probabilities, possibilities, or predictions related to any given outcome occurring or desired outcome can be assigned. If, for example, the outcome under analysis is "will Player A's Heart Rate reach 200 beats per minute in the current match" or "will Player A win the match vs Player B," the system can run one or more simulations utilizing at least a portion of collected animal data to create a probability or prediction related to the outcome occurring. Examples of simulations the system can run include (a) Player B wins the first set in a longer-than-expected duration, and Player A starts feeling stress based on heart-derived data: a user is interested in seeing the potential outcomes for Player A in Set #2 based on collected data (current and previously collected animal and non-animal data); and (b) the environmental temperature increases 15 degrees from the beginning of the first set to the end of the first set of the match, and the heat begins to impact Player A's distance covered as Player A fatigue data indicates Player A is fatigued: a user is interested in seeing how far Player A is expected to run based on their current fatigue level, expected fatigue level based on possible match outcomes, current environmental temperature, and expected environmental temperature during the course of the match. There can be n number of such simulation scenarios, and additionally, there can be one or more simulation scenarios created on the fly by the system's artificial intelligence engine based on past similar matches. Once all these simulations are run, the output is collected and analyzed to provide a probability or prediction of the outcome under study.

In another method for creating one or more simulated data sets, previously captured data or previously created simulated data is re-run through one or more simulations to create the one or more new data sets. In this example, existing data (e.g., real animal data and simulated data) can be used as a baseline to determine the probability, possibility, or prediction related to a particular outcome via one or more simulations (e.g., a simulation ran n times—for example, 10,000 times—with the same one or more data inputs to determine the likelihood of an occurrence). In still another method for creating simulated data, one or more new variables or parameters can be applied to existing data to create new data sets. More specifically, existing data with one or more randomized variables is re-run through one or more simulations to create new data sets not previously seen by the system. For example, when the simulation system has data sets for a targeted individual (e.g., athlete) and a targeted event (e.g., a match the targeted individual played), the system can be operable to re-create and/or change one or more parameters or variables within the data set (e.g., the elevation, on-court temperature, humidity) and re-run the one or more events via one or more simulations to generate a targeted simulated data output. For example, in the context of tennis, an acquirer may want 1 hour of Player A's heart rate data when the temperature is at or above 95 degrees Fahrenheit for the entirety of a two-hour match. The system may have one or more sets of heart rate data at different temperatures (e.g., 85° F., 91° F., 78° F.) as well as inputs previously described in this application for a targeted individual like for Player A in similar conditions as well as other similar and dissimilar athletes in similar and dissimilar conditions. Heart rate data for Player A at or above 95 degrees has never been collected so the system can run one or more simulations to create the artificial data, and then utilize that data in one or more further simulations. In a refinement, the system can be operable to combine dissimilar data sets to create or re-create one or more new data sets. For example, a user may want 1 hour of Player A's heart rate data when the temperature is above 95 degrees for the entirety of a two-hour match for a specific tournament, where one or more features such as elevation or humidity may impact performance. While this data has never been collected in its entirety, different data sets that comprise at least a portion of the requested data and feature the one or more desired parameters/variables (e.g., one or more data sets from Player A featuring heart rate, one or more data sets from Player A featuring playing tennis in temperatures above 95 degrees, one or more data sets at the required tournament with requested features such as elevation) can be identified by the simulation system. With the simulation system operable to identify these requested parameters within the data sets and across data sets and be trained to understand the impact of the one or more parameters/variables on collected animal data and associated outcomes, the simulation system can run one or more simulations to create one or more new artificial data sets that fulfill the user's request (which may be, for example, a predictive indicator, computed asset, or artificial animal data) based on these dissimilar sets of data. In a variation, the dissimilar sets of data that are used to create or re-create one or more new data sets may feature one or more different subjects that share at least one common characteristic with the targeted subject (which can include, for example, age range, weight range, height range, sex, similar or dissimilar biological characteristics, habits, sensor readings, and the like). Using the example above, while heart rate data may be utilized for Player A, the system may utilize another one or more data sets from Players B, C, or D, which have been selected based upon its relevancy to the desired data set (e.g., some or all of the players may have demonstrated similar heart rate patterns to Player A; some or all of the players have similar biological fluid-derived readings to Player A; some or all have a very similar style of play to Player A; some or all of the players may have data sets collected by the system that feature tennis being played in temperatures above 95 degrees). These one or more data sets may act as one or more inputs within the one or more simulations to more accurately generate Player A's future biological readings (e.g., heart rate) under the desired conditions.

In still another method for simulated data, artificial data sets that are generic in nature (e.g., data set that lacks a predetermined selection of one or more desired biological characteristics) are created. In a variation, one or more randomized data sets are created, with the one or more variables selected by the system rather than the acquirer. This may be particularly useful if, for example, an insurance company is looking for a specific data set (e.g., 1,000,000 smokers) amongst a random sample (e.g., no defined age or medical history, which may be selected at random by the system), or if a wagering company is looking to create one or more new markets (e.g., prop bets) for events that never existed (e.g., prop bet around a video game simulation outcome). In a refinement, one or more artificial data sets are created based on a predetermined number of individuals picked by a given user of the system. In another refinement, one or more artificial data sets are created from a predetermined number of individuals picked at random by the system.

In a refinement, artificial data is assigned one or more tags based upon one or more characteristics from related animal data. A characteristic may include the one or more sources of the animal data, specific personal attributes of the one or more individuals or groups of individuals from which the animal data is derived (e.g., name, weight, height, corresponding identification or reference number), type of sensor used, sensor properties, classifications, specific sensor configurations, location, activity, data format, type of data, algorithms used, quality of the data, when the data was collected, associated organization, associated event (e.g., simulated, real world), latency information (e.g., speed at which the data is provided), and the like. It should be appreciated that any single characteristic related to animal data from which the simulated data is derived (e.g., including any characteristic related to the data, the one or more sensors, and the one or more targeted individuals) can be assigned or associated with one or more tags. Characteristically, the one or more tags associated with the animal data can contribute to creating or adjusting an associated value for the artificial data. In a refinement, one or more neural networks can be trained to assign one or more tags to one or more types of simulated data, as well as simulated data sets.

In another refinement, the simulated data may be assigned to one or more classifications. Classifications (e.g., including groups) can be created to simplify the search process for a data acquirer (e.g., as one or more searchable tags) and may be based on data collection processes, practices, quality, or associations, as well as targeted individual and simulated targeted individual characteristics. Classifications can be identifiers for data. For example, one or more classification may be assigned to an artificial data set that is derived from and/or representative of ECG data (with the one or more classifications including "Simulated ECG Data", "Targeted Individual Z's Simulated ECG Data", "Male Ages 25-34 Simulated ECG Data", "Simulated ECG Data from Sensor C", "Simulated ECG Data from n number of simulations", "Simulated ECG Data from Targeted Individuals on Team Y", "Simulated ECG Data from Game X", "Simulated ECG Data from Targeted Individuals on Team Y in Game X", and the like). Another classification may be assigned to an artificial data set that is representative of ECG data from a specific sensor with specific settings and following a specific data collection methodology. In another example, a classification may be created for data sets representing targeted individuals that have previously experienced a stroke, or for simulated data sets representing simulated targeted individuals that are based upon, at least in part, real-world targeted individuals. Examples of classifications or tags include metric classifications (e.g., properties of the simulated subject captured by the one or more sensors that can be assigned a numerical value such as heart rate, hydration, etc.), a simulated targeted individual's personal classifications (e.g., age, weight, height, medical history), a simulated targeted individual's insight classifications (e.g., "stress," "energy level," a score indicating the likelihood of one or more outcomes occurring), sensor classifications (e.g., sensor type, sensor brand, sampling rate, other sensor settings), simulated data property classifications (e.g., raw data or processed data), simulated data quality classifications (e.g., good data vs. bad data based upon defined criteria), simulated data timeliness classifications (e.g., providing data within milliseconds vs hours), simulated data context classifications (e.g., NBA finals game vs. NBA pre-season game), simulated data range classifications (providing a range for the data, e.g., bilirubin levels between 0.2-1.2 mg/dL), classifications associated with the simulation system (e.g., how many data sets has the one or more neural networks been trained with, types of neural networks utilized to generate simulated data), and the like. In a variation, one or more classifications may be assigned based upon what the artificial data represents, which may include one or more organizations, sensor types, sensor parameters, data types, data quality, timestamps, locations, activities, targeted individuals, groupings of targeted individuals, data readings, and the like. Characteristically, the one or more classifications associated with the animal data and/or the simulation system can contribute to creating or adjusting an associated value for the artificial data. In a refinement, one or more neural networks can be trained to assign one or more classifications to one or more simulated data sets.

In a variation, some classifications of simulated data can have a greater value than others. For example, simulated heart rate data from people ages 25-34 may have less value than simulated glucose data from people ages 25-34. A difference in value may be attributed to a variety of reasons including the scarcity of the data type used in the one or more simulations (e.g., on average, real glucose data may be harder to collect than real heart rate data and thus less readily available or collectable), the quality of real data coming from any given sensor to be used in the one or more simulations (e.g., one sensor may be providing better quality data than another sensor), the individual or individuals from which the real data comes from compared to any other given individual (e.g., an individual's data may be worth more than another individual's data based upon one or more unique characteristics of the individual, which may or may not be biological in nature), the type of real data (e.g., raw AFE data, from which ECG data can be derived, from a group of individuals with certain biological characteristics from Sensor X may have more value than only the derived ECG data from the same group of individuals with the same biological characteristics from the same Sensor X given that AFE data can provide opportunities for additional non-ECG insights to be derived including surface electromyography data), the derived use cases related to the data (e.g., glucose data can also be used to derive hydration information, which may be a more difficult data type to collect than heart-rate based data and therefore more valuable), the amount or volume of data (e.g., daily heart rate data from 100 people between the ages of 45-54 over the period of 1 year may have more value than daily heart rate data from the same 100 people between the ages of 45-54 over the period of 1 month), the context in which the data was collected (e.g., respiratory rate data collected from a targeted individual in a premier sporting competition compared to a training session, or respiratory rate data collected from a targeted individual with a life-threatening, infectious respiratory disease vs. when the targeted individual has no respiratory-related illness), and the like.

In a further refinement, the one or more classifications have one or more corresponding values that are created, assigned, modified, and/or enhanced by the simulation system. It should be appreciated that one or more classifications may have a predetermined value, an evolving or dynamic value, or a combination thereof. For example, a classification related to a given type of simulated data may increase in value as more relevant data is added to the simulation system, as more data within the classification is made available, or as demand increases for simulated data from data sets associated with the one or more specific classifications. Conversely, simulated data value may decrease in value as time passes from when the data was created (e.g., the value of simulated data to create a predictive indicator related to an outcome will likely have significantly more value prior to the outcome occurring rather than after the outcome has already occurred), the data has become less relevant (e.g., because new sensors capturing more accurate and precise information are available), or demand decreases for data from that specific classification. Multiples values may also be created, assigned, modified, and/or enhanced related to the same classification depending on the use case (e.g., in the case of sports betting, a classification in one market may have more or less value than the same classification in another market). In another refinement, one or more classifications may change dynamically with one or more new categories being created or modified based on one or more requirements or the input of new information or sources into the system. For example, a new type of sensor may be developed, a sensor may be updated with new firmware that provides the sensor with new settings and capabilities, or one or more new data types (e.g., biological fluid-derived data types) may be introduced into the system. In a refinement, one or more neural networks can be trained to create, assign, modify, and/or enhance one or more monetary-based and non-monetary based values to one or more animal data sets including one or more simulated data sets. In another refinement, one or more artificial intelligence techniques (e.g., machine learning, deep learning techniques) can be utilized to dynamically assign one or more classifications and/or values to one or more data sets.

A system for generating simulated data, as well as conducting one or more simulations utilizing at least a portion of animal data, has applications to a variety of industries. For example, in the context of real-world fitness or wellness systems, including personalized/group fitness classes (e.g., cycling, cross-fit, remote home fitness platforms), simulated data can be utilized to inform one or more users related to their real-time or near real-time biological state (e.g., physical status such as current or projected "energy level"), as well as provide insight into future outcomes that may occur based on one or more actions (e.g., based upon current animal data readings, historical animal data, and current activity of running at p miles per hour, targeted fitness individual X is projected to reach desired energy expenditure in n minutes and s seconds). Furthermore, simulation systems may be utilized to gamify fitness, wellness classes, enabling biological data to be integrated into the simulation game as well as enabling simulated data to be utilized within the game. In one example, one or more users may utilize one or more sensors to provide at least a portion of their animal data (e.g., heart rate data) to a simulation system to gain a competitive advantage or other consideration compared to other users within the class (e.g., the sensor data is transformed into a form to be inputted into a simulation, the simulation occurs with users participating in the simulation, the animal data incorporated in the simulation enables a benefit (e.g., monetary or non-monetary value) such as more rest period, free class-based on physiological-based success metrics within the simulation, or a free prize based on the most "energy" exerted in the class). Advantageously, at least a portion of the animal data is simulated data. Comparative biological metrics, which may include simulated metrics, may be visually displayed for each user in order to determine who is performing the best in any given class. In another example, one or more hardware components of a fitness machine (e.g., treadmill, cycling machine) or fitness display (e.g., a computing device that displays fitness content such as a television or interactive mirror) may communicate with one or more sensors on a subject to aggregate all sensor data into a single application, from which one or more simulations can be run to generate simulated data to communicate information related to a subject's current and future biological status, as well as generate one or more predictions or probabilities related to their animal data. In another example, a fitness machine with an integrated display or an interactive computing device streaming fitness content may collect biological sensor data and provide one or more biological insights derived from simulated data to its one or more users before a workout (e.g., providing predicted "fatigue" levels or expected caloric expenditure based on current biological readings, previously collected animal data, and projected duration and intensity of the given workout). In a refinement, a fitness instructor (e.g., real, virtual AI-based) or "smart" fitness equipment (e.g., equipment with one or more computing devices, or a computing device with a display featuring customized, AI-generated fitness content) may take one or more actions that can adjust the workout based upon the simulated data that is derived from the collected animal data (e.g., if the instructor or "smart" equipment projects that the targeted subject will not have exerted enough energy at the end of the workout based on current parameters and projected output, or is on pace to exert too much energy by the end of a workout based on the simulated data derived from the subject's data such heart rate or a derivative such as performance zone, the instructor or "smart" equipment may adjust the difficulty or speed in order to increase or decrease the difficulty of the workout for the user). The one or more actions may be derived, created, modified, or adjusted via one or more artificial intelligence techniques. In a refinement, one or more users may receive consideration (e.g., money, cryptocurrency, gift cards, free analytics, free classes) for allowing a third-party to access their animal data or one or more derivatives thereof (e.g., including simulated animal data that utilizes at least a portion of their animal data). Users may have the ability to opt-in or opt-out prior to, during, or after a workout.

In a refinement, artificial animal data for one or more simulation systems to engage users (e.g., virtual/simulated events, video games, simulators) is created. In one variation, computer software plays out events or occurrences including races, contests, studies, and the like. Advanced algorithms typically use a random number generator to determine the outcome. In a refinement, a neural network or plurality of neural networks can be utilized to determine an outcome. In some cases, they account for the skill of the participant(s) and conditions of the participant(s), as well as the luck elements inherent in real-world events (e.g., sporting events). Artificial animal data can be created by running one or more simulations based at least in part on real animal data. In another variation, computer software utilizes data derived from at least a portion of real animal data within a simulation system to enable a direct or indirect form of user engagement (e.g., participation) in the simulation. The one or more simulation systems can include game-based simulation systems (e.g., video game systems that simulate an event such as playing sports and enable user or multi-user participation; sports wagering simulators that enable users to place one or more bets on virtual events, such as betting on a virtual horse race; video game systems that enable an ability to acquire simulated data-related products within a simulation, such as simulated data-based virtual products available for purchase), simulators and other systems (e.g., military simulators, aviation simulators, and healthcare simulators utilizing virtual reality systems, augmented reality systems, mixed reality systems, extended reality systems), and the like. In a refinement, a game-based system engages one or more users via at least one of a virtual reality system, augmented reality system, mixed reality system, or extended reality system (e.g., a game-based military simulator that utilizes a virtual reality system). One or more users may engage with a simulation utilizing a variety of computing devices including traditional video gaming consoles, personal computers, mobile phones, tablets, terminals, virtual reality systems, augmented reality systems, and the like. The environment in which the user engages with a simulation system can include traditional video game environments (e.g., PC gaming, handheld gaming, mobile gaming, online console gaming, online gaming including web browser-based gaming), virtual reality systems, augmented reality systems, mixed reality systems, extended reality systems, and the like. Simulation systems that engage users may have one or more hardware components associated with the simulation system (e.g., game controller, game keyboard, game headset), as well as one or more biological sensors embedded within the hardware associated with the simulation system (e.g., game controller, game headset, game keyboard, seat sensor, camera sensor, other game sensors), or may utilize one or more sensors from the one or more users (e.g., smartwatch or on-body sensor capturing biological data) that are in communication with the simulation system and integrated as part of the simulation. Examples include hand and finger pressure sensors located within a simulation game controller (e.g., see how tight the controller is being held), ECG/heart rate sensors monitoring the heart rate of the player participating in the simulation game, EEG sensors located within a headset utilized as part of a simulation game, motion sensors embedded in the seat or controller of a player participating in the simulation game, sensors embedded within a bicycle to measure power output or wattage based upon peddle exertion as part of a simulation game, and sensors that measure reaction time of the player participating in the simulation game. Advantageously, direct communication between the one or more sensors and the simulation (e.g., video game) may occur via a web browser. Additional details related to a system that can communicate with sensors directly via a web browser are disclosed in U.S. patent Ser. No. 16/274,701 filed Feb. 13, 2019 and U.S. Pat. No. PCT/US20/18063 filed Feb. 13, 2020, the entire disclosures of which are hereby incorporated by reference. In a refinement, the simulation system may integrate and display one or more simulated readings derived from at least a portion of the one or more sensors gathering information from one or more users. For example, participants in a group fitness class may compete with each other in a simulation game, with one or more simulated readings derived from at least a portion of their animal data being incorporated within the game. In another example, a medical professional may see a display of a patient's real-time sensor data in an augmented reality system which may include simulated data that provides the real-time probability that a patient will experience a medical event while undergoing one or more procedures. In a variation, the simulation system may utilize simulated data (e.g., in the case of a medical professional, the medical professional's own derived simulated data, or the simulated data derived from one or more virtual patients) in order to train the one or more medical professionals to fine tune a skill or a plurality of skills. In yet another example, an insurance company may enable users to participate in a simulation game (e.g., utilizing one or more sensors within a simulation that provides a predictive indicator such as a personal risk score based upon the simulated data) that allows for simulated data to be derived from at least a portion of the user's sensor data, from which one or more premiums can be created, modified, or enhanced. In yet another example, a healthcare platform (e.g., telehealth application) may use a simulation system that utilizes simulated data derived from the patient's one or more sensor readings to enable virtual checkups or examinations, from which an outcome from the simulation can occur (e.g., the patient can receive a score or other indicator based on the simulated data generated from at least a portion of their animal data). Characteristically, the one or more simulated readings may include one or more non-animal data readings as one or more inputs. In another refinement, the video game or game-based system may create one or more new data types for the character or subject within the game based on at least a portion of the real sensor data or one or more derivatives thereof provided by the user. For example, a simulation game may create new indices for the in-game subject based on real-world sensor data captured, or insights derived from at least a portion of the animal data, like fatigue level, heart rate, reaction time, or controller pressure of a real-world subject. The simulated data utilized within the game may be animal data transformed into a form to be inputted into a simulation, or generated by running one or more simulations that utilize at least a portion of the real sensor data or one or more derivatives thereof to create the artificial data. Providing one or more readings to a simulation system (e.g., video game or game-based system), as well as generating artificial data, can all occur in real-time or near real-time.

Figure 10:
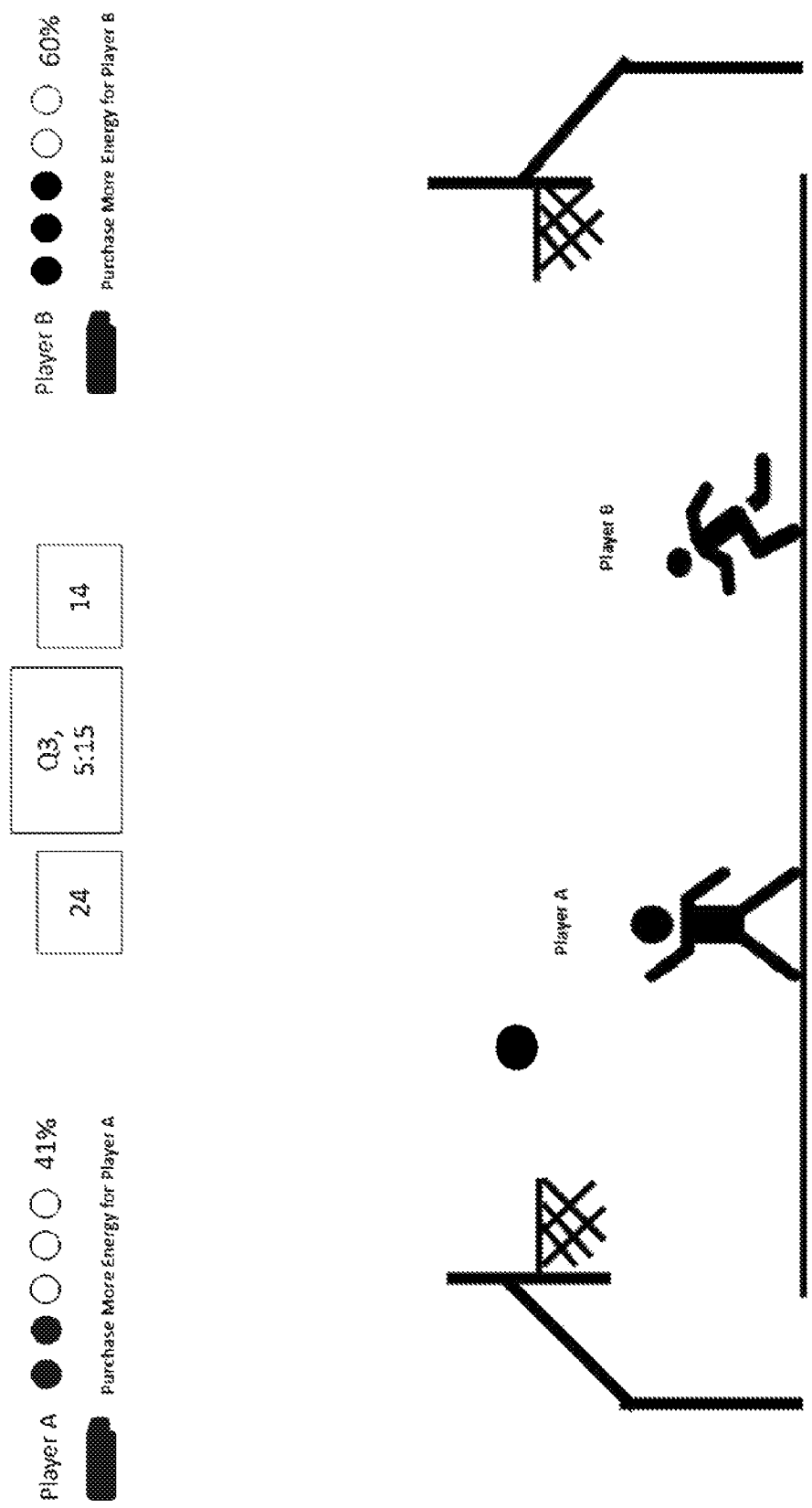
FIG. 10 illustrates one example of a gaming system (e.g., video game system) whereby a user can purchase a derivative of animal data.

In a variation, the simulation system-based data, which may be derived from one or more simulations and/or created artificially based upon at least a portion of the animal data, can be related to or associated with the one or more characters (e.g., animals) featured as part of the simulation (e.g., game). The characters may be based on animals that exist in real life (e.g., a professional soccer athlete in the real world may have a character that portrays that particular professional soccer athlete in a soccer video game) or artificially created, which may be based on, or share, one or more characteristics of one or more real animals (e.g., a simulated soccer player within a game may share a jersey number, a jersey color, or recognizable biological feature as a human soccer player). The system may enable a user of a game-based system (e.g., video game system) to purchase artificial data that utilizes at least a portion of real data within the game. In a refinement, the animal data purchased within the game may be artificial animal data, which may be based at least in part on real animal data and generated via one or more simulations, or transformed animal data that is in a form capable of being inputted into a simulation (e.g., a game). This data may be utilized, for example, as an index for an occurrence in the game. For example, a user playing a game may have the ability to play against a simulated version of a real-world athlete in a game utilizing the athlete's "real-world data," which may include the athlete's real-world biological data or one or more derivatives thereof transformed in a form capable of being inputted into a simulation. This may mean that, for example, the real-world athlete's "energy level" data that has been collected over time is integrated into the game. In one specific example, as the length of a match within a video game goes on, or the distance the simulated athlete within the video game has run, their "energy level" within the video game may be adjusted and impacted based upon a real athlete's collected real-world data. The real-world data may indicate the fatigue range of an athlete based on distance run or length of any given match. This information, in turn, can then be utilized by the simulation system to adjust the "energy level" within the game. This data may be utilized, for example, to gain an advantage within the game. In the context of a sports video game, the type of animal data that may be purchased within a game may include an ability to run faster, jump higher, have longer energy life, hit the ball farther, etc. FIG. 10 illustrates one example of a video game whereby a user can purchase a derivative of animal data (e.g., artificially generated animal data such as "energy level") based in part on real animal data to provide the user of the video game with an advantage (e.g., an increase in energy level, which provides a greater likelihood of winning the game). In another example, the in-game artificial data, which is derived from animal data and shares at least one characteristic with animal data, may also provide one or more special powers to the one or more subjects within the game, which may be derived from one or more simulations. In another refinement, a user may have the ability to purchase real-world animal data that is transformed into a form capable of being inputted into a simulation and incorporated into the simulation.

In a refinement, the simulation system converts at least a portion of the real animal data (e.g., physiological data) into artificial data that represents one or more insights, computed assets, or predictive indicators utilized within a game. The insight, computed asset, or predictive indicator is based upon the game's conversion of the animal data to artificial data transformed into a form capable of being inputted into a simulation, as well as the simulation system's interpretation of the data in a way that enables the simulation (e.g., game) to provide an advantage or disadvantage to one or more users (e.g., an "energy bar" provided in a right sports game that utilizes real-world sensor data to more accurately project fatigue for an animal such as a human). In order for conversion and interpretation to occur, the game run one or more simulations to determine the appropriate advantage or disadvantage provided.

In another refinement, artificial animal data which includes at least a portion of real animal data is provided to create one or more new markets (e.g., proposition bets/ wagers) for people to place one or more bets (including virtual bets), or as supplementary information related to one or more bets. For example, the one or more bets may be based on biological data (e.g., is Player A's heart rate in a live tennis match going to be above 180 bpm in the first set of Match X, which can be a proposition bet offered within any given wagering system), and artificial data can be utilized as supportive information for one or more real-world bets (e.g., one or more simulations can be conducted to predict the likelihood that Player A's heart rate will go above 180 bpm in the first set of Match X in n number of simulations). In another example, if the bet is "will player A win the match vs player B" in a live real-world match, one or more simulations using at least a portion of animal data can be run to create one or more probabilities or predictions related to one or more outcomes. In a variation, artificial data can be information upon which a bet is placed in one or more real-world events (e.g., is Player A's "energy level" going to reach below n percent in the first set of live Match X). In another variation, artificial data can be utilized as supportive information for one or more bets in a simulation (e.g., the bet "will player A win the match vs player B in the simulated match" can be supported by artificial data generated to provide probability-based information related to the outcome of the simulated match). In another variation, artificial data can be the one or more bets in the simulation (e.g., player A's simulated heart rate will go above 180 bpm in the first set of simulated match X). Advantageously, the one or more bets on artificial data may occur within one or more simulation systems (e.g., virtual reality, mixed reality, etc.). The one or more bets may be based on biological data (e.g., is Player A's heart rate in a live tennis match that is viewed within a virtual reality or augmented reality system going to be above 180 bpm in the first set of Match X, which can be a proposition bet offered within any given wagering system), or a derivative (e.g., is a virtual subject's simulated "energy level" in a soccer video game going to be go below 40% in the first half, with the simulated "energy level" being derived from at least a portion of the biological sensor data from a real player or subject and generated from one or more simulations). Simulated data generated from at least a portion of the biological sensor data provided directly to a system can also be used to understand the probability of an occurrence for any given outcome and provide one or more predictive indicators via one or more simulations. For example, a bettor may have an opportunity to purchase the simulated "energy level" of Player A for the last 10 minutes of a match within a real match or a simulation game (e.g., video game) to determine whether Player A will win the match (or win within the video game), with one or more simulations being run and one or more artificial intelligence techniques utilized to recognize patterns in data (e.g., machine learning techniques) to predict the outcome. Artificial data generated from at least a portion of the biological sensor data can also be used to influence the outcome of a particular bet (e.g., by providing an advantage or disadvantage to one or more users within the game) or occurrence within a simulation game. For example, a bettor can purchase more virtual "energy" for virtual player A within the video game to increase the likelihood of Player A winning the simulation game.

In a refinement, simulated data can be used within a simulation system (e.g., virtual reality system, extended reality system) as well as part of a simulation within the system. For example, in the context of healthcare, a virtual reality ("VR") system may be utilized to replicate real-life health care procedures. More specifically, a simulation system such as a VR system can provide a representation of a real healthcare scenario for a variety of use cases including practice, evaluation, learning, testing, or to gain understanding of biological systems, processes, or human actions. In this context, simulated animal data can be generated and incorporated by the system (e.g., to represent the one or more biological readings or vitals of the patient within the virtual reality system, which may include simulated ECG, respiratory rate, or biological fluid data), which may be changed or modified based on one or more actions of the user of the system (e.g., the doctor provides an injection of medicine to the virtual patient, and one or more biological readings such as the virtual patient's heart rate readings change). However, simulated data may also be incorporated to represent the biological data being derived by the user (e.g., transforming the user's animal data into a form that can be inputted into a simulation to display the user's sensor data readings. For example, the user/doctor in this scenario performing a surgery within the virtual reality system and displaying such indicators such as the doctor's "stress," "nervousness" based upon abnormal biomechanical movements such as head motion or hand tremors derived from one or more sensors which could be integrated in the object the one or more doctors are holding during the surgery, and the like). In another VR example, simulated data may be incorporated to demonstrate a future outcome. For example, the user (e.g., doctor) within a healthcare simulator may have predictive animal data-related outcomes derived from his/her animal data or the animal data of a virtual subject (e.g., patient) that is based at least in part on real animal data from one or more real-world subjects based on any given action, or potential action, taken within the system. In some cases, systems such as VR systems may include live operators operating the simulated systems, from which scenarios within the virtual reality system may be changed or modified. In such cases, the simulated animal data utilized within the simulation system may also be changed or modified based upon the changes or modifications made by the one or more operators. In a refinement, the one or more operators in a simulation system may be simulated operators as in the case of constructive simulations.

In another variation, animal data can be utilized to influence the outcome or gain a competitive advantage within a simulation (e.g., gaming) system. In this variation, the system integrates the user engaging with the simulation system (e.g., playing the video game) and their animal data (e.g., physiological data) into the game itself. More specifically, if a gaming system utilizes real-world people or characters that share one or more characteristics of one or more real-world people, the system could utilize at least a portion of the person's real-world animal data or artificial data, based in part on real animal data, to influence the outcome or provide the ability to influence the outcome through in-game purchases, acquisitions, or achievements of any simulated game played (e.g., sports video game, online virtual world game, group fitness competition). For example, if the user has an elevated real-world biological reading (e.g., stress level or has an elevated heart rate) comparative to other users who are also playing a similar game or relative to user's baseline biological reading, the one or more virtual subjects within the game may also experience similar data-related responses (e.g., high stress level, elevated heart rate) which may provide an advantage, disadvantage or other indication to the user and/or the one or more subjects in the game. Advantageously, this may occur in real-time or near real-time. The advantage, disadvantage, or other indication may be immediate and/or for a specific duration. Depending on the game, the advantage may include bonus points, extra strength, access to easier levels of resistance on the fitness equipment being utilized (for example, in a cycling class in which you are competing with other subjects), and the like. Disadvantages within the game may include points lost, a decrease in energy level, more resistance applied to the fitness equipment being utilized by the subject (for example, in a cycling class in which you are competing with other subjects, the bicycle pedals), and the like. Similarly, the indication of a user's various biological-based animal data readings may include a viewable portal that provides various biological-based animal data readings of the user within the game. Use cases include flight simulations, military simulators, medical simulators, high-frequency trading simulation programs that monitor how traders react in any given situation related to the financial markets, sports video games, fitness classes, wellness simulators (including behavioral health), and the like. As an example, if a user is playing a web browser-based shooting game, demonstrating real stress or an elevated heart rate may make the shooter zoom lens within the game less steady. In another example, a virtual body that a medical surgeon is practicing surgery on may provide an indicator (e.g., turn from one color to another) if the surgeon's heart rate, stress level, or biomechanical movements (e.g., hand) indicate an abnormality with the surgeon (e.g., the surgeon is stressed or has unsteady hands). On the other hand, showing peak biological activity (e.g., steady hands and steady heart rate) may provide the user and their corresponding virtual character or subject in the game (e.g., shooter) with an advantage within the game. These biological data-based animal readings (e.g., real-time heart rate) may be viewed by one or more opponents or third parties, upon which tactics may be created to put the opponent at a disadvantage (e.g., elevate the opponent's real-time heart rate and weaken the opponent in some way within the game), feedback may be provided, a reward or other consideration (e.g., monetary) may be given, etc. In one refinement, a controller with sensors embedded within a controller or non-controller based animal data sensors (e.g., smartwatch, on-body or implanted sensor, etc.) communicate with the game itself. In a further refinement, the communication between sensor and system occurs via a web browser. In another refinement, simulated data may be purchased based upon at least a portion of the sensor data collected by the video game or game-based system. As previously described, this data may be utilized, for example, to gain an advantage within the game. In the context of a sports video game, the type of artificial data based upon real sensor data that may be purchased within a game may include an ability to run faster, jump higher, have longer energy life, hit the ball farther, or an increase in energy level, which may provide a greater likelihood of winning the game. The type of simulated biological data provided may also include one or more special powers to the one or more subjects within the game, with the one or more special powers utilizing at least one related characteristic to the biological data, which may be derived from one or more simulations or generated from one or more statistical models or artificial intelligence techniques. Updates to simulated data within the game may be provided or derived in real-time or near real-time when the data is collected by the simulation system. In this variation, the stimulated animal data generated by the methods above can be provided to the simulation system.

In a variation, simulated data derived from a targeted subject's biological data can be utilized within a simulation to change, modify or enhance one or more other data types to inform one or more subjects. For example, in a health simulator, a system may utilize the simulated data derived from the targeted subject to forecast future biological readings for any given activity, from which other data (e.g., visual representation of a targeted subject) can be created, modified or enhanced. The derived simulated data may include inputs such as exercise plan, nutrition plan, and the like, as well as the targeted subject's animal data (including data sets collected via the one or more biosensors utilized by the targeted subject), and a current and/or altered visual representation of the targeted subject which may include the subject's body (e.g., an altered rendering of the subject's "targeted" future body via an avatar or other visual representation, which may be adjustable by the targeted subject). The output of the one or more simulations may include optimal exercise, nutrition, and daily lifestyle plans (e.g., including hours of sleep per night, social habits, and the like) based on at least a portion of the simulated animal data generated or one or more derivatives thereof, an altered visual representation of the targeted subject which may include the subject's body (e.g., an altered rendering of the subject's future body via an avatar or other visual representation n days later after following a specific exercise and diet plan using at least a portion of the simulated data), and the like.

In another variation, one or more users in a simulation (e.g., video game or game-based system) can include their own animal data as part of the game and compete against (1) other real-world subjects (e.g., humans that are professional sports athletes, fitness instructors, consumers looking to compare themselves with other consumers such as in a fitness challenge, gamers, and the like), or (2) virtual participants (e.g., avatars) that may share at least one characteristic with one or more subjects. The system may run one or more simulations to convert real-world animal data into simulated data to be used in the simulation game, and/or transform animal data into a form that can be inputted into a simulation system. For example, a user may want to compete in a head-to-head tennis match with Athlete X within a simulation game (e.g., virtual reality game), which would include simulated animal data based on at least a portion of the real animal data from both the one or more users and Athlete X. Both the user and Athlete X may utilize one or more sensors that transmit a variety of biological data (e.g., ECG, heart rate, biomechanical data such as racquet swing data, location data) to the system, which may be further computed into one or more additional readings (e.g., stress levels, swing speed), transformed into a game-based metric (e.g., an "energy level" bar, "swing power" bar), or incorporated into one or more simulations to generate a simulated data output. In a refinement, the one or more simulation game users or spectators participating in or watching the game can place a wager based on the game/competition (e.g., on the match played against Athlete X within the gaming system), create or modify one or more products, determine probability or odds for an occurrence of an outcome of an event, revise previously determined probability or odds for an event, or formulate a strategy. In exchange for providing at least a portion of their animal data, the one or more participants in the game or competition (e.g., Athlete X and/or the one or more game players) may receive a portion of consideration from wagers placed (e.g., from winning bets) or purchases made within the competition that directly or indirectly utilizes their data. For example, a star tennis player may provide his or her biological data to a video game simulation so that a game user can play as, or against, a virtual representation of that star tennis player. In this situation, the user may pay a fee to the simulation operator (e.g., video game company) for access to the data or a derivative thereof (e.g., artificial data generated based upon at least a portion of the real animal data), a portion of which may go to the star tennis player. Alternatively, the simulation operator may pay a license fee or provide other consideration (e.g., a percentage of game sales or data-related products sold) to the athlete for the use of the data within the simulation game. In another example, the simulation operator can enable one or more bets/wagers to be placed on the game itself (e.g., between the user and the star tennis player) or proposition bets within the game (e.g., micro bets based upon various aspects within the game). In a refinement, the one or more prop bets are based upon at least a portion of the animal data and/or one or more derivatives thereof (including simulated data). In this situation, the user and/or star tennis player may receive a portion of the consideration from each bet placed, the total number of bets, and/or one or more products created, offered, and/or sold based upon at least a portion of the data. In another example, in a fitness class, an instructor may be able to receive compensation on any bets made between the instructor and user (e.g., who can pedal the most miles in 10 minutes), or a gamer may receive compensation for proposition bets that incorporate at least a portion of their biological data. In a refinement, one or more subjects that provide at least a portion of their animal data to one or more third parties as part of one or more simulations may receive consideration for providing access to their data.

In a refinement, the simulation system creates artificial data for one or more simulated subjects (which may be representative of one or more real-world subjects) featuring one or more characteristics that are desirable to the user or group of users. The artificial data created may then be used (e.g., as part of a baseline) in one or more further simulations in order to create one or more artificial data sets that can be utilized to calculate, compute, derive, extract, extrapolate, simulate, create, modify, assign, enhance, estimate, evaluate, infer, establish, determine, convert, deduce, observe, communicate, or action upon one or more predictions or probabilities. For example, if a healthcare provider wants to determine the effectiveness a specific dosage of a drug to a targeted patient who features specific characteristics (e.g., age, weight, height, medical history, social habits, a specific medical condition), the healthcare provider can run one or more simulations utilizing other patient data that shares one or more common characteristics with the targeted patient, including patients that were provided the specific dosage of drug or medication in order to determine the effect the drug will have on the targeted patient, with the healthcare provider also utilizing simulated data to evaluate one or more other potential outcomes (e.g., the probability that administering the drug will lead to a heart attack; the probability that the drug will induce severe nausea, etc.). If the healthcare provider does not have a large enough data set or requires additional data to run one or more simulations to determine the drug impact on a subject with the specific characteristics desired, the healthcare provider can create artificial data sets by running one or more simulations or by other methods described herein that feature the specific characteristics of the targeted patient with the one or more variables (e.g., the quantity of drug) that are desired by the healthcare provider as part of the probability assessment. The healthcare provider can then utilize the one or more artificial data sets as part of a baseline in one or more further simulations to determine the probability of an occurrence happening. In a refinement, the healthcare provider may charge the insurance company (or vice versa) for each simulation run, which may result in a benefit provided to one or more parties (e.g., the one or more simulations may provide a healthcare provider with a probability of an occurrence happening). In a variation, the targeted patient, the insurance provider, the healthcare provider, or a combination thereof, may choose to have the one or more simulations conducted prior to having in-patient care administered to determine the one or more effects a given action taken or method used by a healthcare provider may have on the patient.

In a refinement, one or more artificial intelligence techniques can be utilized to evaluate one or more biological sensor outputs, as well as conduct one or more data quality assessments, both to collected sensor data as well as the generated artificial data values. In another refinement, one or more neural networks can be trained to generate one or more data values that can be utilized to test one or more biological sensor outputs (e.g., signals, readings), as well as algorithms utilized to produce the one or more sensor outputs.

In another refinement, one or more artificial data values are generated when detecting and replacing one or more values (e.g., outlier values, missing values) generated from one or more biological sensors. In many cases, the one or more sensors produce measurements (e.g., analog-derived measurements such as raw AFE data) that are provided to a server, with a server applying methods or techniques to filter the data and generate one or more values (e.g., heart rate values). However, in cases where data has an extremely low signal-to-noise ratio, or in some cases when one or more values are missing, pre-filter logic may be required to generate artificial data values. In one aspect, a pre-filter method whereby the system takes a number of steps to "fix" the data generated from the sensor to ensure that the one or more data values generated are clean and fit within a predetermined range is proposed. The pre-filter logic would ingest the data from the sensor, detect any outlier or "bad" values, replace these values with expected or "good" artificial values and pass along the "good" artificial values as its computation of the one or more animal data values (e.g., heart rate values). The term "fix" refers to an ability to create one or more alternative data values (i.e., "good" values) to replace values that may fall out of a preestablished threshold, with the one or more "good" data values aligning in the time series of generated values and fitting within a preestablished threshold. These steps would occur prior to any logic taking action upon the received biological data to calculate the one or more biological data values (e.g., heart rate values).

Advantageously, the pre-filter logic and methodology for identification and replacement of one or more data values can be applied to any type of sensor data collected, including both raw and processed outputs. For illustration purposes, and while raw data such as analog front end measurements (AFE) can be converted into other wave forms such as surface electromyography (sEMG) signals, the presently disclosed and claimed subject matter will focus on conversion to ECG and heart rate (HR) values. However, the presently disclosed and claimed subject matter is not limited to the type of sensor data collected. As previously described, the pre-filter logic becomes important in a scenario whereby the signal-to-noise ratio in the time series of generated AFE values from one or more sensors is at or close to zero, or numerically small. In this case, one or more systems or methods to generate one or more heart rate values may ignore one or more such values, which in some cases may result in no heart rate value generated or a generated heart rate value that may fall outside the preestablished parameters, patterns and/or thresholds. Such AFE values may result from the subject taking an action that increases one or more other physiological parameters (e.g., muscle activity), or in competing signals derived from the same sensor being introduced or deteriorating the connection, or from other variables. This in turn may make for an inconsistent HR series.

To solve for this problem, a method whereby one or more data values are created by looking at future values rather than previously generated values has been established. More specifically, the system may detect one or more outlier signal values and replace outlier values with one or more signal values that fall within an expected range (e.g., the established upper and lower bounds), thus having the effect of smoothing the series while at the same time decreasing the variance between each value. The established expected range may take into account a number of different variables including the individual, the type of sensor, one or more sensor parameters, one or more of the sensor characteristics, one or more environmental factors, one or more characteristics of the individual, activity of the individual, and the like. The expected range may also be created by one or more artificial intelligence or machine learning techniques that uses at least a portion of previously collected sensor data and/or one or more derivatives thereof, and possibly one or more of the aforementioned variables, to predict what an expected range may be. The expected range may also change over a period of time and be dynamic in nature, adjusting based on one or more variables (e.g., the activity the person is engaged in or environmental conditions). In a variation, one or more artificial intelligence techniques may be utilized, at least in part, to generate one or more artificial signal values within the expected range (e.g., upper and lower bound) derived from at least a portion of collected sensor data and/or one or more derivatives thereof from the one or more sensors.

To achieve the desired outcome of creating one or more values based upon future values, the system first samples one or more of the sensor's "normal" or "expected" AFE values and applies statistical tests and exploratory data analysis to determine the acceptable upper and lower bound of each AFE value generated by the sensor, which may include outlier detection techniques like interquartile range (IQR), distribution and percentile cut offs, kurtosis, and the like. A normal or expected AFE value may be determined by utilizing at least a portion of previously collected sensor data. What is considered to be a normal or expected AFE value may also vary by sensor, by sensor parameter, or by other parameters/characteristics that may be factored into what is determined to be normal or expected (e.g., the subject, the activity the subject is engaged in).

Once an outlier is identified, the pre-filter logic then uses a backward fill method to fill the one or more outliers (i.e., AFE values that fall outside of the accepted lower and upper bound) with the next value available that falls within the normal range in the current window of samples. This results in a cleaner and more predictable time-series of values which is devoid of un-processable noise. In a refinement, the one or more values are produced by utilizing one or more artificial intelligence techniques in which the model has been trained to predict the next AFE value given a past sequence of AFE values, and/or as a replacement to one or more outliers in order to enable the sequence of values to fall within a normal range. In a variation, a user could utilize a heuristic or mathematical formula-based method that describe waveforms similar to what an AFE signal produced from a sensor would be.

For heart rate values, the system may increase the amount of data used by the pre-filter logic processing the raw data to include n number of seconds worth of AFE data. An increase in the amount of data collected and utilized by the system enables the system to create a more predictable pattern of HR generated values as the number of intervals that are used to identify the QRS complex is increased. This occurs because HR is an average of the HR values calculated over one second sub-intervals. The n number of seconds is a tunable parameter that may be pre-determined or dynamic. In a refinement, one or more artificial intelligence techniques may be utilized to predict the n number of seconds of AFE data required to generate one or more values that fall within a given range based on one or more previously collected data sets.

Table 3 provides example pseudocode for generating artificial animal data (e.g., artificial sensor values) utilizing the LSTM method for training and testing of AFE prediction under noisy inputs, one or more parameters of which may be adjustable (tunable).

TABLE 3

| Pseudocode for training and test of AFE prediction under noisy inputs |
| --- |
| Step 1. Configure the network<br>• Step 1a. Set Timesteps = nt {=20}<br>• Step 1b. Set Optimizer ADAM(learning rate = lr, beta = b) {lr = 0.002; b=0.5}<br>• Step 1c. Set epochs = ne {=100}<br>• Step 1d. Set batch size for training = bs {=512}<br>• Step 1e. Set input rows for test = rc {=1000}<br>Step 2. Load available animal data (e.g., ECG data)<br>• Step 2a. Read available animal data from file to dataframe(table)<br>Step 3. Create LSTM Model<br>• Step 3a. Create sequential LSTM model with input sequence = timesteps, nu units {nu=20}<br>• Step 3b. Add Hidden layer with number of units to 10 {nu=10} with a LeakyReLU (Leaky Rectified Linear Unit with alpha=0.3) output and a dropout of 0.3<br>• Step 3c. Add output layer with LeakyReLU for real-valued animal data output<br>• Step 3d. Compile model and set Mean Squared Error (MSE) as loss function and ADAM optimizer<br>Step 4. Train Model<br>• Step 4a. Read the data frame created above<br>• Step 4b. Reshape the data<br>• Step 4c. Create tuples of input sequences of length equal to timesteps, and 1 real-valued output (the animal data reading)<br>• Step 4d. Apply standardization to the data ((X- mean)/std dev) to normalize values to [-1,1]<br>• Step 4e. Fit data into the model<br>Step 5. Test Model<br>• Step 5a. Pass normalized input of real animal data readings as sequence of length timesteps to predict next animal data reading<br>• Step 5b. Drop the first animal data from previous sequence and append prediction to create next input<br>• Step 5c. Pass next input to model to predict next reading<br>• Step 5d. Observe output and Repeat |

Figure 11:
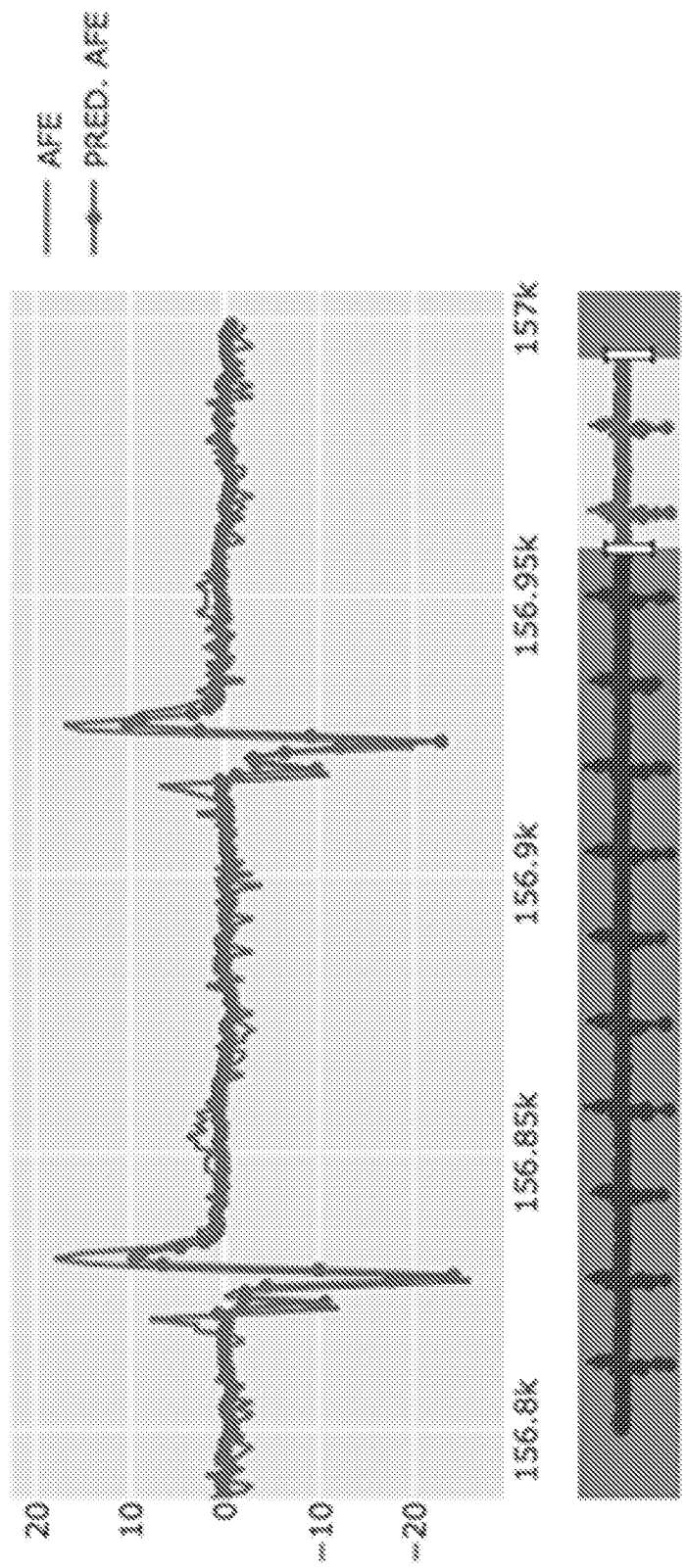
FIG. 11 illustrates an out-of-sample test of raw data measurements from a biological sensor with predicted raw data values generated using a LSTM Neural Network.

FIG. 11 illustrates an out-of-sample test of AFE data (labeled "AFE" in the Figure) derived from a biosensor with predicted AFE values generated using a LSTM Neural Network (labeled "PRED, AFE" in the Figure) with an input layer with 15 nodes and a hidden layer with 10 nodes. The number of nodes can be a tunable parameter. The history of AFE values used to make this prediction is 20 (i.e. looking back 20 timestamps). The number of historical values can be a tunable parameter. In this illustration, the model is trained on AFE data that was devoid of noise or disturbances caused during physical activity that may introduce signals that are not true AFE values. This allows the system to predict what a normal AFE value is given a past sequence of normal AFE values. In addition to training the model for baseline normal AFE values, the system can also be trained with other collected data which can include both animal data and non-animal data sets. Such training can occur with historical data as well as current (e.g., active) data sets (e.g., data collected in real-time or near real-time such as in a live sporting event) as the data is received by the system. The system can utilize such collected data to generate more accurate predictions, probabilities, or possibilities, as well as tailor the one or more predictions, probabilities, or possibilities to one or more targeted individuals based on their previously collected data attributes.

While the pre-processing of the data may not replicate the possible R-peaks in a QRS complex, the pulling in of one or more noisy values into the range of a normal or expected signal allows the downstream filter and system generating the HR values to produce one or more HR values that fall within the expected range in absence of a quality signal. Additional details related to a system for measuring a heart rate and other biological data are disclosed in U.S. patent application Ser. No. 16/246,923 filed Jan. 14, 2019 and U.S. Pat. No. PCT/US20.13461 filed Jan. 14, 2020; the entire disclosures of which are hereby incorporated by reference.

In a refinement, the simulation system generates artificial data values to complete a data set. For example, a sensor that is collecting any given biological data (e.g., heart rate) may have an occurrence that prevents the sensor from collecting, analyzing and/or distributing data to the simulation (e.g., the one or more sensors fall off the subject, stops collecting data because the sensor runs out of power, and the like). In this example, the simulation system can create one or more artificial data sets to complete the data set (e.g., if a subject is on a 40 minute run and the heart rate sensor runs out of battery after 30 minutes, the simulation system can generate the final 10 minutes of heart rate data artificially, which may take into account one of more variables including previously collected data and data sets, speed, distance, environmental conditions, and the like).

In another refinement, a user provides one or more commands, and one or more computing devices (e.g., simulation system, computing device, or a third party) take one or more actions that utilize at least a portion of the simulated data or its derivative to fulfill at least a portion of the one or more commands. The command may be initiated via a number of ways including a physical cue (e.g., clicking on an icon on an application) or a verbal cue (e.g., speaking with a voice-activated virtual assistant or other communication medium). The one or more commands may also be initiated neurologically. For example, a computing device (e.g., brain-computer interface) may acquire one or more of the subject's brain signals from neurons, analyze the one or more brain signals, and translate the one or more brain signals into commands that are relayed to an output device to carry out a desired action. Acquisition of brain signals may occur via a number of different mechanisms including one or more sensors that may be implanted into the subject's brain). Based upon the one or more commands, the one or more actions taken by the one or more computing devices include at least one of: (1) recommend whether or not to make one or more wagers; (2) create, enhance, modify, acquire, offer, or distribute one or more products; (3) evaluate, calculate, derive, modify, enhance, or communicate one or more predictions, probabilities, or possibilities; (4) formulate one or more strategies; (5) take one or more actions, including placing one or more bets; (6) mitigate or prevent one or more risks; (7) recommend one or more actions; or (8) a combination thereof. For example, a user may verbally communicate to their voice-activated assistant that the user wants to make a specific bet. The voice-activated assistant may inform the user whether or not to place a bet by evaluating a probability or odds based in part on at least a portion of the simulated animal data. A bet may then be placed. In another example, a user may verbally communicate to their voice-activated assistant that the user wants to engage in a physical activity when the user has a heart condition. The voice-activated assistant may inform the user whether or not to engage in the activity by evaluating a probability or odds based in part on at least a portion of the user's simulated animal data to determine heart and other health risks associated with the physical activity.

In a refinement, the one or more computing devices may take one or more series of steps in order to obtain a response to the command provided by the user. For example, a user may request a program on a computing device to generate information via one or more simulations, from which a response may be provided to the user (e.g., an optimal exercise plan that includes time, activity, targeted biological readings in order to burn a targeted number of calories). In another example, if a user provides a verbal command to the computing device or third-party system to determine whether or not to place a bet, the voice-activated assistant may run at least one simulation to inform the user whether or not to place a bet. In a variation, the computing device will take one or more actions on behalf of the user based upon one or more thresholds set by the user, with the one or more actions being initiated either directly or indirectly as a result of at least a portion of the simulated data or one or more derivatives thereof. For example, the computing system or third party may have the ability to monitor in real-time or near real-time various inputs and variables that may change the probability of an occurrence happening. By running one or more simulations using at least a portion of the animal data at any given time, the system may provide a revised odds of an occurrence happening which may trigger a bet to occur. In this scenario and in the context of sports betting, the user may set the system to place a bet upon a probability threshold being reached (e.g., if the probability of Player A's heart rate going above 200 bpm in the 4th game of the 3rd set of Match X reaches above 85%, the user may set the system to place a bet on Player A's heart rate reaching over 200 in the 4th game of the 3rd set of Match X) or provide the user with a notification that a bet should be placed (e.g., verbal notification, kinesthetic notification like a vibration on a smartwatch, visual notification like a pop up within a virtual reality or augmented reality system, a text message on a phone, an alert on an app, and the like). Derivatives may include one or more computed assets, insights, and/or predictive indicators. In a variation, at least a portion of the simulated data is utilized to create one or more insights, computed assets, or predictive indicators. In this scenario, the computing system or third party may create the probability of an occurrence happening based at least in part on simulated data that is generated by running one or more simulations.

In another refinement, simulated data can be used as part of a health monitoring system. For example, a health monitoring system such as a health platform or application can be operable to utilize one or more artificial intelligence techniques to correlate data sets to identify known biological-related issues from one or more targeted individuals or groups of targeted individuals, as well as identify hidden patterns within the one or more data sets to identify biological-related issues based upon the collected data. This may include finding entirely new patterns within data that has never previously been correlated with known issues, or finding new patterns amongst one or more data sets that may identify new issues. The application can be operable to further run one or more simulations to generate one or more artificial data sets that can enable a user to at least one of: (i) evaluate, calculate, derive, modify, enhance, or communicate one or more predictions, probabilities, or possibilities; (ii) formulate one or more strategies; (iii) take one or more actions; (iv) mitigate or prevent one or more risks; (v) recommend one or more actions; or (vi) a combination thereof. The artificial data generated from the one or more simulations can be utilized to create, modify, or enhance one or more insights, computed assets, or predictive indicators, or utilized in another one or more simulations that can further create, enhance, or modify one or more insights, computed assets, or predictive indicators. Communication of the animal data and one or more derivatives thereof (e.g., simulated data, predictive indicators, computed assets) to the one or more users of the monitoring system can occur in real-time or near real-time to provide a holistic view of the targeted subject, as well as potential future risks derived from the simulated data. This may occur via display within the application (e.g., biological data such as heart rate, respiratory rate, biological fluid level, and the like, as well as insights such as "energy level," the probability of experiencing a biological event, immediate risk threats related to one or more biological readings based upon one or more simulations run, and the like) or communicated in other forms (e.g., verbally via a virtual assistant; visually as part of augmented reality display). Such health monitoring offerings can be used for a variety of industries including fitness, telehealth/healthcare (including remote patient monitoring), insurance, general business (e.g., employee wellness), aviation, automotive, and the like. In a variation, the health monitoring system may detect a health or medical condition based on one or more simulations being run that utilize at least a portion of collected sensor data, which may trigger either an alert being sent to another one or more computing devices (e.g., hospital, medical professional).

Advantageously, such information may be communicated in real-time or near real-time via direct sensor communication with a web browser. In a refinement, simulated data can be generated from, or utilized as part of, a data tracking system, and in particular, a biological (animal) data tracking system, which includes a connection application and a server. The connection application establishes wireless communication with each of a plurality of wireless communication-enabled data sensors (e.g., wearable biological sensors and/or other wireless communication-enabled data sensors), receives one or more streams of data from the sensors, and displays, via a browser application, one or more readings derived from at least a portion of the streamed data. The server may transmit the connection application to the browser in response to a user accessing a web page. The connection application may transmit the one or more streams of data to the server which then calculates one or more readings. The plurality of wireless communication-enabled sensors may include at least two different types of sensors, including sensors that communicate with the connection application using different communication interfaces. At least one of the readings, which includes simulated data or one or more derivatives thereof, may be derived from at least a portion of the data streams from two different sensors. The one or more data streams may also be inputs in one or more simulations, from which simulated data can be created. In a variation, the one or more readings may also be derived from one or more simulations that utilize at least a portion of the one or more data streams from two or more different sensors. The connection application may be operable to transmit one or more commands to a remote-controlled device and/or a subset of the plurality of sensors to change one or more sensor settings, which may occur in sequence or simultaneously.

In another refinement, simulated data can be generated from, or utilized as part of, a data tracking system, and in particular, a biological (animal) data tracking system, which includes one or more wireless communication-enabled data sensors (e.g., biological data sensors), a computing device, and a connection application. The one or more wireless communication-enabled data sensors may include at least two different types of sensors which may communicate with the connection application using different communication interfaces. The computing device includes a network connection (e.g., internet) and browser application (e.g., executing browser software). The connection application, which executes within the browser, is configured (e.g., programmed) to establish one or more wireless communication links with each of the one or more sensors, receive one or more streams of data from the one or more sensors, and display, via the browser application, one or more readings derived from at least a portion of the streamed data. The connection application may also transmit one or more commands to the one or more wireless communication-enabled data sensors to change, adjust, and/or modify one or more sensor settings. At least one of the readings, which may include simulated data, may be derived from at least a portion of the one or more data streams from two or more different sensors. The one or more data streams may also be inputs in one or more simulations, from which simulated data can be created. In a variation, the one or more readings may also be derived from one or more simulations that utilize at least a portion of the one or more data streams from two or more different sensors. The system may also include a server configured to receive the one or more streams of data via a network connection (e.g., internet) and compute the readings. The server may also be operable to transmit the connection application program to the browser in response to a user accessing a web page.

In another refinement, simulated data can be generated from, or utilized as part of, a method for tracking biological (animal) data which includes transmitting a connection application from a server to a browser, detecting the at least one wireless communication-enabled sensor, wirelessly receiving one or more data streams from the at least one sensor, and displaying one or more readings. The server transmits the application to the browser in response to a user accessing a web page. The connection application detects the one or more sensors and directly receives at least a portion of the one or more data streams. The one or more readings are derived from at least a portion of the one or more data streams and displayed, at least in part, in the browser. The one or more readings may include simulated data. Characteristically, the one or more data streams may also be inputs in one or more simulations, from which simulated data can be created. The method may also include transmitting at least a portion of the one or more data streams from the browser to the server and transmitting the one or more readings from the server to the browser. The connection application may be operable to send one or more commands to the one or more sensors to change one or more sensor settings. The one or more sensors may include at least two types of sensors which may transmit one or more data streams to the connection application using two different communication interfaces. Additional details related to a data tracking system that utilizes simulated data are disclosed in U.S. patent Ser. No. 16/274,701 filed Feb. 13, 2019 and U.S. Pat. No. PCT/US20/18063 filed Feb. 13, 2020, the entire disclosures of which are hereby incorporated by reference.

Advantageously, simulated data may be utilized as part of an unmanned aerial vehicle-based sensor data collection and distribution system. An unmanned aerial vehicle-based data collection and distribution system can include a source of animal data that is electronically transmittable. The source of animal data can include at least one biological sensor. The animal data can be gathered from at least one targeted individual or group of targeted individuals. The system can also include one or more unmanned aerial vehicles (e.g., drones, high-altitude long-endurance aircraft, high-altitude pseudo satellite, atmospheric satellites, balloons, multirotor drones, airships, a fixed-wing aircraft, low altitude systems) that receive the animal data from one or more sensors and are in communication with one or more other computing devices (e.g., home stations, other computing systems). Characteristically, the one or more unmanned aerial vehicles include a transceiver operable to receive one or more signals or readings from the source of animal data, collect data from one or more sensors that are part of the UAV (e.g., optical sensors, temperature sensors, and the like attached to, integrated with, connected with, or associated with the one or more UAVs), and/or provide (e.g., send) data to another computing device or make the data accessible via a cloud. The one or more UAVs may operate as part of a network of UAVs (e.g., a cellular network that utilizes a network of drones for one or more data-related functions), network comprised of one or more UAVs and non-UAVs (e.g., ground stations), or plurality of networks In a refinement, one or more simulations incorporating collected sensor data can be run to predict a targeted individual's one or more animal data readings (e.g., location, movements) and optimize the one or more UAVs. The one or more simulations can include collected sensor data, one or more characteristics of the one or more targeted individuals (e.g., the activity the one or more targeted individuals are engaged in), one or more types of non-animal data (e.g., weather, search results or content from one or more mobile devices), and the like. For example, collecting location data from one or more targeted individuals to predict one or more movements via one or more simulations can enable efficiencies across the one or more UAVs including optimizing UAV formations (e.g., three-dimensional formations) to ensure optimal line of sight with the one or more targeted individuals, mapping of the UAVs, routing of the UAVs (e.g., maximizing efficiency of any given route to minimize energy consumption), sharing of data across UAVs and other computing devices (e.g., determining data may need to be shared or made available to other UAVs or computing devices vs. stored based upon the one or more predicted movements of the one or more targeted individuals, what information may need to be duplicated across UAVs to ensure a seamless handoff based on predicted movements, and the like), communication between systems (e.g., maximizing the likelihood of a targeted detection or connection between the one or more UAVs and the one or more sensors based on a targeted individual's location), antenna positioning, type of antenna utilized to communicate with one or more sensors or systems, antenna array positioning, optimization of beam patterns and directions based upon predicted targeted individual location, placement/formation of the one or more UAVs based upon predicted targeted individual location (e.g., including projected changes in altitude, elevation), and the like. The one or more actions taken by the one or more UAVs upon the simulated data may result in an optimization of bandwidth (e.g., more available bandwidth), increased energy conservation for the one or more UAVs (e.g., enabling the UAV to utilize energy for additional functions or increased flight time), more reliable communication between sensor and UAV (e.g., stronger signal strength, decreased data packet loss), maximization of coverage area, and the like.

In another refinement, artificial data may be generated utilizing one or more statistical models or artificial intelligence techniques, from which one or more simulations can be run to provide information that enables the one or more UAVs to take one or more actions. Based upon at least a portion of received sensor data from the one or more targeted individuals, the one or more UAVs may be operable to provide (e.g., send) data to one or more computing devices to run one or more simulations, or run one or more simulations on the one or more UAVs. Based upon the output from the one or more simulations, the one or more UAVs can take one or more actions. For example, the collected biological sensor data from the one or more targeted individuals may trigger the one or more UAVs or the home station controlling the one or more UAVs to run one or more simulations related to the one or more targeted individuals, from which one or more predictions, probabilities or possibilities may be calculated, computed, derived, extracted, extrapolated, simulated, created, modified, enhanced, estimated, evaluated, inferred, established, determined, deduced, observed, communicated, or actioned upon. More specifically, the one or more UAVs may detect or capture information that detects biological-based information based upon the one or more sensors (e.g., the targeted subject is experiencing a medical event such as a heart attack or a stroke), analyze the collected sensor data (e.g., utilizing one or more machine learning techniques to find patterns within the data to generate predictive or probability-based information) or provide the data for analysis via another computing devices that accesses the data (e.g., via the cloud), and take one or more actions (e.g., send an alert to another system such as a hospital system notifying the system of such an alert, deliver one or more medications or drugs as a result of the UAV's analysis of the one or more signals or readings; receive the analyzed information from the computing device providing analysis and send an alert to a third party). The alert could include the one or more biological readings (e.g., a summary of the readings, location of the targeted individual from which the biological readings were captured) and/or other data (e.g., a predictive indicator communicating the likelihood a medical event will occur based on the collected information), along with information related to the one or more UAVs. In a further refinement, the one or more UAVs may detect biological-based information that triggers the one or more UAVs to run one or more simulations, or triggers another computing device receiving or acquiring data from the one or more UAVs to run one or more simulations, from which one or more predictions, probabilities, or possibilities are derived (e.g., the collected biological sensor data provides readings that indicate abnormalities within the data that is associated with a specific medical episode, so the system runs one or more simulations to determine the likelihood that the targeted individual will experience the medical episode within n period of time), and one or more actions are taken (e.g., the UAV may deliver a first-aid kit or other medical devices to aid in addressing the medical episode, or send an alert to another system such as a hospital system or medical emergency system, or send an alert to the targeted individual that a medical episode is about to occur). In another refinement, one or more UAVs may detect the animal data and another one or more UAVs may take the action (e.g., one UAV detects the biological data, another UAV runs the one or more simulations, another UAV interprets the captured sensor data and generated artificial information to project the likelihood of a medical event occurring, and another UAV delivers the one or more drugs, prescriptions, or sensing/medical equipment to address the medical episode and mitigate/prevent risk). In another refinement, one or more UAVs may detect the animal data and another one or more computing devices may take the action (e.g., the UAV captures the sensor data, sends the data to a third-party to run a simulation and deliver the appropriate drug/prescription/equipment based upon the output).

The simulated data derived from at least a portion of the UAV-collected sensor data or one or more derivatives thereof can be used either directly or indirectly: (1) as a market upon which one or more wagers are placed or accepted; (2) to create, modify, enhance, acquire, offer, or distribute one or more products; (3) to evaluate, calculate, derive, modify, enhance, or communicate one or more predictions, probabilities, or possibilities; (4) to formulate one or more strategies; (5) to take one or more actions; (6) to mitigate or prevent one or more risks; (7) to recommend one or more actions; (8) as one or more signals or readings utilized in one or more simulations, computations, or analyses; (9) as part of one or more simulations, an output of which directly or indirectly engages with one or more users; (10) as one or more core components or supplements to one or more mediums of consumption; (11) in one or more promotions; or (12) a combination thereof. For example, one or more simulations can be run related to the individual locations for a group of targeted individuals to predict their expected individual locations in order to position the one or more UAVs or network of UAVs to ensure optimal placement. Additional details of unmanned aerial vehicle-based data collection and distribution systems for sensor data that can incorporate simulation systems are disclosed in U.S. patent Ser. No. 16/517,012 filed Jul. 19, 2019 and U.S. Pat. No. PCT/US20/42705 filed Jul. 20, 2020; the entire disclosures of which is hereby incorporated by reference.

Simulated data can also be used to change, adjust, or modify one or more sensor settings. In a refinement, one or more simulations are run that result in a change, adjust, or modify one or more sensor settings. In a variation, the simulation system or computing device receiving the simulated data or one or more derivatives thereof (e.g., an alert based on the simulated data) automatically changes, adjusts, or modifies the one or more sensor settings based on the result of the one or more simulations, which may occur utilizing one or more artificial intelligence techniques. For example, if the simulation generates simulated data that demonstrates based upon one or more sensor readings from a targeted subject that the targeted subject's one or more sensor readings have a high probability of going from normal to irregular readings (e.g., in the event the simulation predicts a targeted subject will have a heart attack), the simulation system or other computing device can automatically change one or more sensor settings (e.g., increase the sampling rate of the sensor; increase the frequency upon which one or more signals or readings are provided, change/adjust/modify the one or more computing devices receiving the sensor data. In this example, if the data readings are expected to become irregular, the one or more readings may be automatically sent to a healthcare-related system or a medical professional). In another example, if the simulation generates simulated data that demonstrates the targeted subject is predicted to have normal ECG readings, the simulation system of computing device receiving the simulated data or one or more derivatives thereof may modify the sampling rate on the sensor (e.g., decrease the rate), or decrease the frequency of data being provided by the sensor to the one or more computing devices (e.g., change the data streaming rate from continuous to intermittent in order to preserve battery life). In another example, the simulated data may trigger a targeted subject to have a virtual consultation with a medical professional via the simulation system (e.g., which may be a remote health monitoring/telehealth platform) or other computing device. Based upon the simulated data, the medical professional may change, modify, or adjust one or more sensors being utilized by the targeted subject (e.g., the camera) so that the medical professional can tailor the one or more sensors for their specific needs (in the camera example, examine one or more specific parts of the body). In a variation, and based upon the simulated data, a medical professional may change, modify, or adjust the one or more sensor settings of the one or more sensors being used by the one or more targeted subjects so that the one or more sensors can capture data more relevant to the monitoring, supervision, or care of the one or more targeted subjects utilizing the one or more sensors. For example, the clinician may decide to change (e.g., manually override a setting) or adjust a sensor setting to more precisely capture the relevant animal data required to make a decision on the monitoring, treatment, hospital admission, review, or follow up of the patient.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method comprising:
receiving, by a computing device, one or more sets of real animal data at least partially obtained from one or more sensors that receive, store, and/or send information related to one or more targeted individuals, the one or more sensors including a biological sensor configured to measure electrical signals in or derived from a targeted subject's body, the one or more targeted individuals including a player in an athletic event;
transforming the electrical signals into one or more heart rate values and/or electrocardiogram (ECG) data;
generating, by the computing device, simulated animal data from at least a portion of real animal data or one or more derivatives thereof, wherein one or more parameters or variables of the one or more targeted individuals are modified, the simulated animal data including artificially-created data that shares at least one biological function with a human or another Animal; and
assessing fatigue for the player in the athletic event from the simulated animal data from a running total for an amount of time the player has an elevated heart rate, diastolic blood pressure, systolic blood pressure, perspiration rate and/or distance run wherein the simulated animal data is generated by a method using a recurrent neural network (RNN) comprising:
(a) receiving real animal data from multiple events, wherein training animal data readings are timestamped and recorded at predetermined time intervals;
(b) training an untrained recurrent neural network model using the real animal data to form a trained recurrent neural network model, wherein the training includes:
(i) using a sequence of observations as input;
(ii) performing the training over a plurality epochs using an error metric and an optimizer for updating network weights;
(c) generating simulated animal data by applying the trained neural recurrent network model, wherein the trained recurrent neural network model predicts physiological data including heart rate based on the real animal data;
(d) performing in-sample forecasting, wherein the simulated animal data is generated from a subset of the real animal data to predict future values based on known outcomes;
(e) performing out-of-sample forecasting, wherein the simulated animal data is generated from observations that were not part of the real animal data to predict future values based on previously unseen data; and
(f) modifying one or more parameters of simulated animal data to alter physiological, biomechanical, or environmental conditions for predictive analysis.

2. The method of claim 1 wherein one or more simulations are executed to generate animal data by one or more simulation systems.

3. The method of claim 2 wherein at least a portion of the simulated animal data or one or more derivatives thereof are used to create, enhance, or modify one or more insights, computed assets, or predictive indicators.

4. The method of claim 2 wherein at least a portion of the simulated animal data or one or more derivatives thereof are used in one or more simulation systems, whereby the one or more simulation systems are at least one of: a game-based system, augmented reality system, virtual reality system, mixed reality system, or an extended reality system.

5. The method of claim 4 wherein one or more computing devices utilized as part of one or more simulation systems are operable to either directly or indirectly: (1) offer or accept one or more wagers; (2) create, enhance, modify, acquire, offer, or distribute one or more products; (3) evaluate, calculate, derive, modify, enhance, or communicate one or more predictions, probabilities, or possibilities; (4) formulate one or more strategies; (5) take one or more actions; (6) mitigate or prevent one or more risks; (7) recommend one or more actions; (8) engage one or more users; or a combination thereof.

6. The method of claim 4, further comprising forecasting future biological readings for an activity.

7. The method of claim 2 wherein at least a portion of the simulated animal data is used as one or more inputs in one or more simulations.

8. The method of claim 7 wherein at least a portion of the simulated animal data or one or more derivatives thereof are used to create, enhance, or modify one or more insights, computed assets, or predictive indicators.

9. The method of claim 7 wherein at least a portion of the simulated animal data or one or more derivatives thereof are used in one or more simulation systems, whereby the one or more simulation systems are at least one of: a game-based system, augmented reality system, virtual reality system, mixed reality system, or an extended reality system.

10. The method of claim 9 wherein one or more computing devices utilized as part of one or more simulation systems are operable to either directly or indirectly: (1) offer or accept one or more wagers; (2) create, enhance, modify, acquire, offer, or distribute one or more products; (3) evaluate, calculate, derive, modify, enhance, or communicate one or more predictions, probabilities, or possibilities; (4) formulate one or more strategies; (5) take one or more actions; (6) mitigate or prevent one or more risks; (7) recommend one or more actions; (8) engage one or more users; or (9) a combination thereof.

11. The method of claim 1 wherein the one or more parameters or variables modified to generate simulated data are comprised of non-animal data.

12. The method of claim 1 wherein the simulated animal data is generated by randomly sampling at least a portion of the real animal data.

13. The method of claim 1 wherein the simulated animal data is generated by fitting the real animal data to a function with one or more independent variables or one or more adjustable parameters that are optimized to provide a fit to real animal data.

14. The method of claim 13 wherein the function is a line, polynomial, exponential, a Gaussian, Lorentzian, piecewise linear, or a spline between real data points.

15. The method of claim 13 wherein the one or more independent variables or adjustable parameters include time such that one or more biological parameters are associated with one or more virtual participants in a simulation as a function of time.

16. The method of claim 1 wherein the simulated animal data is generated by adding one or more offset values to each value of real animal data.

17. The method of claim 1 wherein at least a portion of the real animal data is transformed into simulated data by adding one or more random numbers to each value of a real data set.

18. The method of claim 1 wherein at least a portion of the simulated animal data is transformed into a lookup table to be used by a simulation.

19. The method of claim 1 wherein at least a portion of the simulated animal data is generated by fitting the real animal data to a probability distribution and then randomly sampling the probability distribution to assign one or more biological parameters to one or more virtual subjects.

20. The method of claim 19 wherein the probability distribution is selected from the group consisting of Bernoulli distributions, uniform distributions, binomial distributions, normal distributions, Poisson distributions, exponential distributions, and Lorentzian distributions.

21. The method of claim 19 wherein one or more sets of real animal data include one or more non-animal data variables or parameters which are applied as one or more parameters or variables in a simulation.

22. The method of claim 1 wherein a trained neural network generates the simulated animal data, the trained neural network having been trained with at least a portion of the real animal data or one or more derivatives thereof.

23. The method of claim 22 wherein the trained neural network is trained with at least a portion of simulated data.

24. The method of claim 22 wherein the one or more parameters or variables modified to generate simulated data are comprised of non-animal data.

25. The method of claim 22 wherein the trained neural network is a recurrent neural network.

26. The method of claim 22 wherein the trained neural network is a Long Short-Term Memory recurrent neural network.

27. The method of claim 22 wherein the trained neural network is a Generative Adversarial Network.

28. The method of claim 22 wherein the trained neural network utilized to generate the simulated animal data consists of one or more of the following types of neural networks: Feedforward, Perceptron, Deep Feedforward, Radial Basis Network, Gated Recurrent Unit, Autoencoder (AE), Variational AE, Denoising AE, Sparse AE, Markov Chain, Hopfield Network, Boltzmann Machine, Restricted BM, Deep Belief Network, Deep Convolutional Network, Deconvolutional Network, Deep Convolutional Inverse Graphics Network, Liquid State Machine, Extreme Learning Machine, Echo State Network, Deep Residual Network, Kohenen Network, Support Vector Machine, Neural Turing Machine, Group Method of Data Handling, Probabilistic, Time delay, Convolutional, Deep Stacking Network, General Regression Neural Network, Self-Organizing Map, Learning Vector Quantization, Simple Recurrent, Reservoir Computing, Echo State, Bi-Directional, Hierarchal, Stochastic, Genetic Scale, Modular, Committee of Machines, Associative, Physical, Instantaneously Trained, Spiking, Regulatory Feedback, Neocognitron, Compound Hierarchical-Deep Models, Deep Predictive Coding Network, Multilayer Kernel Machine, Dynamic, Cascading, Neuro-Fuzzy, Compositional Pattern-Producing, Memory Networks, One-shot Associative Memory, Hierarchical Temporal Memory, Holographic Associative Memory, Semantic Hashing, Pointer Networks, or Encoder-Decoder Network.

29. The method of claim 22 wherein a plurality of neural networks are utilized on at least a portion of the same animal data or one or more derivatives thereof to create simulated data.

30. The method of claim 22 wherein at least a portion of the simulated animal data is used either directly or indirectly: (1) as a market upon which one or more wagers are placed or accepted; (2) to create, modify, enhance, acquire, offer, or distribute one or more products; (3) to evaluate, calculate, derive, modify, enhance, or communicate one or more predictions, probabilities, or possibilities; (4) to formulate one or more strategies; (5) to take one or more actions; (6) to mitigate or prevent one or more risks; (7) to recommend one or more actions; (8) as one or more signals or readings utilized in one or more simulations, computations, or analyses; (9) as part of one or more simulations, an output of which directly or indirectly engages with one or more users; (10) as one or more core components or supplements to one or more mediums of consumption; (11) in one or more promotions; or (12) a combination thereof.

31. The method of claim 22 wherein one or more simulations occur utilizing at least a portion of the real animal data or one or more derivatives thereof to create simulated data that is utilized either directly or indirectly: (1) as a market upon which one or more wagers are placed or accepted; (2) to create, modify, enhance, acquire, offer, or distribute one or more products; (3) to evaluate, calculate, derive, modify, enhance, or communicate one or more predictions, probabilities, or possibilities; (4) to formulate one or more strategies; (5) to take one or more actions; (6) to mitigate or prevent one or more risks; (7) to recommend one or more actions; (8) as one or more signals or readings utilized in one or more simulations, computations, or analyses; (9) as part of one or more simulations, an output of which directly or indirectly engages with one or more users; (10) as one or more core components or supplements to one or more mediums of consumption; (11) in one or more promotions; or (12) a combination thereof.

32. The method of claim 1 wherein a simulation simulates based upon one or more targeted individuals engaged in at least one of: a fitness activity, a sporting event, a health assessment, or an insurance evaluation.

33. The method of claim 32 wherein at least a portion of the simulated animal data is used by one or more computing devices either directly or indirectly: (1) as a market upon which one or more wagers are placed or accepted; (2) to create, modify, enhance, acquire, offer, or distribute one or more products; (3) to evaluate, calculate, derive, modify, enhance, or communicate one or more predictions, probabilities, or possibilities; (4) to formulate one or more strategies; (5) to take one or more actions; (6) to mitigate or prevent one or more risks; (7) to recommend one or more actions; (8) as one or more signals or readings utilized in one or more simulations, computations, or analyses; (9) as part of one or more simulations, an output of which directly or indirectly engages with one or more users; (10) as one or more core components or supplements to one or more mediums of consumption; (11) in one or more promotions; or (12) a combination thereof.

34. The method of claim 1 wherein at least a portion of the simulated animal data or one or more derivatives thereof are used to create or modify one or more insurance services, identifications, classifications, rates, reimbursements, or a combination thereof.

35. The method of claim 1 wherein at least a portion of the simulated animal data or one or more derivatives thereof are used in one or more simulation systems, whereby the one or more simulation systems are at least one of: a game-based system, augmented reality system, virtual reality system, mixed reality system, or an extended reality system.

36. The method of claim 35 wherein one or more computing devices utilized as part of one or more simulation systems are operable to either directly or indirectly: (1) offer or accept one or more wagers; (2) create, enhance, modify, acquire, offer, or distribute one or more products; (3) evaluate, calculate, derive, modify, enhance, or communicate one or more predictions, probabilities, or possibilities; (4) formulate one or more strategies; (5) take one or more actions; (6) mitigate or prevent one or more risks; (7) recommend one or more actions; (8) engage one or more users; or (9) a combination thereof.

37. The method of claim 35 wherein at least a portion of a simulation user's animal data or one or more derivatives thereof are utilized as part of one or more simulations, the simulation user's animal data being at least partially obtained from one or more sensors.

38. The method of claim 37 wherein an apparatus that is in communication with the one or more simulation systems has one or more sensors in contact with, embedded in, affixed to, lodged in, or integrated with the apparatus, and provides at least a portion of a simulation user's data to a computing device, which includes at least a portion of a user's animal data or one or more derivatives thereof.

39. The method of claim 1 wherein the one or more sensors and/or one or more appendices thereof are affixed to, are in contact with, or send one or more electronic communications in relation to or derived from, one or more targeted individuals including a targeted individuals' body, eyeball, vital organ, muscle, hair, veins, biological fluid, blood vessels, tissue, or skeletal system, embedded in the one or more targeted individuals, lodged or implanted in one or more targeted individuals, ingested by the one or more targeted individuals, integrated to comprise at least a portion of the one or more targeted individuals, or integrated into or as part of, affixed to, or embedded within, a fabric, textile, cloth, material, fixture, object, or apparatus that contacts or is in communication with one or more targeted individuals, either directly or via one or more intermediaries.

40. The method of claim 1 wherein the one or more sensors includes at least one biosensor that gathers at least one of: physiological, biometric, chemical, biomechanical, location, environmental, genetic, genomic, or other biological data from one or more targeted individuals.

41. The method of claim 1 wherein the one or more sensors gathers, or provides information that can be converted into, at least one of the following types of data: facial recognition data, eye tracking data, blood flow data, blood volume data, blood pressure data, biological fluid data, body composition data, biochemical data, pulse data, oxygenation data, core body temperature data, skin temperature data, galvanic skin response data, perspiration data, location data, positional data, audio data, biomechanical data, hydration data, heart-based data, neurological data, genetic data, genomic data, skeletal data, muscle data, respiratory data, kinesthetic data, ambient temperature data, humidity data, barometric pressure data, or elevation data.

42. The method of claim 41 wherein the simulated animal data is utilized either directly or indirectly by one or more computing devices that provide information related to one or more insights, computed assets, or predictive indicators gathered or derived from the one or more sensors.

43. The method of claim 1 wherein a user chooses one or more parameters or variables for one or more simulations, one or more simulations occur, and one or more users acquire at least a portion of the simulated animal data or one or more derivatives thereof for consideration.

44. The method of claim 1 wherein a user provides one or more commands, and a one or more computing devices take one or more actions that utilize at least a portion of the simulated animal data or one or more derivatives thereof to fulfill at least a portion of the one or more commands.

45. The method of claim 1 wherein at least a portion of the simulated animal data is utilized to create, enhance, or modify one or more insights, computed assets, or predictive indicators.

46. The method of claim 45 wherein the one or more insights is a personal score or other indicator related to one or more targeted individuals or groups of targeted individuals that utilizes at least a portion of simulated data to (1) evaluate, assess, prevent, or mitigate animal data-based risk, (2) to evaluate, assess, and optimize animal data-based performance, or (3) a combination thereof.

47. The method of claim 1 wherein one or more computing devices take one or more actions on behalf of a user based upon one or more thresholds set by the user, with the one or more actions being initiated either directly or indirectly as a result of at least a portion of the simulated animal data or one or more derivatives thereof.

48. The method of claim 1 wherein the computing device is configured to detect at least one of: one or more outlier values generated from the one or more sensors, or one or more missing values related to data generated from the one or more sensors, and replaces the one or more outlier values or missing values with one or more artificial data values.

49. The method of claim 48 wherein the one or more artificial values align in a time series of generated values and fit within a preestablished threshold or range.

50. The method of claim 48 wherein the one or more artificial values are used, at least in part, as one or more inputs to derive animal data.

51. The method of claim 1 wherein one or more health classifications, treatments, procedures, identifications, rates, reimbursements, or services are created, modified, or assigned either directly or indirectly based upon at least a portion of the simulated animal data or one or more derivatives thereof.

52. The method of claim 1 further comprising providing predicted fatigue levels or expected caloric expenditure for the player in an athletic event.

53. The method of claim 1, wherein the modifying of one or more parameters of simulated animal data comprises adjusting physiological conditions selected from heart rate, hydration level, respiratory rate, or body temperature to simulate real-world performance variations.

54. The method of claim 1, wherein the modifying of one or more parameters of simulated animal data is performed in real-time or near real-time, enabling continuous recalibration of predictive models during an ongoing athletic event.

55. A system for generating and distributing simulated animal data, the system comprising:
one or more sensors that receive, store, and/or send information related to one or more targeted individuals, the one or more sensors including a biological sensor configured to measure electrical signals in or derived from a targeted subject's body, the one or more targeted individuals including a player in an athletic event; and
a computing device configured to execute steps of:
receiving one or more sets of real animal data at least partially obtained from one or more sensors that receive, store, or send information related to one or more targeted individuals, the simulated animal data including artificially-created data that shares at least one biological function with a human or another animal;
generating simulated animal data from at least a portion of real animal data or one or more derivatives thereof, wherein one or more parameters or variables of the one or more targeted individuals are modified and;
assessing fatigue for the player in an athletic event from the simulated animal data from a running total for an amount of time the player has an elevated heart rate, diastolic blood pressure, systolic blood pressure, perspiration rate and/or distance run, wherein at least a portion of the artificially-created data is processed by a trained recurrent neural network model by a method comprising:
(a) receiving real animal data from multiple events, wherein training animal data readings are timestamped and recorded at predetermined time intervals;
(b) training an untrained recurrent neural network model using the real animal data to form a trained recurrent neural network model, wherein the training includes:
(i) using a sequence of observations as input;
(ii) performing the training over a plurality epochs using an error metric and an optimizer for updating network weights;
(c) generating simulated animal data by applying the trained neural recurrent network model, wherein the trained recurrent neural network model predicts physiological data including heart rate based on the real animal data;
(d) performing in-sample forecasting, wherein the simulated animal data is generated from a subset of the real animal data to predict future values based on known outcomes; (e) performing out-of-sample forecasting, wherein the simulated animal data is generated from observations that were not part of the real animal data to predict future values based on previously unseen data; and
(f) modifying one or more parameters of simulated animal data to alter physiological, biomechanical, or environmental conditions for predictive analysis.

56. The system of claim 55 wherein one or more simulations are executed to generate simulated animal data.

57. The system of claim 55 wherein a trained neural network generates simulated animal data, the trained neural network having been trained with at least a portion of the real animal data or one or more derivatives thereof.

58. The system of claim 57 wherein the trained neural network is trained with at least a portion of simulated data.

59. The system of claim 55 wherein the simulated animal data is used either directly or indirectly: (1) as a market upon which one or more wagers are placed or accepted; (2) to create, modify, enhance, acquire, offer, or distribute one or more products; (3) to evaluate, calculate, derive, modify, enhance, or communicate one or more predictions, probabilities, or possibilities; (4) to formulate one or more strategies; (5) to take one or more actions; (6) to mitigate or prevent one or more risks; (7) to recommend one or more actions; (8) as one or more signals or readings utilized in one or more simulations, computations, or analyses; (9) as part of one or more simulations, an output of which directly or indirectly engages with one or more users; (10) as one or more core components or supplements to one or more mediums of consumption; (11) in one or more promotions; or (12) a combination thereof.

60. The system of claim 55 wherein a simulation simulates based upon one or more targeted individuals engaged in at least one of: a fitness activity, a sporting event, a health assessment, or an insurance evaluation.

61. The system of claim 55 wherein at least a portion of the simulated animal data or one or more derivatives thereof are used to create, modify, or assign one or more health procedures, services, treatments, codes, identifications, classifications, rates, reimbursements, or a combination thereof.

62. The system of claim 55 wherein a user chooses one or more parameters or variables for one or more simulations, one or more simulations occur, and one or more users acquire at least a portion of the simulated animal data or one or more derivatives thereof for consideration.

* * * * *